United States Patent
Wood et al.

(10) Patent No.: US 7,276,491 B2
(45) Date of Patent: Oct. 2, 2007

(54) ANTICOAGULANT AND FIBRINOLYTIC THERAPY USING P38 MAP KINASE INHIBITORS

(75) Inventors: Chester C. Wood, Ridgefield, CT (US); Thomas van der Poll, Amsterdam (NL)

(73) Assignees: Boehringer Ingelheim Pharmaceuticals, Inc., Ridgefield, CT (US); Boehringer Ingelheim Pharma GmbH & Co. KG, Ingelheim (DE)

( * ) Notice: Subject to any disclaimer, the term of this patent is extended or adjusted under 35 U.S.C. 154(b) by 378 days.

(21) Appl. No.: 11/009,480

(22) Filed: Dec. 10, 2004

(65) Prior Publication Data

US 2005/0159417 A1    Jul. 21, 2005

Related U.S. Application Data

(63) Continuation of application No. 10/630,599, filed on Jul. 30, 2003, now abandoned.

(60) Provisional application No. 60/403,422, filed on Aug. 14, 2002.

(51) Int. Cl.
- *A61K 38/48* (2006.01)
- *A61K 31/727* (2006.01)
- *A61K 31/5377* (2006.01)
- *A61K 31/519* (2006.01)
- *A61K 31/60* (2006.01)

(52) U.S. Cl. .................. 514/56; 424/94.64; 514/12; 514/165; 514/218; 514/233.2; 514/235.8; 514/243; 514/253.01; 514/262.1; 514/301; 514/314; 514/319; 514/456; 514/457

(58) Field of Classification Search ............. 514/218, 514/243, 233.2, 235.8, 253.01, 254.05, 319, 514/314, 56, 165

See application file for complete search history.

(56) References Cited

U.S. PATENT DOCUMENTS

| 6,319,921 | B1 | 11/2001 | Cirillo et al. |
| 6,358,945 | B1 | 3/2002 | Breitfelder et al. |
| 6,670,357 | B2 * | 12/2003 | Leftheris et al. ............ 514/218 |

FOREIGN PATENT DOCUMENTS

| WO | WO 00/25791 | 5/2000 |
| WO | WO 00/43384 | 7/2000 |
| WO | WO 01/30778 | 5/2001 |
| WO | WO 01/37837 | 5/2001 |

OTHER PUBLICATIONS

Branger, J., et al; Inhibition of coagulation, fibrinolysis and endothelial cell activation of a p38 mitogen-activated protein kinase inhibitor during human endotoxemia. Blood, Jun. 1, 2003, vol. 101, No. 11, pp. 4446-4448.

Murdoch, C., et al; Chemokine receptors and their role in inflammation and infectious diseases, Blood, vol. 95 No. 10 May 15, 2000 pp. 3032-3043.

Marin, V. et al; The p38 mitogen-activated protein kinase pathway plays a critical role in thrombin-induced endothelial chemokine production and leukocyte recruitment. Blood, Aug. 1, 2001, vol. 98, No. 3, pp. 667-673.

* cited by examiner

*Primary Examiner*—Herbert J. Lilling
(74) *Attorney, Agent, or Firm*—Michael Morris; Mary-Ellen M. Devlin; Anthony P. Bottino

(57) ABSTRACT

Disclosed are methods for a treating a disease or condition relating to blood coagulation and fibrinolysis using p38 MAP kinase inhibitors.

5 Claims, No Drawings

123
ANTICOAGULANT AND FIBRINOLYTIC THERAPY USING P38 MAP KINASE INHIBITORS

APPLICATION DATA

This application is a continuation of U.S. application Ser. No. 10/630,599 filed Jul. 30, 2003, now abandoned which claims benefit to U.S. provisional application Ser. No. 60/403,422 filed Aug. 14, 2002.

TECHNICAL FIELD OF THE INVENTION

The present invention relates to methods of using p38 kinase inhibitors in the treatment of diseases related to blood coagulation and fibrinolysis.

BACKGROUND OF THE INVENTION

Activation of the coagulation system is an important manifestation of the systemic inflammatory response of the host to infection. Levi M, et. al. 1999 *N Engl J Med.;* 341:586-592. Several in vivo models have been used to dissect the molecular mechanisms that contribute to coagulation activation by bacteria and bacterial products, including intravenous injection of low dose lipopolysaccharide (LPS) into healthy humans. Van der Poll T et. al., 1999 Cohen J, Marshall J, ed. *The Immune Response in the Critically Ill.* Berlin: Springer-Verlag; 335-357. Tissue factor, a glycoprotein expressed on endothelial cells and monocytes upon stimulation, plays an essential role in coagulation activation induced by LPS or bacteria in vivo, as demonstrated by abolishment of this response by inhibitors of tissue factor. de Jonge E, et. al., 2000 *Blood* 95:1124-1129; Creasey A A, et. al. 1993 *J Clin Invest.;* Carr C, et al. 1994 *Circ Shock.* 44:126-137; Levi M, et al. 1994 *J Clin Invest.* 93:114-120. Mitogen-activated protein kinases (MAPKs), such as p38 MAPK, participate in intracellular signaling cascades that mediate inflammatory responses to infectious and noninfectious stimuli. Herlaar E, et al. 1999 *Mol Med Today* 5:439-447; Ono K, et. al. 2000 *Cell Signal* 12:1-13. Recent in vitro studies have implicated one of these kinases, p38 MAPK, in the regulation of tissue factor expression on monocytes, endothelial cells, and smooth muscle cells. Chu A J, et al. 2001 *J Surg Res.* 101:85-90. Blum S, et al. 2001 *J Biol. Chem.* 276:33428-33434; Eto M, et. al. 2002 *Circulation* 105:1756-1759; Herkert O, et. al. 2002 *Circulation;* 105:2030-2036.

The p38 kinase inhibitors have been discussed in the literature and have been disclosed in U.S. Pat. Nos. 6,319,921, 6,358,945, 5,716,972, U.S. Pat. No. 5,686,455, U.S. Pat. No. 5,656,644, U.S. Pat. No. 5,593,992, U.S. Pat. No. 5,593,991, U.S. Pat. No. 5,663,334, U.S. Pat. No. 5,670,527, U.S. Pat. Nos. 5,559,137, 5,658,903, U.S. Pat. No. 5,739,143, U.S. Pat. No. 5,756,499, U.S. Pat. No. 6,277,989, U.S. Pat. No. 6,340,685, and U.S. Pat. No. 5,716,955; and PCT applications WO 92/12154, WO 94/19350, WO 95/09853, WO 95/09851, WO 95/09847, WO 95/09852, WO 97/25048, WO 97/25047, WO 97/33883, WO 97/35856, WO 97/35855, WO 97/36587, WO 97/47618, WO 97/16442, WO 97/16441, WO 97/12876, WO 98/25619, WO 98/06715, WO 98/07425, WO 98/28292, WO 98/56377, WO 98/07966, WO 98/56377, WO 98/22109, WO 98/24782, WO 98/24780, WO 98/22457, WO 98/52558, WO 98/52559, WO 98/52941, WO 98/52937, WO 98/52940, WO 98/56788, WO 98/27098, WO 98/47892, WO 98/47899, WO 98/50356, WO 98/32733, WO 99/58523, WO 99/01452, WO 99/01131, WO 99/01130, WO 99/01136, WO 99/17776, WO 99/32121, WO 99/58502, WO 99/58523, WO 99/57101, WO 99/61426, WO 99/59960, WO 99/59959, WO 99/00357, WO 99/03837, WO 99/01441, WO 99/01449, WO 99/03484, WO 99/15164, WO 99/32110, WO 99/32111, WO 99/32463, WO 99/64400, WO 99/43680, WO 99/17204, WO 99/25717, WO 99/50238, WO 99/61437, WO 99/61440, WO 00/26209, WO 00/18738, WO 00/17175, WO 00/20402, WO 00/01688, WO 00/07980, WO 00/07991, WO 00/06563, WO 00/12074, WO 00/12497, WO 00/31072, WO 00/31063, WO 00/23072, WO 00/31065, WO 00/35911, WO 00/39116, WO 00/43384, WO 00/41698, WO 00/69848, WO 00/26209, WO 00/63204, WO 00/07985, WO 00/59904, WO 00/71535, WO 00/10563, WO 00/25791, WO 00/55152, WO 00/55139, WO 00/17204, WO 00/36096, WO 00/55120, WO 00/55153, WO 00/56738, WO 01/21591, WO 01/29041, WO 01/29042, WO 01/62731, WO 01/05744, WO 01/05745, WO 01/05746, WO 01/05749, WO 01/05751, WO 01/27315, WO 01/42189, WO 01/00208, WO 01/42241, WO 01/34605, WO 01/47897, WO 01/64676, WO 01/37837, WO 01/38312, WO 01/38313, WO 01/36403, WO 01/38314, WO 01/47921, WO 01/27089, DE 19842833, and JP 2000 86657.

For the most part, such compounds have been indicated as being useful in treating cytokine mediated diseases such as those related to inflammation. Marin et al discusses the issue of whether p38 MAPK is involved in thrombin-induced endothelial proinflammatory functions including chemokine production. *Blood,* 1 Aug. 2001, Vol. 98 (3) 667-673. Until the present invention however, knowledge of the role of p38 MAPK in activation of coagulation and fibrinolysis has not been available.

SUMMARY OF THE INVENTION

In view of the work cited above there is a clear need for a method of treating diseases or conditions related to coagulation using small molecule inhibitors such as those which inhibit p38 MAP kinase.

It is therefore an object of the invention to provide a method of anticoagulatant and fibrinolytic therapy using inhibitors of p38 MAP kinase either for prevention or for treatment of these hematological physiologic processes in disease states where their activation may cause harm.

DETAILED DESCRIPTION OF THE PREFERRED EMBODIMENTS

Suprisingly, it has been found that p38 MAPK inhibitors possess inhibitory effects on the procoagulant and profibrinolytic responses during human endotoxemia. The invention therefore provides for a method of anticoagulant and fibrinolytic therapy for a disease or condition relating to blood coagulation or fibrinolysis comprising administering to a patient in need thereof a pharmaceutically effective a amount of a p38 MAP kinase inhibitor. This administration may be of benefit given either prophylactically to patients at risk or therapeutically for patients who have developed complications related to these pathways.

The p38 kinase inhibitors within the scope of the present invention the are compounds chosen from those disclosed in U.S. Pat. Nos. 6,319,921, 6,358,945, 5,716,972, U.S. Pat. No. 5,686,455, U.S. Pat. No. 5,656,644, U.S. Pat. No. 5,593,992, U.S. Pat. No. 5,593,991, U.S. Pat. No. 5,663,334, U.S. Pat. No. 5,670,527, U.S. Pat. No. 5,559,137, 5,658,903, U.S. Pat. No. 5,739,143, U.S. Pat. No. 5,756,499, U.S. Pat. No. 6,277,989, U.S. Pat. No. 6,340,685, and U.S. Pat. No. 5,716,955; and PCT applications WO 92/12154, WO 94/19350, WO 95/09853, WO 95/09851, WO 95/09847, WO 95/09852, WO 97/25048, WO 97/25047, WO 97/33883, WO 97/35856, WO 97/35855, WO 97/36587, WO 97/47618, WO 97/16442, WO 97/16441, WO 97/12876, WO 98/25619, WO 98/06715, WO 98/07425, WO 98/28292, WO 98/56377, WO 98/07966, WO 98/56377, WO 98/22109, WO 98/24782, WO 98/24780, WO 98/22457, WO 98/52558, WO 98/52559, WO 98/52941, WO 98/52937, WO 98/52940, WO 98/56788, WO 98/27098, WO 98/47892, WO 98/47899, WO 98/50356, WO 98/32733, WO 99/58523, WO 99/01452, WO 99/01131, WO 99/01130, WO 99/01136, WO 99/17776, WO 99/32121, WO 99/58502, WO 99/58523, WO 99/57101, WO 99/61426, WO 99/59960, WO 99/59959, WO 99/00357, WO 99/03837, WO 99/01441, WO 99/01449, WO 99/03484, WO 99/15164, WO 99/32110, WO 99/32111, WO 99/32463, WO 99/64400, WO 99/43680, WO 99/17204, WO 99/25717, WO 99/50238, WO 99/61437, WO 99/61440, WO 00/26209, WO 00/18738, WO 00/17175, WO 00/20402, WO 00/01688, WO 00/07980, WO 00/07991, WO 00/06563, WO 00/12074, WO 00/12497, WO 00/31072, WO 00/31063, WO 00/23072, WO 00/31065, WO 00/35911, WO 00/39116, WO 00/43384, WO 00/41698, WO 00/69848, WO 00/26209, WO 00/63204, WO 00/07985, WO 00/59904, WO 00/71535, WO 00/10563, WO 00/25791, WO 00/55152, WO 00/55139, WO 00/17204, WO 00/36096, WO 00/55120, WO 00/55153, WO 00/56738, WO 01/21591, WO 01/29041, WO 01/29042, WO 01/62731, WO 01/05744, WO 01/05745, WO 01/05746, WO 01/05749, WO 01/05751, WO 01/27315, WO 01/42189, WO 01/00208, WO 01/42241, WO 01/34605, WO 01/47897, WO 01/64676, WO 01/37837, WO 01/38312, WO 01/38313, WO 01/36403, WO 01/38314, WO 01/47921, WO 01/27089, DE 19842833, and JP 2000 86657 whose disclosures are all incorporated herein by reference in their entirety.

Of particular interest are those p38 inhibitors disclosed in U.S. Pat. Nos. 6,319,921, 6,358,945, U.S. Pat. No. 6,277, 989, U.S. Pat. No. 6,340,685, WO 00/12074, WO 00/12497, WO 00/59904, WO 00/71535, WO 01/64676, WO 99/61426, WO 00/10563, WO 00/25791, WO 01/37837, WO 01/38312, WO 01/38313, WO 01/38314, WO 01/47921, WO 99/61437, WO 99/61440, WO 00/17175, WO 00/17204, WO 00/36096, WO 98/27098, WO 99/00357, WO 99/58502, WO 99/64400, WO 99/01131, WO 00/43384, WO 00/55152, WO 00/55139 and WO 01/36403.

In a preferred embodiment the invention provides a method of anticoagulant and fibrinolytic therapy for a disease or condition relating to blood coagulation or fibrinolysis comprising administering to a patient in need thereof a pharmaceutically effective a amount of a p38 MAP kinase inhibitor chosen from the compounds of formula disclosed in WO 00/43384 and corresponding U.S. Pat. No. 6,319, 921:

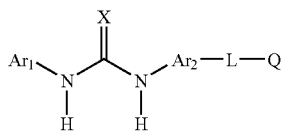

wherein $Ar_1$ is a heterocyclic group selected from the group consisting of pyrrole, pyrrolidine, pyrazole, imidazole, oxazole, thiazole, furan and thiophene; and wherein $Ar_1$ may be substituted by one or more $R_1$, $R_2$ or $R_3$;

$Ar_2$ is phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three $R_2$ groups;

L, a linking group, is a $C_{1-10}$ saturated or unsaturated branched or unbranched carbon chain;

wherein one or more methylene groups are optionally independently replaced by O, N or S; and wherein said linking group is optionally substituted with 0-2 oxo groups and one or more $C_{1-4}$ branched or unbranched alkyl which may be substituted by one or more halogen atoms;

Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

c) $C_{1-6}$ alkoxy, secondary or tertiary amine wherein the amino nitrogen is covalently bonded to groups selected from the group consisting of $C_{1-3}$ alkyl, $C_{1-5}$ alkoxy-alkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

$R_1$ is selected from the group consisting of:

(a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, C$_{1-3}$ alkyloxy which is optionally partially or fully halogenated, NH$_2$C(O) and di(C$_{1-3}$)alkylaminocarbonyl;
(b) C$_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three C$_{1-3}$alkyl groups, or an analog of such cycloalkyl group wherein one to three ring methylene groups are replaced by groups independently selected from O, S, CHOH, >C=O, >C=S and NH;
(c) C$_{3-10}$ branched alkenyl which may optionally be partially or fully halogenated, and which is optionally substituted with one to three C$_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, C$_{1-3}$ alkyloxy which is optionally partially or fully halogenated, NH$_2$C(O), mono- or di(C$_{1-3}$)alkylaminocarbonyl;
(d) C$_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three C$_{1-3}$ alkyl groups;
(e) cyano; and,
(f) methoxycarbonyl, ethoxycarbonyl and propoxycarbonyl;

R$_2$ is selected from the group consisting of:
a C$_{1-6}$ branched or unbranched alkyl which may optionally be partially or fully halogenated, acetyl, aroyl, C$_{1-4}$ branched or unbranched alkoxy, which may optionally be partially or fully halogenated, halogen, methoxycarbonyl and phenylsulfonyl;

R$_3$ is selected from the group consisting of:
a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl; wherein such phenyl, naphthyl or heterocyclic group is optionally substituted with one to five groups selected from the group consisting of a C$_{1-6}$ branched or unbranched alkyl, phenyl, naphthyl, heterocycle selected from the group hereinabove described, C$_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, halo, hydroxy, cyano, C$_{1-3}$ alkyloxy which may optionally be partially or fully halogenated, phenyloxy, naphthyloxy, heteraryloxy wherein the heterocyclic moiety is selected from the group hereinabove described, nitro, amino, mono- or di-(C$_{1-3}$)alkylamino, phenylamino, naphthylamino, heterocyclylamino wherein the heterocyclyl moiety is selected from the group hereinabove described, NH$_2$C(O), a mono- or di-(C$_{1-3}$)alkyl aminocarbonyl, C$_{1-5}$ alkyl-C(O)—C$_{1-4}$ alkyl, amino-C$_{1-5}$ alkyl, mono- or di-(C$_{1-3}$)alkylamino-C$_{1-5}$ alkyl, amino-S(O)$_2$, di-(C$_{1-3}$)alkylamino-S(O)$_2$, R$_4$—C$_{1-5}$ alkyl, R$_5$—C$_{1-5}$ alkoxy, R$_6$—C(O)—C$_{1-5}$ alkyl and R$_7$—C$_{1-5}$ alkyl(R$_8$)N;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, C$_{1-6}$ branched or unbranched alkyl which is optionally partially or fully halogenated, halo, cyano, C$_{1-3}$ alkyloxy which is optionally partially or fully halogenated, phenyloxy, naphthyloxy, heterocyclyloxy wherein the heterocyclyl moiety is selected from the group hereinabove described, nitro, amino, mono- or di-(C$_{1-3}$)alkylamino, phenylamino, naphthylamino, heterocyclylamino wherein the heterocyclyl moiety is selected from the group hereinabove described, NH$_2$C(O), a mono- or di-(C$_{1-3}$)alkyl aminocarbonyl, C$_{1-4}$ alkyl-OC(O), C$_{1-5}$ alkyl-C(O)—C$_{1-4}$ branched or unbranched alkyl, an amino-C$_{1-5}$ alkyl, mono- or di-(C$_{1-3}$)alkylamino-C$_{1-5}$ alkyl, R$_9$—C$_{1-5}$ alkyl, R$_{10}$—C$_{1-5}$ alkoxy, R$_{11}$—C(O)—C$_{1-5}$ alkyl, and R$_{12}$—C$_{1-5}$ alkyl(R$_{13}$)N;

c) cycloalkyl selected from the group consisting of cyclopentanyl, cyclohexanyl, cycloheptanyl, bicyclopentanyl, bicyclohexanyl and bicycloheptanyl, which the cycloalkyl may optionally be partially or fully halogenated and which may optionally be substituted with one to three C$_{1-3}$ alkyl groups;

d) C$_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three C$_{1-3}$ alkyl groups; and e) acetyl, aroyl, alkoxycarbonylalkyl or phenylsulfonyl;

f) C$_{1-6}$ branched or unbranched alkyl which may optionally be partially or fully halogenated;

or R$_1$ and R$_2$ taken together may optionally form a fused phenyl or pyridinyl ring, and wherein each R$_8$, R$_{13}$ is independently selected from the group consisting of:
hydrogen and C$_{1-4}$ branched or unbranched alkyl which may optionally be partially or fully halogenated;

each $R_4$, $R_5$, $R_6$, $R_7$, $R_9$, $R_{10}$, $R_{11}$ and $R_{12}$ is independently selected from the group consisting of:
morpholine, piperidine, piperazine, imidazole and tetrazole;
m=0, 1, 2;
r=0, 1, 2;
t=0, 1, 2;
X=O or S and physiologically acceptable acids or salts thereof.

In a preferred embodiment the p38 kinase inhibitor is selected from the compounds as immediately described above and wherein $Ar_2$ is naphthyl, tetrahydronaphthyl, indanyl or indenyl.

In a more preferred subgeneric aspect of the invention the p38 kinase inhibitor is selected from the compounds as immediately described above and wherein $AR_2$ is naphthyl.

A yet more preferred subgeneric aspect of the invention the p38 kinase inhibitor is selected from the compounds as immediately described above and wherein:
$Ar_1$ is thiophene or pyrazole;
$AR_2$ is 1-naphthyl;
L is $C_{1-6}$ saturated or unsaturated branched or unbranched carbon chain wherein one or more methylene groups are optionally independently replaced by O, N or S; and
wherein said linking group is optionally substituted with 0-2 oxo groups and one or more $C_{1-4}$ branched or unbranched alkyl which may be substituted by one or more halogen atoms;
$R_1$ is selected from the group consisting of $C_{1-4}$alkyl branched or unbranched, cyclopropyl and cyclohexyl which may optionally be partially or fully halogenated and which may optionally be substituted with one to three $C_{1-3}$alkyl groups;
$R_3$ is selected from the group consisting of $C_{3-10}$alkyl branched or unbranched, cyclopropanyl, cyclopentanyl, phenyl, pyridinyl each being optionally substituted as described above and alkoxycarbonylalkyl.

In a yet further preferred subgeneric aspect of the invention the p38 kinase inhibitor is selected from the compounds as immediately described above and wherein $Ar_1$ is pyrazole.

A still yet further preferred subgeneric aspect of previous the invention the p38 kinase inhibitor is selected from the compounds as immediately described above and wherein L is $C_{1-5}$ saturated carbon chain wherein one or more methylene groups are optionally independently replaced by O, N or S; and wherein said linking group is optionally substituted with 0-2 oxo groups and one or more $C_{1-4}$ branched or unbranched alkyl which may be substituted by one or more halogen atoms.

Particularly preferred embodiments of L are propoxy, ethoxy, methoxy, methyl, propyl, $C_{3-5}$ acetylene or methylamino each being optionally substituted are described herein.

A more particularly preferred embodiment of L is ethoxy optionally substituted.

The following compounds are representative of the compounds the p38 kinase inhibitors which can be used in the methods described herein:
1-[5-tert-Butyl-2-p-tolyl-2H-pyrazol-3-yl]-3-[4-(2-morpholin-4-yl-ethoxy)naphthalen-1-yl]-urea;
1-[5-tert-Butyl-2-p-tolyl-2H-pyrazol-3-yl]-3-[4-(2-(cis-2,6-dimethylmorpholin-4-yl)ethoxy)naphthalen-1-yl]-urea;
1-[5-tert-Butyl-2-p-tolyl-2H-pyrazol-3-yl]-3-[4-(2-(trans-2,6-dimethylmorpholin-4-yl)ethoxy)naphthalen-1-yl]-urea;
1-[5-tert-Butyl-2-p-tolyl-2H-pyrazol-3-yl]-3-[4-(2-(2-(methoxymethyl)morpholin-4-yl)ethoxy)naphthalen-1-yl]-urea;
1-[5-tert-Butyl-2-p-tolyl-2H-pyrazol-3-yl]-3-[4-(2-(morpholin-4-yl)-2-oxoethoxy)naphthalen-1-yl]-urea;
1-[5-tert-Butyl-2-p-tolyl-2H-pyrazol-3-yl]-3-[4-(2-(morpholin-4-yl)-2-methylethoxy)naphthalen-1-yl]-urea;
1-[5-tert-Butyl-2-p-tolyl-2H-pyrazol-3-yl]-3-[4-(2-(morpholin-4-yl)-1-methylethoxy)naphthalen-1-yl]-urea;
1-[5-tert-Butyl-2-p-tolyl-2H-pyrazol-3-yl]-3-[4-(2-thiomorpholin-4-yl-ethoxy)naphthalen-1-yl]-urea;
1-[5-tert-Butyl-2-p-tolyl-2H-pyrazol-3-yl]-3-[4-(2-(1-oxothiomorpholin-4-yl)ethoxy)naphthalen-1-yl]-urea;
1-[5-tert-Butyl-2-p-tolyl-2H-pyrazol-3-yl]-3-[4-(2-morpholin-4-yl-ethoxy)-3-methylnaphthalen-1-yl]-urea;
1-[5-tert-Butyl-2-p-tolyl-2H-pyrazol-3-yl]-3-[4-(2-piperidin-4-yl-ethoxy)naphthalen-1-yl]-urea;
1-[5-tert-Butyl-2-p-tolyl-2H-pyrazol-3-yl]-3-[4-(2-(1-acetylpiperidin-4-yl)ethoxy)naphthalen-1-yl]-urea;
1-[5-tert-Butyl-2-p-tolyl-2H-pyrazol-3-yl]-3-[4-(2-thiazolidin-3-yl-ethoxy)naphthalen-1-yl]-urea;
1-[5-tert-Butyl-2-p-tolyl-2H-pyrazol-3-yl]-3-[4-(2-(morpholin-4-yl-carbonyloxo)ethoxy)naphthalen-1-yl]-urea;
1-[5-tert-Butyl-2-p-tolyl-2H-pyrazol-3-yl]-3-[4-(2-(tetrahydropyran-4-yl)ethoxy)naphthalen-1-yl]-urea;
1-[5-tert-Butyl-2-p-tolyl-2H-pyrazol-3-yl]-3-[4-(2-(N-methyl-2-methoxyethylamino)ethoxy)naphthalen-1-yl]-urea;
1-[5-tert-Butyl-2-p-tolyl-2H-pyrazol-3-yl]-3-[4-(2-(1-oxotetrahydrothiophen-3-yl)ethoxy)naphthalen-1-yl]-urea;
1-[5-tert-Butyl-2-p-tolyl-2H-pyrazol-3-yl]-3-[4-(3-morpholin-4-yl-propyl)naphthalen-1-yl]-urea;
1-[5-tert-Butyl-2-p-tolyl-2H-pyrazol-3-yl]-3-[4-(morpholin-4-yl-methyl)naphthalen-1-yl]-urea;
1-[5-tert-Butyl-2-p-tolyl-2H-pyrazol-3-yl]-3-[4-(3-thiazolidin-3-yl-propyl)naphthalen-1-yl]-urea;
1-[5-tert-Butyl-2-p-tolyl-2H-pyrazol-3-yl]-3-[4-(3-(tetrahydopyran-2-yl-oxy)propyl)naphthalen-1-yl]-urea;
1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(2-pyridin-4-yl-ethenyl)naphthalen-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(methoxymethyloxy)propyn-1-yl)naphthalen-1-yl]-urea;
1-[5-tert-Butyl-2-p-tolyl-2H-pyrazol-3-yl]-3-[4-(3-(morpholin-4-yl)-3-methylpropyn-1-yl)naphthalen-1-yl]-urea;
1-[5-tert-Butyl-2-p-tolyl-2H-pyrazol-3-yl]-3-[4-(3-(morpholin-4-yl)-3,3-dimethylpropyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(furan-2-ylcarbonyloxy)propyn-1-yl)naphthalen-1-yl]-urea;
1-[5-tert-Butyl-2-p-tolyl-2H-pyrazol-3-yl]-3-[4-(3-(piperidin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;

1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-benzimidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)-ethoxy)naphthalen-1-yl]-urea;
1-[5-tert-Butyl-2-p-tolyl-2H-pyrazol-3-yl]-3-[4-(pyridin-4-yl-methylamino)naphthalen-1-yl]-urea;
1-[5-tert-Butyl-2-p-tolyl-2H-pyrazol-3-yl]-3-[4-(pyridin-4-yl-carbonylamino)naphthalen-1-yl]-urea;
1-[5-tert-Butyl-2-p-tolyl-2H-pyrazol-3-yl]-3-[4-(morpholin-4-yl-acetamido)naphthalen-1-yl]-urea;
1-[5-tert-Butyl-2-p-tolyl-2H-pyrazol-3-yl]-3-[4-(pyridin-3-yl-methylamino)naphthalen-1-yl]-urea;
1-[5-tert-Butyl-2-p-tolyl-2H-pyrazol-3-yl]-3-[4-(pyridin-3-yl-carbonylamino)naphthalen-1-yl]-urea;
1-[5-iso-Propyl-2-phenyl-2H-pyrazol-3-yl]-3-[4-(2-morpholin-4-yl-ethoxy)naphthalen-1-yl]-urea;
1-[5-(Tetrahydropyran-3-yl)-2-phenyl-2H-pyrazol-3-yl]-3-[4-(2-morpholin-4-yl-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl]-3-[4-(2-morpholin-4-yl-ethoxy)naphthalen-1-yl]-urea;
1-[5-ethoxycarbonyl-2-phenyl-2H-pyrazol-3-yl]-3-[4-(2-morpholin-4-yl-ethoxy)naphthalen-1-yl]-urea;
1-[5-(1-methylcyclohex-1-yl)-2-phenyl-2H-pyrazol-3-yl]-3-[4-(2-morpholin-4-yl-ethoxy)naphthalen-1-yl]-urea;
1-[5-tert-butyl-2-methyl-2H-pyrazol-3-yl]-3-[4-(2-morpholin-4-yl-ethoxy)naphthalen-1-yl]-urea;
1-[5-tert-butyl-2-benzyl-2H-pyrazol-3-yl]-3-[4-(2-morpholin-4-yl-ethoxy)naphthalen-1-yl]-urea;
1-[5-tert-butyl-2-(4-chlorophenyl)-2H-pyrazol-3-yl]-3-[4-(2-morpholin-4-yl-ethoxy)naphthalen-1-yl]-urea;
1-[5-tert-butyl-2-butyl-2H-pyrazol-3-yl]-3-[4-(2-morpholin-4-yl-ethoxy)naphthalen-1-yl]-urea;
1-[5-tert-butyl-2-(ethoxycarbonylmethyl)-2H-pyrazol-3-yl]-3-[4-(2-morpholin-4-yl-ethoxy)naphthalen-1-yl]-urea;
1-[5-tert-butyl-2-(4-methyl-3-carbamylphenyl)-2H-pyrazol-3-yl]-3-[4-(2-morpholin-4-yl-ethoxy)naphthalen-1-yl]-urea;
1-[5-tert-butyl-2-(4-methyl-3-(2-ethoxycarbonylvinyl)phenyl)-2H-pyrazol-3-yl]-3-[4-(2-morpholin-4-yl-ethoxy)naphthalen-1-yl]-urea;
1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;
1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;
1-[5-tert-butyl-2-(3-(2-morpholin-4-yl-ethyl)phenyl)-2H-pyrazol-3-yl]-3-[4-(2-morpholin-4-yl-ethoxy)naphthalen-1-yl]-urea;
1-[5-tert-butyl-2-(3-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(3-dimethylaminomethylphenyl)-2H-pyrazol-3-yl]-3-[4-(2-morpholin-4-yl-ethoxy)naphthalen-1-yl]-urea;
1-[5-tert-butyl-2-(4-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(4-(3-benzylureido)phenyl)-2H-pyrazol-3-yl]-3-[4-(2-morpholin-4-yl-ethoxy)naphthalen-1-yl]-urea;
1-[5-tert-butyl-2-(2-chloropyridin-5-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-morpholin-4-yl-ethoxy)naphthalen-1-yl]-urea;
1-[5-tert-butyl-2-(2-methoxypyridin-5-yl)-2H-pyrazol-3-yl]-3-[4-(2-morpholin-4-yl-ethoxy)naphthalen-1-yl]-urea;
1-[5-tert-butyl-2-(pyridin-3-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-pyridin-4-yl-ethoxy)naphthalen-1-yl]-urea;
1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;
1-[5-tert-butyl-2-(2-methylpyridin-5-yl)-2H-pyrazol-3-yl]-3-[4-(3-morpholin-4-yl-propyn-1-yl)naphthalen-1-yl]-urea;
1-[5-tert-Butyl-2-p-tolyl-2H-pyrazol-3-yl]-3-[4-(2-(2-dimethylaminomethylmorpholin-4-yl)ethoxy)naphthalen-1-yl]-urea;
1-[5-tert-butyl-2-iso-propyl-2H-pyrazol-3-yl]-3-[4-(2-morpholin-4-yl-ethoxy)naphthalen-1-yl]-urea;
1-[5-tert-butyl-2-cyclopropyl-2H-pyrazol-3-yl]-3-[4-(2-morpholin-4-yl-ethoxy)naphthalen-1-yl]-urea;
1-[5-tert-butyl-2-(thiophen-3-yl)-2H-pyrazol-3-yl]-3-[4-(2-morpholin-4-yl-ethoxy)naphthalen-1-yl]-urea;
1-[5-tert-butyl-2-cyclopentyl-2H-pyrazol-3-yl]-3-[4-(2-morpholin-4-yl-ethoxy)naphthalen-1-yl]-urea;
1-[5-tert-butyl-2-iso-propyl-2H-pyrazol-3-yl]-3-[4-(tetrahydropyran-4-yl-ethoxy)naphthalen-1-yl]-urea;
1-[5-tert-butyl-2-cyclopropyl-2H-pyrazol-3-yl]-3-[4-(1-oxo-tetrahydrothiophen-3-yl-ethoxy)naphthalen-1-yl]-urea;
1-[5-tert-butyl-2-(thiophen-3-yl)-2H-pyrazol-3-yl]-3-[4-(2-pyridinyl-4-yl-ethoxy)naphthalen-1-yl]-urea;
1-[5-tert-butyl-2-cyclopentyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(3-(pyridin-4-yl)propyn-1-yl)naphthalen-1-yl]-urea;
1-[5-tert-Butyl-2-p-tolyl-2H-pyrazol-3-yl]-3-[4-(3-(2-methylaminopyridin-4-yl)propyn-1-yl)naphthalen-1-yl]-urea;
1-[5-tert-Butyl-2-p-tolyl-2H-pyrazol-3-yl]-3-[4-(3-(1-oxotetrahydothiophen-3-yl)propyn-1-yl)naphthalen-1-yl]-urea;
1-[5-tert-Butyl-2-p-tolyl-2H-pyrazol-3-yl]-3-[4-(3-(thiazolidin-3-yl)propyn-1-yl)naphthalen-1-yl]-urea;
1-[5-tert-Butyl-2-p-tolyl-2H-pyrazol-3-yl]-3-[4-(3-(tetrahydropyran-4-yl)propyn-1-yl)naphthalen-1-yl]-urea;
1-[5-tert-Butyl-2-p-tolyl-2H-pyrazol-3-yl]-3-[4-(2-methylaminopyrimidin-4-yl-methoxy)naphthalen-1-yl]-urea;
1-[5-tert-Butyl-2-p-tolyl-2H-pyrazol-3-yl]-3-[4-(2-(2-methylaminopyrimidin-4-yl)ethoxy)naphthalen-1-yl]-urea;
1-[5-tert-Butyl-2-p-tolyl-2H-pyrazol-3-yl]-3-[4-(2-(4-methoxybenzimidazol-1-yl)ethoxy)naphthalen-1-yl]-urea;
1-[5-tert-Butyl-2-p-tolyl-2H-pyrazol-3-yl]-3-[4-(2-(4-methylaminobenzimidazol-1-yl)ethoxy)naphthalen-1-yl]-urea;
1-[5-tert-Butyl-2-p-tolyl-2H-pyrazol-3-yl]-3-[4-(2-(2-imidazo[4,5-b]pyridin-1-yl)ethoxy)naphthalen-1-yl]-urea;
1-[5-tert-Butyl-2-p-tolyl-2H-pyrazol-3-yl]-3-[4-(2-[1,8]naphthyridin-4-yl)ethoxy)naphthalen-1-yl]-urea;

1-[5-tert-Butyl-2-p-tolyl-2H-pyrazol-3-yl]-3-[4-(2-(3,4-di-hydro-2H-pyrano[2,3-b]pyridin-5-yl)ethoxy)naphthalen-1-yl]-urea;

1-[5-tert-Butyl-2-pyridin-3-yl-2H-pyrazol-3-yl]-3-[4-(2-methylaminopyrimidin-4-yl-methoxy)naphthalen-1-yl]-urea;

1-[5-tert-Butyl-2-(2-methylpyridin-5-yl)-2H-pyrazol-3-yl]-3-[4-(2-(2-methylaminopyrimidin-4-yl)ethoxy)naphthalen-1-yl]-urea;

1-[5-tert-Butyl-2-(2-methylpyridin-5-yl)-2H-pyrazol-3-yl]-3-[4-(2-(4-methoxybenzimidazol-1-yl)ethoxy)naphthalen-1-yl]-urea;

1-[5-tert-Butyl-2-(2-methylpyridin-5-yl)-2H-pyrazol-3-yl]-3-[4-(2-(4-methylaminobenzimidazol-1-yl)ethoxy)naphthalen-1-yl]-urea;

1-[5-tert-Butyl-2-(2-methylpyridin-5-yl)-2H-pyrazol-3-yl]-3-[4-(2-(2-imidazo[4,5-b]pyridin-1-yl)ethoxy)naphthalen-1-yl]-urea;

1-[5-tert-Butyl-2-(2-methylpyridin-5-yl)-2H-pyrazol-3-yl]-3-[4-(2-[1, 8]naphthyridin-4-yl)ethoxy)naphthalen-1-yl]-urea;

1-[5-tert-Butyl-2-(2-methylpyridin-5-yl)-2H-pyrazol-3-yl]-3-[4-(2-(3,4-dihydro-2H-pyrano[2,3-b]pyridin-5-yl)ethoxy)naphthalen-1-yl]-urea;

1-[5-tert-Butyl-2-cyclopropyl-2H-pyrazol-3-yl]-3-[4-(2-methylaminopyrimidin-4-yl-methoxy)naphthalen-1-yl]-urea;

1-[5-tert-Butyl-2-cyclopropyl-2H-pyrazol-3-yl]-3-[4-(2-(2-methylaminopyrimidin-4-yl)ethoxy)naphthalen-1-yl]-urea;

1-[5-tert-Butyl-2-cyclopropyl-2H-pyrazol-3-yl]-3-[4-(2-(4-methoxybenzimidazol-1-yl)ethoxy)naphthalen-1-yl]-urea;

1-[5-tert-Butyl-2-cyclopropyl-2H-pyrazol-3-yl]-3-[4-(2-(4-methylaminobenzimidazol-1-yl)ethoxy)naphthalen-1-yl]-urea;

1-[5-tert-Butyl-2-methyl-2H-pyrazol-3-yl]-3-[4-(2-(2-imidazo[4,5-b]pyridin-1-yl)ethoxy)naphthalen-1-yl]-urea;

1-[5-tert-Butyl-2-methyl-2H-pyrazol-3-yl]-3-[4-(2-[1,8]naphthyridin-4-yl)ethoxy)naphthalen-1-yl]-urea;

1-[5-tert-Butyl-2-methyl-2H-pyrazol-3-yl]-3-[4-(2-(3,4-dihydro-2H-pyrano[2,3-b]pyridin-5-yl)ethoxy)naphthalen-1-yl]-urea and their physiologically acceptable acids or salts thereof.

The following compounds are preferred p38 kinase inhibitors which can be used in the methods described herein:

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(cis-2,6-dimethylmorpholin-4-yl)ethoxy)naphthalen-1-yl]-urea;

1-[5-tert-Butyl-2-p-tolyl-2H-pyrazol-3-yl]-3-[4-(2-(trans-2,6-dimethylmorpholin-4-yl)ethoxy)naphthalen-1-yl]-urea;

1-[5-tert-Butyl-2-p-tolyl-2H-pyrazol-3-yl]-3-[4-(2-(2-(methoxymethyl)morpholin-4-yl)ethoxy)naphthalen-1-yl]-urea;

1-[5-tert-Butyl-2-p-tolyl-2H-pyrazol-3-yl]-3-[4-(2-(morpholin-4-yl)-2-oxoethoxy)naphthalen-1-yl]-urea;

1-[5-tert-Butyl-2-p-tolyl-2H-pyrazol-3-yl]-3-[4-(2-(morpholin-4-yl)-2-methylethoxy)naphthalen-1-yl]-urea;

1-[5-tert-Butyl-2-p-tolyl-2H-pyrazol-3-yl]-3-[4-(2-(morpholin-4-yl)-1-methylethoxy)naphthalen-1-yl]-urea;

1-[5-tert-Butyl-2-p-tolyl-2H-pyrazol-3-yl]-3-[4-(2-thiomorpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-Butyl-2-p-tolyl-2H-pyrazol-3-yl]-3-[4-(2-morpholin-4-yl-ethoxy)-3-methylnaphthalen-1-yl]-urea;

1-[5-tert-Butyl-2-p-tolyl-2H-pyrazol-3-yl]-3-[4-(2-(morpholin-4-yl-carbonyloxo)ethoxy)naphthalen-1-yl]-urea;

1-[5-tert-Butyl-2-p-tolyl-2H-pyrazol-3-yl]-3-[4-(2-(tetrahydropyran-4-yl)ethoxy)naphthalen-1-yl]-urea;

1-[5-tert-Butyl-2-p-tolyl-2H-pyrazol-3-yl]-3-[4-(2-(1-oxotetrahydrothiophen-3-yl)ethoxy)naphthalen-1-yl]-urea;

1-[5-tert-Butyl-2-p-tolyl-2H-pyrazol-3-yl]-3-[4-(3-morpholin-4-yl-propyl)naphthalen-1-yl]-urea;

1-[5-tert-Butyl-2-p-tolyl-2H-pyrazol-3-yl]-3-[4-(morpholin-4-yl-methyl)naphthalen-1-yl]-urea;

1-[5-tert-Butyl-2-p-tolyl-2H-pyrazol-3-yl]-3-[4-(2-pyridin-4-yl-ethyl)naphthalen-1-yl]-urea;

1-[5-tert-Butyl-2-p-tolyl-2H-pyrazol-3-yl]-3-[4-(3-(morpholin-4-yl)propyn-1-yl)naphthalen-1-yl]-urea;

1-[5-tert-Butyl-2-p-tolyl-2H-pyrazol-3-yl]-3-[4-(3-(tetrahydropyran-2-yl-oxy)propyn-1-yl)naphthalen-1-yl]-urea;

1-[5-tert-Butyl-2-p-tolyl-2H-pyrazol-3-yl]-3-[4-(3-(tetrahydropyran-2-yl-oxy)butyn-1-yl)naphthalen-1-yl]-urea;

1-[5-tert-Butyl-2-p-tolyl-2H-pyrazol-3-yl]-3-[4-(3-(piperdin-1-yl)propyn-1-yl)naphthalen-1-yl]-urea;

1-[5-tert-Butyl-2-p-tolyl-2H-pyrazol-3-yl]-3-[4-(3-(2-methoxymethylmorpholin-4-yl)propyn-1-yl)naphthalen-1-yl]-urea;

1-[5-tert-Butyl-2-p-tolyl-2H-pyrazol-3-yl]-3-[4-(pyridin-4-yl-methoxy)naphthalen-1-yl]-urea;

1-[5-tert-Butyl-2-p-tolyl-2H-pyrazol-3-yl]-3-[4-(2-pyridin-4-yl-ethoxy)naphthalen-1-yl]-urea;

1-[5-tert-Butyl-2-p-tolyl-2H-pyrazol-3-yl]-3-[4-(3-pyridin-4-yl-propoxy)naphthalen-1-yl]-urea;

1-[5-tert-Butyl-2-p-tolyl-2H-pyrazol-3-yl]-3-[4-(2-imidazol-1-yl-ethoxy)naphthalen-1-yl]-urea;

1-[5-tert-Butyl-2-p-tolyl-2H-pyrazol-3-yl]-3-[4-(2-(3,4-dimethoxyphenyl)-ethoxy)naphthalen-1-yl]-urea;

1-[5-tert-Butyl-2-p-tolyl-2H-pyrazol-3-yl]-3-[4-(pyridin-4-yl-methylamino)naphthalen-1-yl]-urea;

1-[5-iso-Propyl-2-phenyl-2H-pyrazol-3-yl]-3-[4-(2-morpholin-4-yl-ethoxy)naphthalen-1-yl]-urea;

1-[5-cyclohexyl-2-phenyl-2H-pyrazol-3-yl]-3-[4-(2-morpholin-4-yl-ethoxy)naphthalen-1-yl]-urea;

1-[5-(2,2,2-trifluoroethyl)-2-phenyl-2H-pyrazol-3-yl]-3-[4-(2-morpholin-4-yl-ethoxy)naphthalen-1-yl]-urea;

1-[5-(1-methylcycloprop-1-yl)-2-phenyl-2H-pyrazol-3-yl]-3-[4-(2-morpholin-4-yl-ethoxy)naphthalen-1-yl]-urea;

1-[5-(1-methylcyclohex-1-yl)-2-phenyl-2H-pyrazol-3-yl]-3-[4-(2-morpholin-4-yl-ethoxy)naphthalen-1-yl]-urea;

1-[5-tert-butyl-2-methyl-2H-pyrazol-3-yl]-3-[4-(2-morpholin-4-yl-ethoxy)naphthalen-1-yl]-urea;

1-[5-tert-butyl-2-(4-chlorophenyl)-2H-pyrazol-3-yl]-3-[4-(2-morpholin-4-yl-ethoxy)naphthalen-1-yl]-urea;

1-[5-tert-butyl-2-butyl-2H-pyrazol-3-yl]-3-[4-(2-morpholin-4-yl-ethoxy)naphthalen-1-yl]-urea;

1-[5-tert-butyl-2-(4-methyl-3-carbamylphenyl)-2H-pyrazol-3-yl]-3-[4-(2-morpholin-4-yl-ethoxy)naphthalen-1-yl]-urea;

1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;

1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;

1-[5-tert-butyl-2-(3-dimethylaminomethylphenyl)-2H-pyrazol-3-yl]-3-[4-(2-morpholin-4-yl-ethoxy)naphthalen-1-yl]-urea;

1-[5-tert-butyl-2-(2-chloropyridin-5-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-morpholin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea;

1-[5-tert-butyl-2-(pyridin-3-yl)-2H-pyrazol-3-yl]-3-[4-(2-morpholin-4-yl-ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;

1-[5-tert-butyl-2-(2-methylpyridin-5-yl)-2H-pyrazol-3-yl]-3-[4-(3-morpholin-4-yl-propyn-1-yl)naphthalen-1-yl]-urea.

Particularly preferred p38 kinase inhibitors within the scope of the present invention are the following compounds:

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea or 1-[5-tert-butyl-2-methyl-2H-pyrazol-3-yl]-3-[4-(2-morpholin-4-yl-ethoxy)naphthalen-1-yl]-urea.

In another preferred embodiment the invention provides a method of anticoagulant and fibrinolytic therapy for a disease or condition relating to blood coagulation or fibrinolysis comprising administering to a patient in need thereof a pharmaceutically effective a amount of a p38 MAP kinase inhibitor chosen from the compounds of formula disclosed in WO 00/55139 and corresponding U.S. Pat. No. 6,358,945:

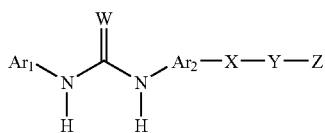

(I)

wherein:

$Ar_1$ is selected from the group consisting of: pyrrole, pyrrolidine, pyrazole, imidazole, oxazole, thiazole, furan and thiophene;

wherein $Ar_1$ may be substituted by one or more $R_1$, $R_2$ or $R_3$;

$Ar_2$ is:
  phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with zero to three $R_2$ groups;

X is:
  a) a $C_{5-8}$ cycloalkyl or cycloalkenyl optionally substituted with 0-2 oxo groups or 0-3 $C_{1-4}$ branched or unbranched alkyl, $C_{1-4}$ alkoxy or $C_{1-4}$ alkylamino chains;
  b) phenyl, furan, thiophene, pyrrole, imidazolyl, pyridine, pyrimidine, pyridinone, dihydropyridinone, maleimide, dihydromaleimide, piperdine, piperazine or pyrazine each being optionally independently substituted with 0-3 $C_{1-4}$ branched or unbranched alkyl, $C_{1-4}$ alkoxy, hydroxy, nitrile, mono- or di-($C_{1-3}$ alkyl)amino, $C_{1-6}$ alkyl-S(O)$_m$, or halogen;

y is:
  a bond or a $C_{1-4}$ saturated or unsaturated branched or unbranched carbon chain optionally partially or fully halogenated, wherein one or more methylene groups are optionally replaced by O, NH, S(O), S(O)$_2$ or S and wherein Y is optionally independently substituted with 0-2 oxo groups and one or more $C_{1-4}$ branched or unbranched alkyl which may be substituted by one or more halogen atoms;

Z is:
  a) phenyl, pyridine, pyrimidine, pyridazine, imidazole, furan, thiophene, pyran, which are optionally substituted with one to three groups consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$, COOH and phenylamino wherein the phenyl ring is optionally substituted with one to two groups consisting of halogen, $C_{1-6}$ alkyl and $C_{1-6}$ alkoxy;
  b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, piperazine, tetrahydropyrimidone, cyclohexanone, cyclohexanol, pentamethylene sulfide, pentamethylene sulfoxide, pentamethylene sulfone, tetramethylene sulfide, tetramethylene sulfoxide or tetramethylene sulfone which are optionally substituted with one to three groups consisting of nitrile, $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;
  c) $C_{1-6}$ alkoxy, secondary or tertiary amine wherein the amino nitrogen is covalently bonded to groups selected from the group consisting of $C_{1-3}$ alkyl, $C_{1-5}$ alkoxyalkyl, pyridinyl-$C_{1-3}$ alkyl, imidazolyl-$C_{1-3}$ alkyl, tetrahydrofuranyl-$C_{1-3}$ alkyl, phenylamino, wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;

$R_1$ is:
  a) $C_{3-10}$ branched or unbranched alkyl optionally partially or fully halogenated and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described in this paragraph, and being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$)alkylaminocarbonyl;
  b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl each being optionally be partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;

c) $C_{3-10}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di($C_{1-3}$)alkylaminocarbonyl;

d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) nitrile; or f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:

a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;

$R_3$ is:

a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pteridinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, nitrile, $C_{1-3}$ alkyloxy which may optionally be partially or fully halogenated, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl, and $R_{12}$—$C_{1-5}$ alkyl($R_{13}$)N;

c) cycloalkyl selected from the group consisting of cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, alkoxycarbonylalkyl or phenylsulfonyl; or f) $C_{1-6}$ branched or unbranched alkyl optionally partially or fully halogenated;

or $R_1$ and $R_2$ taken together may optionally form a fused phenyl or pyridinyl ring;

each $R_8$ and $R_{13}$ is independently selected from the group consisting of:

hydrogen and $C_{1-4}$ branched or unbranched alkyl optionally be partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S and pharmaceutically acceptable derivatives thereof.

In a preferred embodiment the p38 kinase inhibitor is selected from the compounds as immediately described above and wherein:

$AR_2$ is naphthyl, tetrahydronaphthyl, indanyl or indenyl and W is O.

In another preferred embodiment the p38 kinase inhibitor is selected from the compounds as immediately described above and wherein:

$Ar_1$ is selected from thiophene and pyrazole;

X is $C_{5-7}$ cycloalkyl or $C_{5-7}$ cycloalkenyl optionally substituted with 0-2 oxo groups or 0-3 $C_{1-4}$ branched or unbranched alkyl, $C_{1-4}$ alkoxy or $C_{1-4}$ alkylamino; or X is phenyl, pyridine, tetrahydropyridine, pyrimidine, furan or thiophene each being optionally independently substituted with 0-3 $C_{1-4}$ branched or unbranched alkyl, $C_{1-4}$alkoxy, hydroxy, nitrile, mono- or di-($C_{1-3}$ alkyl)amino, $C_{1-6}$ alkyl-S(O)$_m$ or halogen;

$R_1$ is $C_{1-4}$alkyl branched or unbranched, cyclopropyl or cyclohexyl optionally partially or fully halogenated and optionally substituted with one to three $C_{1-3}$ alkyl groups;

$R_3$ is $C_{1-4}$alkyl branched or unbranched, phenyl, pyrimidinyl, pyrazolyl or pyridinyl each being optionally substituted as described hereinabove in the broadest generic aspect, alkoxycarbonylalkyl or cyclopropyl or cyclopentyl optionally substituted as described hereinabove in the broadest generic aspect.

In yet another preferred embodiment the p38 kinase inhibitor is selected from the compounds as immediately described above and wherein:

$Ar_1$ is pyrazole;

X is cyclopentenyl, cyclohexenyl or cycloheptenyl, optionally substituted with an oxo group or 0-3 $C_{1-4}$ branched or unbranched alkyl, $C_{1-4}$alkoxy or $C_{1-4}$alkylamino; or X is phenyl, pyridine, furan or thiophene each being optionally independently substituted with 0-3 $C_{1-4}$ branched or unbranched alkyl, $C_{1-4}$alkoxy, hydroxy, nitrile, mono- or di-($C_{1-3}$ alkyl)amino, $C_{1-6}$ alkyl-S(O)$_m$ or halogen.

In yet still another preferred embodiment the p38 kinase inhibitor is selected from the compounds as immediately described above and wherein:

Y is —CH2-, —CH2CH2-, —CH2NH—, —CH2CH2NH— or a bond; and

Z is phenyl, imidazole, furan, piperazine, tetrahydropyran, morpholine, thiomorpholine, thiomorpholine sulfoxide, piperidine, pyridine, secondary or tertiary amine wherein the amino nitrogen is covalently bonded to groups selected from the group consisting of $C_{1-3}$ alkyl and $C_{1-5}$ alkoxyalkyl, phenylamino wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$ and phenyl-S(O)$_m$ wherein the phenyl ring is optionally substituted with one to two halogen, $C_{1-6}$ alkoxy, hydroxy or mono- or di-($C_{1-3}$ alkyl)amino.

In a further embodiment the p38 kinase inhibitor is selected from the compounds as immediately described above and wherein:

$Ar_1$ is 5-tert-butyl-pyrazol-3-yl; wherein the pyrazole ring may be substituted by $R_3$;

$R_3$ is $C_{1-4}$alkyl branched or unbranched, phenyl, pyrimidinyl, pyrazolyl, pyridinyl each being optionally substituted as described hereinabove in the broadest generic aspect, alkoxycarbonylalkyl or cyclopropyl or cyclopentyl optionally substituted as described hereinabove in the broadest generic aspect.

In another preferred embodiment the p38 kinase inhibitor is selected from the compounds as immediately described above and wherein X is pyridinyl.

In another preferred embodiment the p38 kinase inhibitor is selected from the compounds as immediately described above and wherein the pyridinyl is attached to $Ar_1$ via the 3-pyridinyl position.

The following compounds are representative of the compounds the p38 kinase inhibitors which can be used in the methods described herein:

1-[5-tert-butyl-2-p-tolyl-2H-pyrazol-3-yl]-3-[4-(4-(morpholin-4-yl)phenyl)naphthalen-1-yl]urea;

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(4-dimethylaminophenyl)naphthalen-1-yl]urea;

1-[5-tert-butyl-2-p-tolyl-2H-pyrazol-3-yl]-3-[4-(3-(morpholin-4-yl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fur-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin-3-yl)naphthalen-1-yl]urea;

1-[5-tert-butyl-2-phenyl-2H-pyrazol-3-yl]-3-[4-(4-piperdin-1-ylmethyl-phenyl)naphthalen-1-yl]urea;

1-[5-tert-butyl-2-phenyl-2H-pyrazol-3-yl]-3-[4-(4-(4-methylpiperazin-1-yl)methylphenyl)naphthalen-1-yl]urea;

1-[5-tert-butyl-2-p-tolyl-2H-pyrazol-3-yl]-3-[4-(3,4-di(morpholin-4-yl-methyl)phenyl)naphthalen-1-yl]urea;

1-[5-tert-butyl-2-(6-methyl-pyridin-3-yl)-2H-pyrazol-3-yl]-3-[4-(6-pyridin-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-thiomorpholin-4-ylmethyl)pyridin-3-yl)naphthalen-1-yl]urea;

1-[5-tert-butyl-2-p-tolyl-2H-pyrazol-3-yl]-3-[4-(6-(1-oxo-thiomorpholin-4-ylmethyl)pyridin-3-yl)naphthalen-1-yl]urea;

1-[5-tert-butyl-2-(6-methyl-pyridin-3-yl)-2H-pyrazol-3-yl]-3-[4-(6-tetrahydropyran-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-tetrahydrothiophen-3-ylmethyl)pyridin-3-yl)naphthalen-1-yl]urea;

1-[5-tert-butyl-2-(6-methyl-pyridin-3-yl)-2H-pyrazol-3-yl]-3-[4-(6-(imidazol-1-ylmethyl)pyridin-3-yl)naphthalen-1-yl]urea;

1-[2-(3-dimethylaminomethylphenyl)-5-(1-methyl-cyclohexyl)-2H-pyrazol-3-yl]-3-[4-(6-morpholin-4-ylmethyl-pyridin-3-yl)naphthalen-1-yl]urea;

1-[2-(5-(1-methyl-cyclohexyl)-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(2-morpholin-4-ylmethyl-pyrimidin-5-yl)naphthalen-1-yl]urea;

1-[5-tert-butyl-2-(6-methyl-pyridin-3-yl)-2H-pyrazol-3-yl]-3-[4-(3-methoxy-5-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-(3-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-3-(dimethylamino)phenyl)naphthalen-1-yl]urea;

1-[5-tert-butyl-2-(6-methyl-pyridin-3-yl)-2H-pyrazol-3-yl]-3-[4-3-(methylsulfonyl)phenyl)naphthalen-1-yl]urea;

5-tert-butyl-3-{3-[4-(6-morpholin-4-ylmethyl-pyridin-3-yl)naphthalen-1-yl]ureido}thiophene-2-carboxylic acid methyl ester;

5-tert-butyl-3-{3-[4-(6-morpholin-4-ylmethyl-pyridin-3-yl)naphthalen-1-yl]ureido}thiophene-2-carboxylic acid methylamide;

5-tert-butyl-1-methyl-3-{3-[4-(6-morpholin-4-ylmethyl-pyridin-3-yl)naphthalen-1-yl]ureido}-1H-pyrrole-2-carboxylic acid methyl ester;

5-tert-butyl-1-methyl-3-{3-[4-(6-morpholin-4-ylmethyl-pyridin-3-yl)naphthalen-1-yl]ureido}-1H-pyrrole-2-carboxylic acid methylamide;

2-acetylamino N-(5-tert-butyl-3-{3-[4-(6-morpholin-4-ylmethyl-pyridin-3-yl)naphthalen-1-yl]ureido}thiophen-2-ylmethyl)acetamide;

1-[5-tert-butyl-2-p-tolyl-2H-pyrazol-3-yl]-3-[4-(3-morpholin-4-yl-cyclohex-1-enyl)naphthalen-1-yl]urea;

1-[5-tert-butyl-2-p-tolyl-2H-pyrazol-3-yl]-3-[4-(3-morpholin-4-yl-cylohept-1-enyl)naphthalen-1-yl]urea;

1-[5-tert-butyl-2-p-tolyl-2H-pyrazol-3-yl]-3-[4-(3-(2-morpholin-4-yl-ethylamino)cyclohex-1-enyl)naphthalen-1-yl]urea;

1-[5-tert-butyl-2-p-tolyl-2H-pyrazol-3-yl]-3-[4-(3-morpholin-4-yl-cyclohept-1-enyl)naphthalen-1-yl]urea;

1-[5-tert-butyl-2-(6-methyl-pyridin-3-yl)-2H-pyrazol-3-yl]-3-[4-(3-(pyridin-4-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(dimethylaminoethylamino)cyclohex-1-enyl)naphthalen-1-yl]urea;

1-[5-tert-butyl-2-(6-methyl-pyridin-3-yl)-2H-pyrazol-3-yl]-3-[4-(3-(pyridin-3-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(phenyl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-phenylethylamino)cyclohex-1-enyl)naphthalen-1-yl]urea;

1-[5-tert-butyl-2-(6-methyl-pyridin-3-yl)-2H-pyrazol-3-yl]-3-[4-(3-(furan-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-pyridin-2-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-piperdin-1-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-imidazol-4-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(pyridin-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-(4-methoxyphenyl)ethylamino)cyclohex-1-enyl)naphthalen-1-yl]urea;

1-[5-tert-butyl-2-p-tolyl-2H-pyrazol-3-yl]-3-[4-(4-morpholin-4-ylmethyl-3-oxo-cyclohex-1-enyl)naphthalen-1-yl]urea;

1-[5-tert-butyl-2-p-tolyl-2H-pyrazol-3-yl]-3-[4-(4-(1-oxo-tetrahydrothiophen-3-ylmethyl)-3-oxo-cyclohex-1-enyl)naphthalen-1-yl]urea;

1-[5-tert-butyl-2-p-tolyl-2H-pyrazol-3-yl]-3-[4-(4-(1-oxo-thiomorpholin-4-ylmethyl)-3-oxo-cyclohex-1-enyl)naphthalen-1-yl]urea;

1-[5-tert-butyl-2-p-tolyl-2H-pyrazol-3-yl]-3-[4-(4-methylpiperazin-1-ylmethyl)-3-oxo-cyclohex-1-enyl)naphthalen-1-yl]urea;

1-[5-tert-butyl-2-(6-methyl-pyridin-3-yl)-2H-pyrazol-3-yl]-3-[4-{6-oxo-1-(tetrahydro-pyran-4-ylmethyl)-1,2,3,6-tetrahydro-pyridin-4-yl}naphthalen-1-yl]urea;

1-[5-tert-butyl-2-(6-methyl-pyridin-3-yl)-2H-pyrazol-3-yl]-3-[4-(2-oxo-1-pyridin-4-ylmethyl-piperdin-4-yl)naphthalen-1-yl]urea;

1-[5-tert-butyl-2-p-tolyl-2H-pyrazol-3-yl]-3-[4-(6-oxo-1-pyridin-4-yl-1,2,3,6-tetrahydro-pyridin-4-yl)naphthalen-1-yl]urea;

1-[5-tert-butyl-2-(6-methyl-pyridin-3-yl)-2H-pyrazol-3-yl]-3-[4-(6-oxo-1-pyridin-4-yl-1,2,3,6-tetrahydro-pyridin-4-yl)naphthalen-1-yl]urea;

5-tert-butyl-3-{3-[4-(6-oxo-1-pyridin-4-yl-1,2,3,6-tetrahydro-pyridin-4-yl)naphthalen-1-yl]ureido}thiophene-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl amide;

5-tert-butyl-3-{3-[4-(3-morpholin-4-yl-cyclohex-1-enyl)naphthalen-1-yl]ureido}thiophene-2-carboxylic acid methyl ester;

5-tert-butyl-1-methyl-3-{3-[4-(3-morpholin-4-yl-cyclohex-1-enyl)naphthalen-1-yl]ureido}pyrrole-2-carboxylic acid methyl ester; and 5-tert-butyl-1-methyl-3-{3-[4-(3-morpholin-4-yl-cyclohex-1-enyl)naphthalen-1-yl]ureido}pyrrole-2-carboxylic acid methyl amide and the pharmaceutically acceptable derivatives thereof.

The following compounds are preferred compounds of the p38 kinase inhibitors which can be used in the methods described herein:

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fur-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin-3-yl)naphthalen-1-yl]urea and the pharmaceutically acceptable derivatives thereof.

In another preferred embodiment the invention provides a method of anticoagulant and fibrinolytic therapy for a disease or condition relating to blood coagulation or fibrinolysis comprising administering to a patient in need thereof a pharmaceutically effective a amount of a p38 MAP kinase inhibitor chosen from the compounds of formula disclosed in WO 00/55139 and corresponding U.S. Pat. No. 6,358,945:

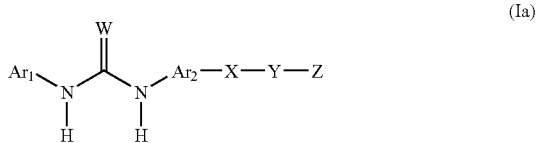

(Ia)

wherein:

$Ar_1$ is:
  pyrrole, pyrrolidine, pyrazole, imidazole, oxazole, thiazole, furan and thiophene;
  wherein $Ar_1$ is optionally substituted by one or more $R_1$, $R_2$ or $R_3$;

$Ar_2$ is:
  phenyl, naphthyl, quinoline, isoquinoline, tetrahydronaphthyl, tetrahydroquinoline, tetrahydroisoquinoline, benzimidazole, benzofuran, indanyl, indenyl and indole each being optionally substituted with zero to three $R_2$ groups;

X is:
  a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
  phenyl, furanyl, thienyl, pyrrolyl, pyrazolyl, imidazolyl, pyridinyl, tetrahydropyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-S(O)$_m$ or halogen;

Y is:
  a bond or a $C_{1-4}$ saturated or unsaturated branched or unbranched carbon chain optionally partially or fully halogenated, wherein one or more C atoms are optionally replaced by O, N, or S(O)$_m$ and wherein Y is optionally independently substituted with one to two oxo groups, nitrile, phenyl, hydroxy or one or more $C_{1-4}$ alkyl optionally substituted by one or more halogen atoms;

Z is:
  aryl, indanyl, heteroaryl selected from benzimidazolyl, pyridinyl, pyrimidinyl, pyridazinyl, pyrazinyl, imidazolyl, pyrazolyl, triazolyl, tetrazolyl, furanyl, thienyl and pyranyl, heterocycle selected from piperazinyl, tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-3}$ alkoxy-$C_{1-3}$ alkyl, $C_{1-6}$ alkoxycarbonyl, aroyl, heteroaroyl, heterocycle$C_{1-3}$acyl wherein the heteroaryl and heterocycle are as defined hereinabove in this paragraph, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-S(O)$_m$, $C_{1-6}$ alkyl-S(O)$_m$ or phenyl-S(O)$_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-S(O)$_m$— or aryl$C_{0-3}$alkyl-S(O)$_m$— each of the aforementioned alkyl and aryl attached to the amino group is optionally substituted with one to two halogen, $C_{1-6}$ alkyl, $C_{1-6}$ alkoxy, hydroxy or mono- or di-($C_{1-3}$ alkyl)amino;

or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-6}$alkyl, amino$C_{1-6}$alkyl, aryl$C_{0-3}$ alkyl, $C_{1-5}$ alkoxy$C_{1-3}$ alkyl, $C_{1-5}$ alkoxy, aroyl, $C_{1-3}$acyl, $C_{1-3}$alkyl-S(O)$_m$—, aryl$C_{0-3}$alkyl-S(O)$_m$—, nitrile$C_{1-4}$ alkyl or $C_{1-3}$alkoxy$C_{1-3}$alkyl, each of the aforementioned alkyl and aryl attached to the amino group is optionally substituted with one to two halogen, $C_{1-6}$ alkyl, $C_{1-6}$ alkoxy, hydroxy or mono- or di-($C_{1-3}$ alkyl)amino, $C_{1-6}$ alkoxyheteroaryl$C_{0-3}$alkyl, heteroaryl$C_{0-3}$alkyl or heterocycyle$C_{0-3}$alkyl wherein the heteroaryl and heterocycle is hereinabove described in this paragraph, or Z is $C_{1-6}$alkyl branched or unbranched, $C_{1-6}$alkoxy, $C_{1-3}$acylamino, nitrile$C_{1-4}$alkyl, $C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;

$R_1$ is:
  a) $C_{1-10}$ branched or unbranched alkyl optionally partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$)alkylaminocarbonyl;

b) $C_{3-7}$ cycloalkyl selected from the group consisting of cyclopropyl, cyclobutyl, cyclopentyl, cyclohexyl, cycloheptyl, bicyclopentyl, bicyclohexyl and bicycloheptyl, each optionally partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;

c) $C_{3-10}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di-($C_{1-3}$)alkylaminocarbonyl;

d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) nitrile; or f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:

a $C_{1-6}$ branched or unbranched alkyl optionally partially or fully halogenated and optionally substituted with nitrile, or $R_2$ is acetyl, aroyl, $C_{1-4}$ branched or unbranched alkoxy optionally partially or fully halogenated, halogen, methoxycarbonyl or phenylsulfonyl;

$R_3$ is:

a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of a phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl($R_{13}$)N;

c) cycloalkyl selected from the group consisting of cyclopropyl, cyclobutyl, cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, $C_{1-6}$alkoxycarbonyl$C_{1-6}$alkyl or phenylsulfonyl; or f) $C_{1-6}$ branched or unbranched alkyl optionally partially or fully halogenated;

or $R_1$ and $R_2$ taken together optionally form a fused phenyl or pyridinyl ring;

each $R_8$ and $R_{13}$ is independently selected from the group consisting of:

hydrogen and $C_{1-4}$ branched or unbranched alkyl optionally partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S;

wherein X is directly attached to one or two —Y-Z, and pharmaceutically acceptable derivatives thereof.

In a preferred embodiment the p38 kinase inhibitor is selected from the compounds as immediately described above and wherein:

$Ar_2$ is naphthyl, tetrahydronaphthyl, indanyl or indenyl and W is O.

In another preferred embodiment the p38 kinase inhibitor is selected from the compounds as immediately described above and wherein:

$Ar_1$ is thiophene or pyrazole each substituted independently by one to three $R_1$, $R_2$ or $R_3$;

X is:
  a $C_{5-7}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
  phenyl, indanyl, furanyl, thienyl, imidazolyl, pyridinyl, pyrazinyl, tetrahydrapyridinyl, pyrimidinyl, pyridinonyl, piperdinyl, benzimidazole or piperazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:
  a bond or a $C_{1-4}$ saturated or unsaturated branched or unbranched carbon chain optionally partially or fully halogenated, wherein one or more C atoms are optionally replaced by O or N, and wherein Y is optionally independently substituted with one to two oxo groups, nitrile, phenyl, hydroxy or one or more $C_{1-4}$ alkyl optionally substituted by one or more halogen atoms;

Z is:
  phenyl, heteroaryl selected from pyridinyl, imidazolyl, furanyl and thienyl, heterocycle selected from piperazinyl, 2-oxa-5-aza-bicyclo[2.2.1]heptanyl, pentamethylene sulfidyl, pentamethylene sulfoxidyl, pentamethylene sulfonyl, tetrahydrofuranyl, morpholino, thiomorpholino and piperidinyl,
  each of the aforementioned Z are optionally substituted with one to three halogen, $C_{1-6}$ alkyl, $C_{1-6}$ alkoxy, $C_{1-3}$alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$ or phenyl-$S(O)_m$ wherein the phenyl ring is optionally substituted with one to two halogen, $C_{1-6}$ alkoxy, hydroxy, halogen or mono- or di-($C_{1-3}$ alkyl) amino;
  or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy $C_{1-13}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group are optionally substituted with one to two halogen, $C_{1-6}$ alkyl or $C_{1-6}$ alkoxy;
  or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;
  or Z is hydroxy, hydroxy$C_{1-3}$alkyl, halogen, nitrile, amino wherein the N atom is optionally independently mono- or di-substituted by aroyl, $C_{1-3}$acyl, $C_{1-6}$alkyl, $C_{1-5}$ alkoxy$c_{1-3}$ alkyl, pyridinyl$C_{1-3}$alkyl, tetrahydrafuranyl $C_{1-3}$alkyl, nitrile$C_{1-4}$alkyl or phenyl wherein the phenyl ring is optionally substituted with one to two halogen, $C_{1-6}$ alkoxy, hydroxy or mono- or di-($C_{1-3}$ alkyl)amino,
  or Z is $C_{1-6}$alkyl branched or unbranched, $C_{1-6}$alkoxy or nitrile$C_{1-4}$alkyl;

$R_1$ is:
  $C_{1-4}$ branched or unbranched alkyl optionally partially or fully halogenated;
  cyclopropyl, cyclobutyl, cyclopentyl, cyclohexyl and cycloheptyl optionally partially or fully halogenated and optionally substituted with one to three $C_{1-3}$ alkyl groups, or an analog of such cycloalkyl group wherein one to three ring methylene groups are replaced by groups independently selected from the group consisting of O, S and NH;
  $C_{3-10}$ branched alkenyl optionally partially or fully halogenated and optionally substituted with one to three $C_{1-5}$ branched or unbranched alkyl;
  cyclopentenyl and cyclohexenyl optionally substituted with one to three $C_{1-3}$ alkyl groups;

$R_2$ is:
  a $C_{1-6}$ branched or unbranched alkyl optionally partially or fully halogenated and optionally substituted with nitrile;

$R_3$ is:
  phenyl or heterocyclic group selected from the group consisting of pyridinyl, pyrimidinyl, pyrazinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally be partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, hetearyloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-$C(O)$—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—$C(O)$—$C_{1-5}$ alkyl and $R_7$—$C_{1-5}$ alkyl($R_8$)N, carboxy-mono- or di-($C_{1-5}$)-alkyl-amino;
  a fused aryl selected from the group consisting of benzocyclobutanyl, indanyl, indenyl;
  wherein the fused aryl is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-$(C_{1-3})$alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-$(C_{1-3})$alkylamino-$C_5$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl($R_{13}$)N;

cycloalkyl selected from the group consisting of cyclopropyl, cyclobutyl, cyclopentyl, cyclohexyl, cycloheptyl, wherein the cycloalkyl is optionally partially or fully halogenated and optionally substituted with one to three $C_{1-3}$ alkyl groups;

$C_{1-6}$alkoxycarbonyl$C_{1-6}$alkyl;

or $R_1$ and $R_2$ taken together optionally form a fused phenyl or pyridinyl ring;

each $R_8$ and $R_{13}$ is independently selected from the group consisting of:

hydrogen and $C_{1-4}$ branched or unbranched alkyl optionally partially or fully halogenated; and each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

wherein X is directly attached to one —Y-Z.

In yet another preferred embodiment the p38 kinase inhibitor is selected from the compounds as immediately described above and wherein:

$Ar_1$ is pyrazole;

X is:

cyclopentenyl, cyclohexenyl, cycloheptenyl, optionally substituted with an oxo group or one to three $C_{1-4}$ alkyl, $C_{1-4}$ alkoxy or $C_{1-4}$ alkylamino chains each being branched or unbranched;

phenyl, furanyl, thienyl, pyridinyl, pyrazinyl piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-azabicyclo[2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino;

or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$—, pyridinyl$C_{0-3}$alkyl, tetrahydrafuranyl$C_{0-3}$alkyl, or aryl $C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-6}$alkyl, pyridinyl$C_{0-3}$alkyl, tetrahydrafuranyl$C_{0-3}$alkyl, $C_{1-5}$ alkoxy$C_{1-3}$ alkyl, $C_{1-3}$acyl, nitrile$C_{1-4}$alkyl or phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated;

cyclopropyl, cyclobutyl, cyclopentanyl, cyclohexanyl and cycloheptanyl optionally partially or fully halogenated and optionally substituted with one to three $C_{1-3}$ alkyl groups, or an analog of such cycloalkyl group wherein one to three ring methylene groups are replaced by groups independently selected from the group consisting of O, S and NH;

$C_{3-10}$ branched alkenyl optionally partially or fully halogenated and optionally substituted with one to three $C_{1-3}$ branched or unbranched alkyl;

cyclopentenyl and cyclohexenyl optionally substituted with one to three $C_{1-3}$alkyl groups;

$R_2$ is:

a $C_{1-6}$ branched or unbranched alkyl optionally partially or fully halogenated and optionally substituted with nitrile;

$R_3$ is:

phenyl or heterocyclic group selected from the group consisting of pyridinyl, pyrimidinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, phenyl $C_{1-5}$ alkyl, halogen, hydroxy, oxo, nitrile, $C_{1-3}$ alkoxy optionally partially or fully halogenated, $C_{1-3}$thioalkyl, $C_{1-3}$thioalkyl$C_{1-5}$alkyl, amino, mono- or di-($C_{1-3}$)alkylamino, $NH_2C(O)$ or a mono- or di-($C_{1-3}$)alkyl aminocarbonyl, $C_{1-6}$alkoxycarbonyl$C_{1-6}$alkyl;

or $R_3$ is cyclopropyl or cyclopentyl each optionally partially or fully halogenated and optionally substituted with one to three $C_{1-3}$ alkyl groups or $R_1$ and $R_2$ taken together optionally form a fused phenyl or pyridinyl ring.

In yet still another preferred embodiment the p38 kinase inhibitor is selected from the compounds as immediately described above and wherein:

Y is —$CH_2$—, —O—$(CH_2)_{0-3}$—, —$CH_2CH_2$—, —$CH_2NH$—, —$CH_2CH_2$—NH—, NH—$CH_2CH_2$—, —$CH_2$—NH—$CH_2$—, —NH—, —NH—C(O)—, —C(O)—, —CH(OH)—, —$CH_2(CH_2CH_3)$— or a bond;

X is:

cyclohexenyl optionally substituted with an oxo group or one to three $C_{1-4}$ alkyl, $C_{1-4}$ alkoxy or $C_{1-4}$ alkylamino chains each being branched or unbranched;

phenyl, pyridinyl, pyrazinyl, piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-azabicyclo[2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$alkyl)amino;

or Z is optionally substituted with one to three amino or aminocarbonyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-3}$alkyl, pyridinyl$C_{1-2}$alkyl, tetrahydrafuranyl$C_{1-2}$alkyl, $C_{1-3}$ alkoxy$C_{1-3}$ alkyl, $C_{1-3}$acyl, nitrile$C_{1-4}$alkyl, phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:
  $C_{1-4}$ branched or unbranched alkyl optionally partially or fully halogenated;

$R_2$ is:
  a $C_{1-3}$ branched or unbranched alkyl optionally partially or fully halogenated and optionally substituted with nitrile;

$R_3$ is:
  phenyl or heterocyclic group selected from the group consisting of pyridinyl, pyrimidinyl, and pyrazolyl, wherein such phenyl or heterocyclic group is optionally substituted with one to five groups selected from the group consisting of $C_{1-3}$ branched or unbranched alkyl which is optionally partially or fully halogenated, $C_{1-3}$ alkoxy which optionally partially or fully halogenated, $C_{1-3}$thioalkyl, $C_{1-3}$thioalkyl$C_{1-5}$alkyl, amino or $NH_2C(O)$;
  $C_{1-3}$alkoxycarbonyl;
  or $R_3$ is cyclopropyl or cyclopentyl each optionally partially or fully halogenated and optionally substituted with one to three $C_{1-3}$ alkyl groups.

In a further embodiment the p38 kinase inhibitor is selected from the compounds as immediately described above and wherein:

$Ar_1$ is 5-tert-butyl-pyrazol-3-yl; wherein the pyrazole ring is substituted independently by one to two $R_2$ or $R_3$;

X is:
  cyclohexenyl;
  phenyl, pyridinyl, pyrazinyl, piperidinyl or pyrimidinyl each being optionally independently substituted with $C_{1-2}$alkoxy or hydroxy;

Z is:
  phenyl, heteroaryl selected from pyridinyl and furanyl, heterocycle selected from 2-oxa-5-aza-bicyclo[2.2.1] heptanyl, pentamethylene sulfidyl, pentamethylene sulfoxidyl, tetrahydrofuranyl, piperazinyl, morpholino, thiomorpholino and piperidinyl, each of the aforementioned Z are optionally substituted with one to three $C_{1-3}$ alkyl, $C_{1-3}$ alkoxy, oxo, hydroxy or $NH_2C(O)$—;

or Z is hydroxy$C_{1-3}$alkyl, amino wherein the N atom is optionally independently mono- or di-substituted by pyridinylmethyl, tetrahydrafuranylmethyl, $C_{1-3}$ alkoxy$C_{1-3}$ alkyl, $C_{1-3}$acyl or nitrile$C_{1-4}$alkyl, or Z is nitrile$C_{1-4}$alkyl;

$R_3$ is:
  phenyl or heterocyclic group selected from the group consisting of pyridinyl, pyrimidinyl, and pyrazolyl, wherein such phenyl or heterocyclic group is optionally substituted with one to two groups selected from the group consisting of $C_{1-2}$ alkyl which is optionally partially or fully halogenated, $C_{1-2}$ alkoxy which optionally partially or fully halogenated, $C_{1-2}$thioalkyl, $C_{1-2}$thioalkyl$C_{1-3}$alkyl, amino or $NH_2C(O)$;
  $C_{1-3}$alkoxycarbonyl;
  or $R_3$ is cyclopropyl or cyclopentyl each optionally partially or fully halogenated and optionally substituted with one to three $C_{1-3}$ alkyl groups.

In another preferred embodiment the p38 kinase inhibitor is selected from the compounds as immediately described above and wherein X is pyridinyl.

In another preferred embodiment the p38 kinase inhibitor is selected from the compounds as immediately described above and wherein the pyridinyl is attached to $Ar_1$ via the 3-pyridinyl position.

The following compounds are preferred compounds of the p38 kinase inhibitors which can be used in the methods described herein:

1-[5-tert-butyl-2-p-tolyl-2H-pyrazol-3-yl]-3-[4-(4-morpholin-4-yl-methylphenyl)-naphthalen-1-yl]-urea;

1-[5-tert-butyl-2-p-tolyl-2H-pyrazol-3-yl]-3-[3-(4-morpholin-4-yl-methylphenyl)-naphthalen-1-yl]-urea;

1-[5-tert-butyl-2-p-tolyl-2H-pyrazol-3-yl]-3-[4-(5-morpholin-4-yl-methylfuran-2-yl)-naphthalen-1-yl]-urea;

1-[5-tert-butyl-2-p-tolyl-2H-pyrazol-3-yl]-3-[4-(3-(morpholin-4-yl-methyl)cyclohexenyl)-naphthalen-1-yl]-urea;

1-[5-tert-butyl-2-p-tolyl-2H-pyrazol-3-yl]-3-[4-(2-(4-morpholin-4-yl)ethylphenyl)-naphthalen-1-yl]-urea;

1-[5-tert-butyl-2-p-tolyl-2H-pyrazol-3-yl]-3-[4-(4-dimethylaminomethylphenyl)-naphthalen-1-yl]-urea;

1-[5-tert-butyl-2-p-tolyl-2H-pyrazol-3-yl]-3-[4-(5-(morpholin-4-yl-methyl)pyridin-2-yl)-Naphthalen-1-yl]-urea;

1-[5-tert-butyl-2-p-tolyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-methyl)pyridin-3-yl)-naphthalen-1-yl]-urea;

1-[5-tert-butyl-2-methyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(3-(2-(morpholin-4-yl)ethylamino)cyclohexenyl)-naphthalen-1-yl]-urea;

1-[5-tert-butyl-2-p-tolyl-2H-pyrazol-3-yl]-3-[4-(3,4-(morpholin-4-yl-methyl)phenyl)-naphthalen-1-yl]-urea;

1-[5-tert-butyl-2-p-tolyl-2H-pyrazol-3-yl]-3-[4-(4-methylpiperzin-1-yl-methyl)phenyl)-naphthalen-1-yl]-urea;

1-[5-tert-butyl-2-p-tolyl-2H-pyrazol-3-yl]-3-[4-(piperdin-1-yl-methyl)phenyl)-naphthalen-1-yl]-urea;

1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;

1-[5-tert-butyl-2-p-tolyl-2H-pyrazol-3-yl]-3-[4-(4-(2-(pyridin-4-yl)ethylaminomethyl)phenyl)naphthalen-1-yl]-urea;

1-[5-tert-butyl-2-p-tolyl-2H-pyrazol-3-yl]-3-[4-(4-(pyridin-3-yl-methylaminomethyl)phenyl)naphthalen-1-yl]-urea;

1-[5-tert-butyl-2-(6-methyl-pyridin-3-yl)-2H-pyrazol-3-yl]-3-[4-(4-(3,4-dimethoxyphenylmethyl)-3-hydroxyphenyl)naphthalen-1-yl]-urea;

1-[5-tert-butyl-2-p-tolyl-2H-pyrazol-3-yl]-3-[4-(6-oxo-1,6-dihydro-pyridin-3-yl)naphthalen-1-yl]-urea;

1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(morpholin-4-yl-methyl)imidazol-1-yl)naphthalen-1-yl]-urea;

1-[5-tert-butyl-2-p-tolyl-2H-pyrazol-3-yl]-3-[4-(4-(morpholin-4-yl-methyl)imidazol-1-yl)naphthalen-1-yl]-urea;

1-[5-tert-butyl-2-(6-methyl-pyridin-3-yl)-2H-pyrazol-3-yl]-3-[4-(4-(furan-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(6-(4-hydroxybutylamino)pyridin-3-yl)-naphthalen-1-yl]-urea;

1-[5-tert-butyl-2-(6-methyl-pyridin-3-yl)-2H-pyrazol-3-yl]-3-[4-(4-(pyridin-3-yl-methyl)-3-hydroxyphenyl)naphthalen-1-yl]-urea;

1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(imidazol-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(3-hydroxyrnorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(N-2-methoxyethy-N-methylaminomethyl)phenyl)naphthalen-1-yl]-urea;

1-[5-tert-butyl-2-(6-methyl-pyridin-3-yl)-2H-pyrazol-3-yl]-3-[4-(4-(4-hydroxymorpholin-4-yl-methyl)phenyl)naphthalen-1-yl]-urea;

1-[5-tert-butyl-2-(6-methyl-pyridin-3-yl)-2H-pyrazol-3-yl]-3-[4-(3-(morpholin-4-yl-methyl)cyclohexenyl)-naphthalen-1-yl]-urea;

1-[5-tert-butyl-2-(6-methyl-pyridin-3-yl)-2H-pyrazol-3-yl]-3-[4-(4-(tetrahydrofuran-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;

1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;

1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;

1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;

1-[5-tert-butyl-2-p-tolyl-2H-pyrazol-3-yl]-3-[4-(1-morpholin-4-yl-indan-5-yl)-naphthalen-1-yl]-urea;

1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(3-carboxamidomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;

1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;

1-[3-tert-butyl-1'H-[1,4']bipyrazol-5-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(furan-2-yl-methyl)-3-methoxyphenyl)naphthalen-1-yl]-urea;

1-[5-tert-butyl-2-(6-methyl-pyridin-3-yl)-2H-pyrazol-3-yl]-3-[4-(5-(morpholin-4carbonyl)pyrazin-2-yl)naphthalen-1-yl]-urea;

1-[5-tert-butyl-2-(6-methyl-pyridin-3-yl)-2H-pyrazol-3-yl]-3-[4-(6-(tetrahydrothiopyran-4-yl-amino)pyridin-3-yl)-naphthalen-1-yl]-urea;

1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;

1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(2-aminoypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-oxo-1,6-dihydropyridin-3-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;

1-[5-tert-butyl-2-(6-methyl-pyridin-3-yl)-2H-pyrazol-3-yl]-3-[4-(6-(2-oxa-5-aza-bicyclo[2.2.1]hept-5-yl-methyl)pyridin-3-yl)-naphthalen-1-yl]-urea;

1-[5-tert-butyl-2-p-tolyl-2H-pyrazol-3-yl]-3-[4-(3-carbamylphenyl)naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;

1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)amino)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)-N-methylamino)pyridin-3-yl)-naphthalen-1-yl]-urea;

1-[3-tert-butyl-1'-methyl-1'H-[1,4']bipyrazol-5-yl]-3-[4-(6-(morpholin-4-yl-methyl)pyridin-3-yl)naphthalen-1-yl]-urea;

1-[5-tert-butyl-2-benzyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(4-(N—N-di-(2-cyanoethyl)aminomethyl)phenyl)-naphthalen-1-yl]-urea;

1-[5-tert-butyl-2-p-tolyl-2H-pyrazol-3-yl]-3-[4-(4-(4-carbamylphenyl)naphthalen-1-yl]-urea;

1-[5-tert-butyl-2-(6-methyl-pyridin-3-yl)-2H-pyrazol-3-yl]-3-[4-(6-(1-oxo-tetrahydrothiopyran-4yl-amino)pyridin-3-yl)-naphthalen-1-yl]-urea;

1-[5-tert-butyl-2-(6-methyl-pyridin-3-yl)-2H-pyrazol-3-yl]-3-[4-(6-(tetrahydropyran-4-yl-amino)pyridin-3-yl)-naphthalen-1-yl]-urea;

1-[3-tert-butyl-1'-(3-cyanopropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(3-methanesulfinylphenyl)naphthalen-1-yl]urea;

1-[5-tert-butyl-2-p-tolyl-2H-pyrazol-3-yl]-3-[4-(3-methanesulfonylphenyl)naphthalen-1-yl]-urea;

1-[5-tert-butyl-2-p-tolyl-2H-pyrazol-3-yl]-3-[4-(3-sulfonamidophenyl)naphthalen-1-yl]-urea;

1-[5-tert-butyl-2-p-tolyl-2H-pyrazol-3-yl]-3-[4-(3-(morpholin-4-yl)carbonylphenyl)naphthalen-1-yl]-urea;

1-[5-tert-butyl-2-(6-methyl-pyridin-3-yl)-2H-pyrazol-3-yl]-3-[4-(5-(tetrahydrothiopyran-4yl-amino)pyrazin-2-yl)-naphthalen-1-yl]-urea;

1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;

1-[5-tert-butyl-2-p-tolyl-2H-pyrazol-3-yl]-3-[4-(6-(morpholin-4-yl-4-carbonyl)phenyl)-naphthalen-1-yl]-urea;

1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(5-(morpholin-4-yl-carbonyl)pyridin-3-yl)-naphthalen-1-yl]-urea;

1-[5-tert-butyl-2-(6-methyl-pyridin-3-yl)-2H-pyrazol-3-yl]-3-[4-(5-(morpholin-4-yl-methyl)pyrazin-2-yl)-naphthalen-1-yl]-urea;

1-[5-tert-butyl-2-(6-methyl-pyridin-3-yl)-2H-pyrazol-3-yl]-3-[4-(6-aminopyridin-3-yl)naphthalen-1-yl]-urea;

1-[5-tert-butyl-2-(6-methyl-pyridin-3-yl)-2H-pyrazol-3-yl]-3-[4-(6-(1-methylpiperdin-4-yl-amino)pyridin-3-yl)naphthalen-1-yl]-urea;

1-[5-tert-butyl-2-(2-methylpyrimidin-5-yl)-2H-pyrazol-3-yl]-3-[4-(6-(2-methyl-3-oxo-piperzin-1-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(morpholin-4-yl-carbonyl)pyridin-3-yl)naphthalen-1-yl]-urea;

1-[5-tert-butyl-2-(2-methylpyrimidin-5-yl)-2H-pyrazol-3-yl]-3-[4-(6-(N,N-di-(2-methoxyethyl)aminomethyl)pyridin-3-yl)naphthalen-1-yl]-urea;

1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(tetrahydropyran-4-yl-amino)pyridin-3-yl)naphthalen-1-yl]-urea;

1-[5-tert-butyl-2-(2-methylpyrimidin-5-yl)-2H-pyrazol-3-yl]-3-[4-(5-(morpholin-4-yl-methyl)pyrazin-2-yl)naphthalen-1-yl]-urea;

1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(6-(2-methyl-3-oxo-piperzin-1-yl-methyl)pyridin-3-yl)naphthalen-1-yl]-urea;

1-[5-tert-butyl-2-p-tolyl-2H-pyrazol-3-yl]-3-[4-(6-(pyridin-3-yl-oxy)pyridin-3-yl)naphthalen-1-yl]-urea 1-[5-tert-butyl-2-p-tolyl-2H-pyrazol-3-yl]-3-[4-(6-(pyridin-3-yl-amino)pyridin-3-yl)naphthalen-1-yl]-urea;

1-[5-tert-butyl-2-(2-methoxypyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(5-carbamylpyridin-3-yl)naphthalen-1-yl]-urea;

1-[5-tert-butyl-2-(2-aminopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(4-(morpholin-4-yl-methyl)phenyl)naphthalen-1-yl]-urea;

1-[3-tert-butyl-1'-methyl-1'H-[1,4']bipyrazol-5-yl]-3-[4-(6-(morpholin-4-yl-methyl)phenyl)naphthalen-1-yl]-urea;

1-[5-tert-butyl-2-(2-cyclopropylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(2-(pyridin-3-yl-amino)pyrimidin-5-yl)naphthalen-1-yl]-urea;

1-[5-tert-butyl-2-p-tolyl-2H-pyrazol-3-yl]-3-[4-(6-(1-oxo-tetrahydrothiopyran-4-yl-amino)pyridin-3-yl)naphthalen-1-yl]-urea;

1-[5-tert-butyl-2-p-tolyl-2H-pyrazol-3-yl]-3-[4-(6-(thiomorpholin-4-yl-methyl)pyridin-3-yl)naphthalen-1-yl]-urea;

1-[5-tert-butyl-2-p-tolyl-2H-pyrazol-3-yl]-3-[4-(3-benzyl-3H-imidazo[4,5-b]pyridin-6-yl)naphthalen-1-yl]-urea;

1-[5-tert-butyl-2-(6-methyl-pyridin-3-yl)-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(2-(morpholin-4-yl-carbonyl)pyrimidin-5-yl)naphthalen-1-yl]-urea;

1-[5-tert-butyl-2-p-tolyl-2H-pyrazol-3-yl]-3-[4-(2-(morpholin-4-yl-methyl)pyrimidin-5-yl)naphthalen-1-yl]-urea;

1-[5-tert-butyl-2-p-tolyl-2H-pyrazol-3-yl]-3-[4-(3-amino-4-carbamylphenyl)naphthalen-1-yl]-urea;

1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;

1-[5-tert-butyl-2-p-tolyl-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(6-(hydroxy-pyridin-3-yl-methyl)pyridin-3-yl)naphthalen-1-yl]-urea;

1-[5-tert-butyl-2-(2-methylpyrimidin-5-yl)-2H-pyrazol-3-yl]-3-[4-(2-(morpholin-4-yl-methyl)pyrimidin-5-yl)naphthalen-1-yl]-urea;

and the pharmaceutically acceptable derivatives thereof.

The following compounds are more preferred compounds of the p38 kinase inhibitors which can be used in the methods described herein:

1-[5-tert-butyl-2-p-tolyl-2H-pyrazol-3-yl]-3-[4-(5-(morpholin-4-yl-methyl)pyridin-2-yl)-naphthalen-1-yl]-urea;

1-[5-tert-butyl-2-p-tolyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;
1-[5-tert-butyl-2-p-tolyl-2H-pyrazol-3-yl]-3-[4-(4-(pyridin-3-yl-methylaminomethyl)phenyl)naphthalen-1-yl]-urea;
1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;
1-[5-tert-butyl-2-(6-methyl-pyridin-3-yl)-2H-pyrazol-3-yl]-3-[4-(6-(4-hydroxybutylamino)pyridin-3-yl)-naphthalen-1-yl]-urea;
1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(4-(3-hydroxypiperidin-1-yl-methyl)phenyl)naphthalen-1-yl]-urea;
1-[5-tert-butyl-2-(6-methyl-pyridin-3-yl)-2H-pyrazol-3-yl]-3-[4-(4-(4-hydroxymorpholin-4-yl-methyl)phenyl)naphthalen-1-yl]-urea;
1-[5-tert-butyl-2-(6-methyl-pyridin-3-yl)-2H-pyrazol-3-yl]-3-[4-(3-(morpholin-4-yl-methyl)cyclohexenyl)-naphthalen-1-yl]-urea;
1-[5-tert-butyl-2-(6-methyl-pyridin-3-yl)-2H-pyrazol-3-yl]-3-[4-(4-(tetrahydrofuran-3-yl-methyl)-3-hydroxyphenyl)naphthalen-1-yl]-urea;
1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;
1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;
1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;
1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;
1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]-urea;
1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;
1-[5-tert-butyl-2-(6-methyl-pyridin-3-yl)-2H-pyrazol-3-yl]-3-[4-(4-(3-carboxamidopiperidin-1-yl-methyl)phenyl)naphthalen-1-yl]-urea;
1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;
1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;
1-[3-tert-butyl-1'H-[1,4']bipyrazol-5-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(6-(tetrahydrothiopyran-4-yl-amino)pyridin-3-yl)-naphthalen-1-yl]-urea;
1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;
1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;
1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;
1-[5-tert-butyl-2-(2-aminoypyridin-5-yl)-2H-pyrazol-3-yl]-3-[4-(6-(morpholin-4-yl-methyl)pyridin-3-yl)-naphthalen-1-yl]-urea;
1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;
1-[5-tert-butyl-2-(6-methyl-pyridin-3-yl)-2H-pyrazol-3-yl]-3-[4-(6-(2-oxa-5-aza-bicyclo [2.2.1]hept-5-yl-methyl)pyridin-3-yl)-naphthalen-1-yl]-urea;
1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;
1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;
1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;
1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;
1-[3-tert-butyl-1'-methyl-1'H-[1,4']bipyrazol-5-yl]-3-[4-(6-(morpholin-4-yl-methyl)pyridin-3-yl)naphthalen-1-yl]-urea;
1-[5-tert-butyl-2-(6-methyl-pyridin-3-yl)-2H-pyrazol-3-yl]-3-[4-(6-(1-oxo-tetrahydrothiopyran-4yl-amino)pyridin-3-yl)-naphthalen-1-yl]-urea;
1-[5-tert-butyl-2-(6-methyl-pyridin-3-yl)-2H-pyrazol-3-yl]-3-[4-(6-(tetrahydropyran-4yl-amino)pyridin-3-yl)-naphthalen-1-yl]-urea;
1-[5-tert-butyl-2-(6-methyl-pyridin-3-yl)-2H-pyrazol-3-yl]-3-[4-(5-(tetrahydrothiopyran-4yl-amino)pyrazin-2-yl)-naphthalen-1-yl]-urea;
1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;
1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;
1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;
1-[5-tert-butyl-2-(2-methylpyrimidin-5-yl)-2H-pyrazol-3-yl]-3-[4-(6-(tetrahydropyran-4-yl-amino)pyridin-3-yl)naphthalen-1-yl]-urea;
1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;
1-[5-tert-butyl-2-(2-aminopyrimidin-5-yl)-2H-pyrazol-3-yl]-3-[4-(6-(morpholin-4-yl-methyl)pyridin-3-yl)naphthalen-1-yl]-urea;
1-[3-tert-butyl-1'-methyl-1'H-[1,4']bipyrazol-5-yl]-3-[4-(6-(morpholin-4-yl-methyl)phenyl)naphthalen-1-yl]-urea;
1-[5-tert-butyl-2-p-tolyl-2H-pyrazol-3-yl]-3-[4-(6-(1-oxo-tetrahydrothiopyran-4-yl-amino)pyridin-3-yl)naphthalen-1-yl]-urea;
1-[5-tert-butyl-2-p-tolyl-2H-pyrazol-3-yl]-3-[4-(6-(thiomorpholin-4-yl-methyl)pyridin-3-yl)naphthalen-1-yl]-urea;
1-[5-tert-butyl-2-p-tolyl-2H-pyrazol-3-yl]-3-[4-(2-(morpholin-4-yl-carbonyl)pyrimidin-5-yl)naphthalen-1-yl]-urea;
1-[5-tert-butyl-2-p-tolyl-2H-pyrazol-3-yl]-3-[4-(2-(morpholin-4-yl-methyl)pyrimidin-5-yl)naphthalen-1-yl]-urea;

1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(2-(morpholin-4-yl-methyl)pyrimidin-5-yl)naphthalen-1-yl]-urea and the pharmaceutically acceptable derivatives thereof.

In another preferred embodiment the invention provides a method of anticoagulant and fibrinolytic therapy for a disease or condition relating to blood coagulation or fibrinolysis comprising administering to a patient in need thereof a pharmaceutically effective a amount of a p38 MAP kinase inhibitor chosen from the compounds of formula (II) disclosed in WO 00/55139 and corresponding U.S. Pat. No. 6,358,945:

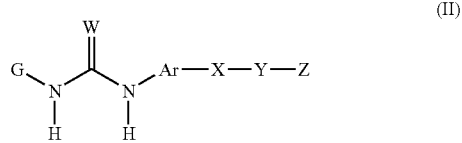

(II)

wherein:

G is:
an aromatic $C_{6-10}$ carbocycle or a nonaromatic $C_{3-10}$ carbocycle saturated or unsaturated;
a 6-10 membered heteroaryl containing 1 or more heteroatoms chosen from O, N and S;
a 5-8 membered monocyclic heterocycle containing one or more heteroatoms chosen from O, N and S; or
an 8-11 membered bicyclic heterocycle, containing one or more heteroatoms chosen from O, N and S;
wherein G is substituted by one or more $R_1$, $R_2$ or $R_3$;

Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains;
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl;

Y is:
a bond or a $C_{1-4}$ saturated or unsaturated branched or unbranched carbon chain optionally partially or fully halogenated, wherein one or more methylene groups are optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:
phenyl, pyridinyl, pyrimidinyl, pyridazinyl, pyrazinyl, imidazolyl, pyrazolyl, triazolyl, tetrazolyl, furanyl, thienyl, pyranyl each being optionally substituted with one to three halogen, $C_{1-6}$ alkyl, $C_{1-6}$ alkoxy, hydroxy, amino, mono- or di-($C_{1-3}$ alkyl)amino, $C_{1-6}$ alkyl-$S(O)_m$, CN, $CONH_2$, COOH or phenylamino wherein the phenyl ring is optionally substituted with one to two halogen, $C_{1-6}$ alkyl or $C_{1-6}$ alkoxy; tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, thiomorpholino sulfonyl, piperidinyl, piperidinonyl, piperazinyl, tetrahydropyrimidonyl, cyclohexanonyl, cyclohexanolyl, pentamethylene sulfidyl, pentamethylene sulfoxidyl, pentamethylene sulfonyl, tetramethylene sulfide, tetramethylene sulfoxidyl or tetramethylene sulfonyl each being optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, $CONH_2$, phenylamino-$C_{1-3}$ alkyl or $C_{1-3}$ alkoxy-$C_{1-3}$ alkyl;

halogen, $C_{1-4}$ alkyl, nitrile, amino, hydroxy, $C_{1-6}$ alkoxy, $NH_2C(O)$, mono- or di($C_{1-3}$alkyl) aminocarbonyl, mono- or di($C_{1-6}$alkyl)amino, secondary or tertiary amine wherein the amino nitrogen is covalently bonded to $C_{1-3}$ alkyl or $C_{1-5}$ alkoxyalkyl, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, carboxamide-$C_{1-3}$ alkyl, phenyl, wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$, wherein the phenyl ring is optionally substituted with one to two halogen, $C_{1-6}$ alkoxy, hydroxy, halogen or mono- or di-($C_{1-3}$ alkyl)amino; $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:
$C_{1-10}$ alkyl optionally be partially or fully halogenated, and optionally substituted with one to three $C_{3-10}$ cycloalkanyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl) amino, and mono- or di($C_{1-3}$alkyl)aminocarbonyl;

cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;

phenyloxy or benzyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloaryl group wherein one to two ring methyne groups are independently replaced by N;

cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;

$C_{3-10}$ branched or unbranced alkenyl each being optionally partially or fully halogenated, and optionally be substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with zero to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di-($C_{1-3}$alkyl)aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

nitrile, halogen;

methoxycarbonyl, ethoxycarbonyl and propoxycarbonyl;

silyl containing three $C_{1-4}$ alkyl groups optionally partially or fully halogenated;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, pyrrolidinyl, pyrrolyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is a $C_{1-6}$ branched or unbranched alkyl optionally partially or fully halogenated, acetyl, aroyl, $C_{1-4}$ branched or unbranched alkoxy, each being optionally partially or fully halogenated, halogen, nitrile, methoxycarbonyl, $C_{1-3}$ alkyl-$S(O)_m$ optionally partially or fully halogenated, or phenylsulfonyl;

$C_{1-6}$ alkoxy, hydroxy, amino, or mono- or di-($C_{1-4}$ alkyl) amino, nitrile, halogen;

$OR_6$;

nitro; or mono- or di-($C_{1-4}$ alkyl)amino-$S(O)_2$ optionally partially or fully halogenated, or $H_2NSO_2$;

each $R_3$ is independently:

phenyl, naphthyl, morpholinyl, pyridinyl, pyrimidinyl, pyrazinyl, pyridazinyl, pyrrolyl, pyrrolidinyl, imidazolyl, pyrazolyl, thiazolyl, oxazoyl, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkyloxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alkyl)amino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl)aminocarbonyl, $C_{1-5}$ alkyl-C (O)—$C_{1-4}$ alkyl, amino-$C_{1-5}$ alkyl, mono- or di-($C_{1-3}$alkyl)amino-$C_{1-5}$ alkyl, amino-$S(O)_2$, di-($C_{1-3}$ alkyl)amino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-$S(O)_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$— or $R_{26}C(O)(CH_2)_mN(R_{21})$—;

$C_{2-6}$ alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, $S(O)_m$ and wherein said alkynyl group is optionally independently substituted with one to two oxo groups, pyrroldinyl, pyrrolyl, morpholinyl, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl)amino optionally substituted by one or more halogen atoms; or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently:

nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}$, $R_{23}$ and $R_{24}$ is independently:

hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$ alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino;

or $R_{23}$ and $R_{24}$ taken together optionally form a heterocyclic or heteroaryl ring;

m=0, 1 or 2;

W is O or S and pharmaceutically acceptable derivatives thereof.

In a preferred embodiment the p38 kinase inhibitor is selected from the compounds as immediately described above and wherein:

G is:

phenyl, naphthyl, benzocyclobutanyl, dihydronaphthyl, tetrahydronaphthyl, benzocycloheptanyl, benzocycloheptenyl, indanyl, indenyl;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, indolinyl, indolonyl, indolinonyl, phthalimidyl; oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tetrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl;

wherein G is substituted by one or more $R_1$, $R_2$ or $R_3$;

In another preferred embodiment the p38 kinase inhibitor is selected from the compounds as immediately described above and wherein:

G is phenyl, pyridinyl, pyridonyl, naphthyl, quinolinyl, isoquinolinyl, pyrazinyl, benzimidazolyl, benzoxazolyl, benzofuranyl, benzothiophenyl, benzpyrazolyl, dihydrobenzofuranyl, dihydrobenzothiophenyl, indanyl, indenyl, indolyl, indolinyl, indolonyl or indolinonyl, wherein G is substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl Y is:

a bond or a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:

phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, amino, mono- or di-($C_{1-3}$ alkyl)amino, $CONH_2$, or OH;

nitrile, $C_{1-6}$ alkyl-$S(O)_m$, halogen, hydroxy, $C_{1-4}$ alkoxy, amino, mono- or di-($C_{1-6}$ alkyl)amino, mono- or di-($C_{1-3}$ alkyl)aminocarbonyl or $NH_2C(O)$;

each $R_1$ is independently:

$C_{3-6}$ alkyl optionally partially or fully halogenated, and optionally substituted with one to three $C_{3-6}$cycloalkyl, phenyl, thienyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile or $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$alkyl groups optionally partially or fully halogenated, CN, hydroxy$C_{1-3}$alkyl or phenyl; or an analog of such cycloalkyl group wherein one to three ring methylene groups are independently replaced by O, S, CHOH, >C=O, >C=S or NH; or silyl containing three $C_{1-4}$ alkyl groups optionally partially or fully halogenated;

$R_2$ is independently:
  halogen, $C_{1-3}$ alkoxy, $C_{1-3}$ alkyl-S(O)$_m$ optionally partially or fully halogenated, phenylsulfonyl or nitrile;

$R_3$ is independently:
  phenyl, morpholino, pyridinyl, pyrimidinyl, pyrazinyl, pyrrolyl, pyrrolylidinyl, imidazolyl, pyrazolyl, each being optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkyloxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl) amino, phenylamino, naphthylamino, heteroaryl or heterocyclic amino wherein the heteroaryl or heterocyclic moiety is as hereinabove described in this paragraph, NH$_2$C(O), a mono- or di-($C_{1-3}$alkyl)aminocarbonyl, $C_{1-5}$ alkyl-C(O)—$C_{1-4}$ alkyl, mono- or di-($C_{1-3}$alkyl) amino, mono- or di-($C_{1-3}$)alkylamino-$C_{1-5}$ alkyl, mono- or di-($C_{1-3}$alkyl)amino-S(O)$_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy-mono- or di-($C_{1-5}$)-alkyl-amino;
  $C_{1-3}$ alkyl or $C_{1-4}$ alkoxy each being optionally partially or fully halogenated or optionally substituted with $R_{17}$;
  OR$_{18}$ or $C_{1-6}$ alkyl optionally substituted with OR$_{18}$;
  amino or mono- or di-($C_{1-5}$ alkyl)amino optionally substituted with $R_{19}$;
  $R_{20}$C(O)N($R_{21}$)—, $R_{22}$O—; $R_{23}R_{24}$NC(O)—; $R_{26}$CH$_2$C(O)N($R_{21}$)— or $R_{26}$C(O)CH$_2$N($R_{21}$)—; $C_{2-4}$alkenyl substituted by $R_{23}R_{24}$NC(O)—; or
  $C_{2-4}$ alkynyl branched or unbranched carbon chain optionally partially or fully halogenated and optionally independently substituted with one to two oxo groups, pyrroldinyl, pyrrolyl, morpholinyl, piperidinyl, piperazinyl, imidazolyl, phenyl, pyridinyl, tetrazolyl or one or more $C_{1-4}$ alkyl optionally substituted by one or more halogen atoms; and $R_{23}$ and $R_{24}$ taken together optionally form imidazolyl, piperidinyl, morpholinyl, piperazinyl or a pyridinyl ring.

In yet another preferred embodiment the p38 kinase inhibitor is selected from the compounds as immediately described above and wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl or indolinonyl, wherein G is substituted by one or more $R_1$, $R_2$ or $R_3$;

Ar is naphthyl;

X is
  phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino) carbonyl, NH$_2$C(O), $C_{1-6}$ alkyl-S(O)$_m$ or halogen;

Y is:
  a bond or
  a $C_{1-4}$ saturated carbon chain wherein one of the carbon atoms is optionally replaced by O, N or S and wherein Y is optionally independently substituted with an oxo group;

Z is:
  phenyl, pyridinyl, pyrimidinyl, pyridazinyl, pyrazinyl, imidazolyl, dihydrothiazolyl, dihydrothiazolyl sulfoxide, pyranyl or pyrrolidinyl which are optionally substituted with one to two $C_{1-2}$ alkyl or $C_{1-2}$ alkoxy;
  tetrahydropyranyl, morpholinyl, thiomorpholinyl, thiomorpholino sulfoxidyl, piperidinyl, piperidinonyl, piperazinyl or tetrahydropyrimidonyl which are optionally substituted with one to two $C_{1-2}$ alkyl or $C_{1-2}$ alkoxy; or
  $C_{1-3}$ alkoxy;

each $R_1$ is independently:
  $C_{3-5}$ alkyl optionally partially or fully halogenated, and optionally substituted with phenyl substituted with zero to three halogen, $C_{1-3}$ alkyl which is optionally partially or fully halogenated, hydroxy, nitrile or $C_{1-3}$alkoxy which is optionally partially or fully halogenated;
  cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O; and
  silyl containing three $C_{1-2}$ independently alkyl groups optionally partially or fully halogenated;

each $R_2$ is independently:
  bromo, chloro, fluoro, methoxy, methylsulfonyl or nitrile;

each $R_3$ is independently:
  phenyl, morpholino, pyridinyl, pyrimidinyl, pyrrolylidinyl, 2,5-pyrrolidin-dionyl, imidazolyl, pyrazolyl, each of the aforementioned is optionally substituted with one to three $C_{1-3}$ alkyl which is optionally partially or fully halogenated, halogen, oxo, hydroxy, nitrile and $C_{1-3}$ alkyloxy optionally partially or fully halogenated;
  $C_{1-3}$ alkyl or $C_{1-3}$ alkoxy each being optionally partially or fully halogenated or optionally substituted with $R_{17}$;
  OR$_{18}$ or $C_{1-3}$ alkyl optionally substituted with OR$_{18}$;
  amino or mono- or di-($C_{1-3}$ alkyl)amino optionally substituted with $R_{19}$;
  $R_{20}$C(O)N($R_{21}$)—, $R_{22}$O—; $R_{23}R_{24}$NC(O)—; $R_{26}$CH$_2$C(O)N($R_{21}$)— or $R_{26}$C(O)CH$_2$N($R_{21}$)—;
  $C_{2-4}$ alkenyl substituted by $R_{23}R_{24}$NC(O)—; or
  $C_{2-4}$ alkynyl substituted with pyrroldinyl or pyrrolyl; and $R_{23}$ and $R_{24}$ taken together optionally form morpholino.

In yet still another preferred embodiment the p38 kinase inhibitor is selected from the compounds as immediately described above and wherein:

G is phenyl, pyridinyl, pyridonyl, naphthyl, quinolinyl, isoquinolinyl, dihydrobenzofuranyl, indanyl, indolinyl, indolonyl, or indolinonyl, wherein G is substituted by one or more $R_1$, $R_2$ or $R_3$;

Ar is 1-naphthyl;

X is:
  phenyl, imidazolyl, pyridinyl, pyrimidinyl, piperdinyl, piperazinyl, pyridazinyl or pyrazinyl;

Y is:
a bond or
—CH$_2$—, —CH$_2$CH$_2$—, —C(O)—, —O—, —S—, —NH—CH$_2$CH$_2$CH$_2$—, —N(CH$_3$)—, or —NH—;

each R$_1$ is independently:
C$_{3-5}$ alkyl optionally partially or fully halogenated, and optionally substituted with phenyl;
cyclopropyl, cyclopentanyl, cyclohexanyl and bicyclopentanyl optionally substituted with one to three methyl groups optionally partially or fully halogenated, CN, hydroxymethyl or phenyl; or 2-tetrahydrofuranyl substituted by methyl; or trimethyl silyl;

each R$_3$ is independently:
phenyl, morpholinyl, pyridinyl, pyrimidinyl, pyrrolylidinyl, 2,5-pyrrolidin-dionyl, imidazolyl or pyrazolyl, wherein any of the aforementioned is optionally substituted with C$_{1-2}$ alkyl which is optionally partially or fully halogenated;
C$_{1-3}$ alkyl or C$_{1-3}$ alkoxy each being optionally partially or fully halogenated or optionally substituted with diethylamino;
OR$_{18}$ or C$_{1-3}$ alkyl optionally substituted with OR$_{18}$;
amino or mono- or di-(C$_{1-3}$ alkyl)amino optionally substituted with R$_{19}$;
CH$_3$C(O)NH—, R$_{22}$O—; R$_{23}$R$_{24}$NC(O)—; R$_{26}$CH$_2$C(O)N(R$_{21}$)— or R$_{26}$C(O)CH$_2$N(R$_{21}$)—;
C$_{2-4}$alkenyl substituted by R$_{23}$R$_{24}$NC(O)—; or
C$_{2-4}$ alkynyl substituted with pyrroldinyl or pyrrolyl;
R$_{23}$ and R$_{24}$ are H or R$_{23}$ and R$_{24}$ taken together optionally form morpholino; and
R$_{26}$ is morpholino.

In a further embodiment the p38 kinase inhibitor is selected from the compounds as immediately described above and wherein:
G is
phenyl, pyridinyl or naphthyl wherein G is substituted by one or more R$_1$, R$_2$ or R$_3$;
X is:
imidazolyl or pyridinyl;
Y is:
—CH$_2$—, —NH—CH$_2$CH$_2$CH$_2$— or —NH—;
Z is morpholino;
each R$_1$ is independently:
tert-butyl, sec-butyl, tert-amyl or phenyl;
R$_2$ is chloro;
R$_3$ is independently:
methyl, methoxy, methoxymethyl, hydroxypropyl, acetamide, morpholino or morpholinocarbonyl.

In another preferred embodiment the p38 kinase inhibitor is selected from the compounds as immediately described above and wherein X is pyridinyl.

In another preferred embodiment the p38 kinase inhibitor is selected from the compounds as immediately described above and wherein the pyridinyl is attached to Ar via the 3-pyridinyl position.

The following compounds are preferred compounds of the p38 kinase inhibitors which can be used in the methods described herein:

1-(3-Cyano-phenyl)-3-[4-(6-morpholin-4-ylmethyl-pyridin-3-yl)-naphthalen-1-yl]-urea
1-(3-Fluoro-phenyl)-3-[4-(6-morpholin-4-ylmethyl-pyridin-3-yl)-naphthalen-1-yl]-urea
1-(4-Chloro-2-trifluoromethyl-phenyl)-3-[4-(6-morpholin-4-ylmethyl-pyridin-3-yl)-naphthalen-1-yl]-urea
1-(2-Chloro-5-trifluoromethyl-phenyl)-3-[4-(6-morpholin-4-ylmethyl-pyridin-3-yl)-naphthalen-1-yl]-urea
1-(3,4-Dimethyl-phenyl)-3-[4-(6-morpholin-4-ylmethyl-pyridin-3-yl)-naphthalen-1-yl]-urea
1-(3-Iodo-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-m-tolyl-urea
1-(4-Methylsulfanyl-phenyl)-3-[4-(6-morpholin-4-ylmethyl-pyridin-3-yl)-naphthalen-1-yl]-urea
1-(3-Chloro-4-methyl-phenyl)-3-[4-(6-morpholin-4-ylmethyl-pyridin-3-yl)-naphthalen-1-yl]-urea
1-(4-Chloro-3-nitro-phenyl)-3-[4-(6-morpholin-4-ylmethyl-pyridin-3-yl)-naphthalen-1-yl]-urea
1-(2,5-Dichloro-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-naphthalen-2-yl-urea
1-[4-(6-Morpholin-4-ylmethyl-pyridin-3-yl)-naphthalen-1-yl]-3-phenyl-urea
1-(3-Chloro-phenyl)-3-[4-(6-morpholin-4-ylmethyl-pyridin-3-yl)-naphthalen-1-yl]-urea
1-(4-Chloro-3-trifluoromethyl-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(2,4,6-trichloro-phenyl)-urea
1-(2-Methyl-3-nitro-phenyl)-3-[4-(6-morpholin-4-ylmethyl-pyridin-3-yl)-naphthalen-1-yl]-urea
1-(4-Methyl-2-nitro-phenyl)-3-[4-(6-morpholin-4-ylmethyl-pyridin-3-yl)-naphthalen-1-yl]-urea
1-(2,3-Dichloro-phenyl)-3-[4-(6-morpholin-4-ylmethyl-pyridin-3-yl)-naphthalen-1-yl]-urea
1-(2-Methoxy-5-methyl-phenyl)-3-[4-(6-morpholin-4-ylmethyl-pyridin-3-yl)-naphthalen-1-yl]-urea
1-(2-Chloro-6-methyl-phenyl)-3-[4-(6-morpholin-4-ylmethyl-pyridin-3-yl)-naphthalen-1-yl]-urea
1-(2,4-Dichloro-phenyl)-3-[4-(6-morpholin-4-ylmethyl-pyridin-3-yl)-naphthalen-1-yl]-urea
1-(4-Methyl-3-nitro-phenyl)-3-[4-(6-morpholin-4-ylmethyl-pyridin-3-yl)-naphthalen-1-yl]-urea
1-(2,4-Dimethyl-phenyl)-3-[4-(6-morpholin-4-ylmethyl-pyridin-3-yl)-naphthalen-1-yl]-urea
1-(2,3-Dimethyl-phenyl)-3-[4-(6-morpholin-4-ylmethyl-pyridin-3-yl)-naphthalen-1-yl]-urea
1-(4-Cyano-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(3,4,5-trimethoxy-phenyl)-urea
1-Biphenyl-4-yl-3-[4-(6-morpholin-4-ylmethyl-pyridin-3-yl)-naphthalen-1-yl]-urea
1-(2,5-Difluoro-phenyl)-3-[4-(6-morpholin-4-ylmethyl-pyridin-3-yl)-naphthalen-1-yl]-urea
1-(3-Chloro-2-methoxy-phenyl)-3-[4-(6-morpholin-4-ylmethyl-pyridin-3-yl)-naphthalen-1-yl]-urea
1-(2-Fluoro-3-trifluoromethyl-phenyl)-3-[4-(6-morpholin-4-ylmethyl-pyridin-3-yl)-naphthalen-1-yl]-urea
1-(4-Benzyloxy-phenyl)-3-[4-(6-morpholin-4-ylmethyl-pyridin-3-yl)-naphthalen-1-yl]-urea
1-(2-Methylsulfanyl-phenyl)-3-[4-(6-morpholin-4-ylmethyl-pyridin-3-yl)-naphthalen-1-yl]-urea
1-(2-Fluoro-6-trifluoromethyl-phenyl)-3-[4-(6-morpholin-4-ylmethyl-pyridin-3-yl)-naphthalen-1-yl]-urea
1-(4-Fluoro-3-trifluoromethyl-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(2,4,5-trimethyl-phenyl)-urea
1-[4-(6-Morpholin-4-ylmethyl-pyridin-3-yl)-naphthalen-1-yl]-3-(4-trifluoromethyl-phenyl)-urea 1-(3-Methylsulfanyl-phenyl)-3-[4-(6-morpholin-4-ylm-ethyl-pyridin-3-yl)-naphthalen-1-yl]-urea
1-(2-Methoxy-phenyl)-3-[4-(6-morpholin-4-ylmethyl-pyridin-3-yl)-naphthalen-1-yl]-urea
1-(2-Fluoro-5-trifluoromethyl-phenyl)-3-[4-(6-morpholin-4-ylmethyl-pyridin-3-yl)-naphthalen-1-yl]-urea
1-(4-Methoxy-2-methyl-phenyl)-3-[4-(6-morpholin-4-ylmethyl-pyridin-3-yl)-naphthalen-1-yl]-urea
1-(2-Fluoro-5-nitro-phenyl)-3-[4-(6-morpholin-4-ylmethyl-pyridin-3-yl)-naphthalen-1-yl]-urea
1-(4-Ethoxy-phenyl)-3-[4-(6-morpholin-4-ylmethyl-pyridin-3-yl)-naphthalen-1-yl]-urea
1-(2,5-Dimethoxy-phenyl)-3-[4-(6-morpholin-4-ylmethyl-pyridin-3-yl)-naphthalen-1-yl]-urea
1-(4,5-Dimethyl-2-nitro-phenyl)-3-[4-(6-morpholin-4-ylmethyl-pyridin-3-yl)-naphthalen-1-yl]-urea
1-(5-Chloro-2-methyl-phenyl)-3-[4-(6-morpholin-4-ylmethyl-pyridin-3-yl)-naphthalen-1-yl]-urea
1-(2-Isopropyl-6-methyl-phenyl)-3-[4-(6-morpholin-4-ylmethyl-pyridin-3-yl)-naphthalen-1-yl]-urea
1-(2-Difluoromethoxy-phenyl)-3-[4-(6-morpholin-4-ylmethyl-pyridin-3-yl)-naphthalen-1-yl]-urea
1-(4-Isopropyl-phenyl)-3-[4-(6-morpholin-4-ylmethyl-pyridin-3-yl)-naphthalen-1-yl]-urea
1-(4-Methoxy-phenyl)-3-[4-(6-morpholin-4-ylmethyl-pyridin-3-yl)-naphthalen-1-yl]-urea
1-(3-Ethyl-phenyl)-3-[4-(6-morpholin-4-ylmethyl-pyridin-3-yl)-naphthalen-1-yl]-urea
1-(2-Ethoxy-phenyl)-3-[4-(6-morpholin-4-ylmethyl-pyridin-3-yl)-naphthalen-1-yl]-urea
1-(4-Butoxy-phenyl)-3-[4-(6-morpholin-4-ylmethyl-pyridin-3-yl)-naphthalen-1-yl]-urea
4-{3-[4-(6-Morpholin-4-ylmethyl-pyridin-3-yl)-naphthalen-1-yl]-ureido}-benzoic acid ethyl ester
1-(4-Butyl-2-methyl-phenyl)-3-[4-(6-morpholin-4-ylmethyl-pyridin-3-yl)-naphthalen-1-yl]-urea
1-(2,6-Dibromo-4-isopropyl-phenyl)-3-[4-(6-morpholin-4-ylmethyl-pyridin-3-yl)-naphthalen-1-yl]-urea
1-(3-Methoxy-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(4-trifluoromethylsulfanyl-phenyl)-urea
5-{3-[4-(6-Morpholin-4-ylmethyl-pyridin-3-yl)-naphthalen-1-yl]-ureido}-isophthalic acid dimethyl ester
1-(3-Cyclopentyloxy-4-methoxy-phenyl)-3-[4-(6-morpholin-4-ylmethyl-pyridin-3-yl)-naphthalen-1-yl]-urea
3-{3-[4-(6-Morpholin-4-ylmethyl-pyridin-3-yl)-naphthalen-1-yl]-ureido}-benzoic acid ethyl ester
1-(5-tert-Butyl-2-hydroxy-phenyl)-3-[4-(6-morpholin-4-ylmethyl-pyridin-3-yl)-naphthalen-1-yl]-urea
1-(2-Hydroxymethyl-4-phenyl-cyclohexyl)-3-[4-(6-morpholin-4-ylmethyl-pyridin-3-yl)-naphthalen-1-yl]-urea
1-(2-Methylsulfanyl-5-trifluoromethyl-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(4-pentyloxy-biphenyl-3-yl)-urea
4-Methoxy-3-{[4-(6-morpholin-4-ylmethyl-pyridin-3-yl)-naphthalen-1-yl]-ureido}-benzoic acid methyl ester
1-(2,5-Diethoxy-phenyl)-3-[4-(6-morpholin-4-ylmethyl-pyridin-3-yl)-naphthalen-1-yl]-urea
1-Benzothiazol-6-yl-3-[4-(6-morpholin-4-ylmethyl-pyridin-3-y)-naphthalen-1-yl]-urea
N-(2,5-Diethoxy-4-{3-[4-(6-morpholin-4-ylmethyl-pyridin-3-yl)-naphthalen-1-yl]-ureido}-phenyl)-benzamide
1-[4-(6-Morpholin-4-ylmethyl-pyridin-3-yl)-naphthalen-1-yl]-3-(3-phenoxy-phenyl)-urea
1-(5-Ethanesulfonyl-2-methoxy-phenyl)-3-[4-(6-morpholin-4-ylmethyl-pyridin-3-yl)-naphthalen-1-yl]-urea
4-Methoxy-3-{3-[4-(6-morpholin-4-ylmethyl-pyridin-3-yl)-naphthalen-1-yl]-ureido}-N-phenyl-benzamide
1-(2-Methyl-1,3-dioxo-2,3-dihydro-1H-isoindol-5-yl)-3-[4-(6-morpholin-4-ylmethyl-pyridin-3-yl)-naphthalen-1-yl]-urea
1-(2,3-Dimethyl-1H-indol-5-yl)-3-[4-(6-morpholin-4-ylmethyl-pyridin-3-yl)-naphthalen-1-yl]-urea
N-Butyl-4-methoxy-3-{3-[4-(6-morpholin-4-ylmethyl-pyridin-3-yl)-naphthalen-1-yl]-ureido}-benzenesulfonamide
1-[3-(2-Methyl-[1,3]dioxolan-2-yl)-phenyl]-3-[4-(6-morpholin-4-ylmethyl-pyridin-3-yl)-naphthalen-1-yl]-urea
1-(3-Methoxy-5-trifluoromethyl-phenyl)-3-[4-(6-morpholin-4-ylmethyl-pyridin-3-yl)-naphthalen-1-yl]-urea
1-(2,4-Dimethoxy-phenyl)-3-[4-(6-morpholin-4-ylmethyl-pyridin-3-yl)-naphthalen-1-yl]-urea
1-(2-Methyl-4-nitro-phenyl)-3-[4-(6-morpholin-4-ylmethyl-pyridin-3-yl)-naphthalen-1-yl]-urea
1-(2-Methoxy-4-nitro-phenyl)-3-[4-(6-morpholin-4-ylmethyl-pyridin-3-yl)-naphthalen-1-yl]-urea
1-(4-Chloro-2-nitro-phenyl)-3-[4-(6-morpholin-4-ylmethyl-pyridin-3-yl)-naphthalen-1-yl]-urea
1-(5-Chloro-2-methoxy-phenyl)-3-[4-(6-morpholin-4-ylmethyl-pyridin-3-yl)-naphthalen-1-yl]-urea
1-(3,5-Dimethoxy-phenyl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(4-trifluoromethoxy-phenyl)-urea
1-[4-(6-Morpholin-4-ylmethyl-pyridin-3-yl)-naphthalen-1-yl]-3-(3-trifluoromethylsulfanyl-phenyl)-urea
1-[4-(6-Morpholin-4-ylmethyl-pyridin-3-yl)-naphthalen-1-yl]-3-(2-phenoxy-phenyl)-urea
1-(2-Methoxy-5-nitro-phenyl)-3-[4-(6-morpholin-4-ylmethyl-pyridin-3-yl)-naphthalen-1-yl]-urea
1-(5-Chloro-2,4-dimethoxy-phenyl)-3-[4-(6-morpholin-4-ylmethyl-pyridin-3-yl)-naphthalen-1-yl]-urea
1-(3,5-Bis-trifluoromethyl-phenyl)-3-[4-(6-morpholin-4-ylmethyl-pyridin-3-yl)-naphthalen-1-yl]-urea
1-(2-tert-Butyl-5-methyl-pyridin-4-yl)-3-[4-(6-morpholin-4-ylmethyl-pyridin-3-yl)-naphthalen-1-yl]-urea
1-(3-Methyl-naphthalen-2-yl)-3-[4-(6-morpholin-4-ylmethyl-pyridin-3-yl)-naphthalen-1-yl]-urea
1-(3-tert-Butyl-phenyl)-3-[4-(6-morpholin-4-ylmethyl-pyridin-3-yl)-naphthalen-1-yl]-urea
1-(4-Methyl-biphenyl-3-yl)-3-[4-(6-morpholin-4-ylmethyl-pyridin-3-yl)-naphthalen-1-yl]-urea
1-(4-tert-Butyl-biphenyl-2-yl)-3-[4-(6-morpholin-4-ylmethyl-pyridin-3-yl)-naphthalen-1-yl]-urea
1-(5-Chloro-2,4-dimethoxy-phenyl)-3-[4-(6-morpholin-4-ylmethyl-pyridin-3-yl)-naphthalen-1-yl]-urea
1-(5-Isopropyl-2-methyl-phenyl)-3-[4-(6-morpholin-4-ylmethyl-pyridin-3-yl)-naphthalen-1-yl]-urea
1-(5-sec-Butyl-2-methoxy-phenyl)-3-[4-(6-morpholin-4-ylmethyl-pyridin-3-yl)-naphthalen-1-yl]-urea
1-(5-tert-Butyl-2-methoxy-3-propyl-phenyl)-3-[4-(6-morpholin-4-ylmethyl-pyridin-3-yl)-naphthalen-1-yl]-urea
1-(5-tert-Butyl-2-methoxymethyl-phenyl)-3-[4-(6-morpholin-4-ylmethyl-pyridin-3-yl)-naphthalen-1-yl]-urea
1-(5-tert-Butyl-2-methoxy-phenyl)-3-[4-(6-morpholin-4-ylmethyl-pyridin-3-yl)-naphthalen-1-yl]-urea
1-(5-tert-Butyl-2-methyl-phenyl)-3-(4-{6-[(3-methoxy-propyl)-methyl-amino]-pyridin-3-yl}-naphthalen-1-yl)-urea
1-(5-tert-Butyl-2-methyl-phenyl)-3-[4-(4-morpholin-4-ylmethyl-imidazol-1-yl)-naphthalen-1-yl]-urea
1-(5-tert-Butyl-2-methyl-phenyl)-3-[4-(6-morpholin-4-ylmethyl-pyridin-3-yl)-naphthalen-1-yl]-urea 1-(5-tert-Butyl-2-methyl-phenyl)-3-{4-[6-(3-methoxy-propylamino)-pyridin-3-yl]-naphthalen-1-yl}-urea
1-(5-tert-Butyl-2-methyl-pyridin-3-yl)-3-[4-(6-morpholin-4-ylmethyl-pyridin-3-yl)-naphthalen-1-yl]-urea
1-(5-tert-Butyl-2-morpholin-4-yl-phenyl)-3-[4-(6-morpholin-4-ylmethyl-pyridin-3-yl)-naphthalen-1-yl]-urea
1-(6-tert-Butyl-2-chloro-3-methyl-pyridin-4-yl)-3-[4-(6-morpholin-4-ylmethyl-pyridin-3-yl)-naphthalen-1-yl]-urea
1-[4-(6-Morpholin-4-ylmethyl-pyridin-3-yl)-naphthalen-1-yl]-3-(3-trifluoromethyl-phenyl)-urea
1-[4-(6-Morpholin-4-ylmethyl-pyridin-3-yl)-naphthalen-1-yl]-3-(4-trifluoromethoxy-phenyl)-urea
1-[5-(1,1-Dimethyl-propyl)-2-methoxy-phenyl]-3-[4-(6-morpholin-4-ylmethyl-pyridin-3-yl)-naphthalen-1-yl]-urea
1-[5-tert-Butyl-2-(1H-pyrazol-4-yl)-phenyl]-3-[4-(6-morpholin-4-ylmethyl-pyridin-3-yl)-naphthalen-1-yl]-urea
1-[5-tert-Butyl-2-(2-methyl-pyrimidin-5-yl)-phenyl]-3-[4-(6-morpholin-4-ylmethyl-pyridin-3-yl)-naphthalen-1-yl]-urea
1-[5-tert-Butyl-2-(3-hydroxy-propyl)-phenyl]-3-[4-(6-morpholin-4-ylmethyl-pyridin-3-yl)-naphthalen-1-yl]-urea
1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea
1-[5-tert-Butyl-2-(morpholine-4-carbonyl)-phenyl]-3-[4-(6-morpholin-4-ylmethyl-pyridin-3-yl)-naphthalen-1-yl]-urea
N-(5-tert-Butyl-2-methoxy-3-{3-[4-(6-morpholin-4-ylmethyl-pyridin-3-yl)-naphthalen-1-yl]-ureido}-phenyl)-acetamide
1-(2-tert-Butyl-5-methyl-pyridin-4-yl)-3-[4-(6-morpholin-4-ylmethyl-pyridin-3-yl)-naphthalen-1-yl]-urea;
1-(3-Methyl-naphthalen-2-yl)-3-[4-(6-morpholin-4-ylmethyl-pyridin-3-yl)-naphthalen-1-yl]-urea;
1-(3-tert-Butyl-phenyl)-3-[4-(4-morpholin-4-ylmethyl-phenyl)-naphthalen-1-yl]-urea;
1-(3-tert-Butyl-phenyl)-3-[4-(6-morpholin-4-ylmethyl-pyridin-3-yl)-naphthalen-1-yl]-urea;
1-(4-Methyl-biphenyl-3-yl)-3-[4-(6-morpholin-4-ylmethyl-pyridin-3-yl)-naphthalen-1-yl]-urea;
1-(4-tert-Butyl-biphenyl-2-yl)-3-[4-(6-morpholin-4-ylmethyl-pyridin-3-yl)-naphthalen-1-yl]-urea;
1-(5-Chloro-2,4-dimethoxy-phenyl)-3-[4-(6-morpholin-4-ylmethyl-pyridin-3-yl)-naphthalen-1-yl]-urea;
1-(5-Isopropyl-2-methyl-phenyl)-3-[4-(6-morpholin-4-ylmethyl-pyridin-3-yl)-naphthalen-1-yl]-urea;
1-(5-sec-Butyl-2-methoxy-phenyl)-3-[4-(6-morpholin-4-ylmethyl-pyridin-3-yl)-naphthalen-1-yl]-urea;
1-(5-tert-Butyl-2-methoxy-3-propyl-phenyl)-3-[4-(6-morpholin-4-ylmethyl-pyridin-3-yl)-naphthalen-1-yl]-urea;
1-(5-tert-Butyl-2-methoxymethyl-phenyl)-3-[4-(6-morpholin-4-ylmethyl-pyridin-3-yl)-naphthalen-1-yl]-urea;
1-(5-tert-Butyl-2-methoxy-phenyl)-3-[4-(2-morpholin-4-ylmethyl-pyrimidin-5-yl)-naphthalen-1-yl]-urea;
1-(5-tert-Butyl-2-methoxy-phenyl)-3-[4-(4-thiomorpholin-4-ylmethyl-phenyl)-naphthalen-1-yl]-urea;
1-(5-tert-Butyl-2-methoxy-phenyl)-3-[4-(6-morpholin-4-ylmethyl-pyridin-3-yl)-naphthalen-1-yl]-urea;
1-(5-tert-Butyl-2-methoxy-phenyl)-3-[4-(6-morpholin-4-ylmethyl-phenyl)-naphthalen-1-yl]-urea;
1-(5-tert-Butyl-2-methoxy-phenyl)-3-{4-[4-(tetrahydro-pyran-4-ylamino)-phenyl]-naphthalen-1-yl}-urea;
1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methyl-phenyl)-3-(4-{6-[(3-methoxy-propyl)-methyl-amino]-pyridin-3-yl}-naphthalen-1-yl)-urea;
1-(5-tert-Butyl-2-methyl-phenyl)-3-[4-(4-morpholin-4-ylmethyl-imidazol-1-yl)-naphthalen-1-yl]-urea;
1-(5-tert-Butyl-2-methyl-phenyl)-3-[4-(4-morpholin-4-ylmethyl-phenyl)-naphthalen-1-yl]-urea;
1-(5-tert-Butyl-2-methyl-phenyl)-3-[4-(6-morpholin-4-ylmethyl-pyridin-3-yl)-naphthalen-1-yl]-urea;
1-(5-tert-Butyl-2-methyl-phenyl)-3-{4-[6-(3-methoxy-propylamino)-pyridin-3-yl]-naphthalen-1-yl}-urea;
1-(5-tert-Butyl-2-methyl-pyridin-3-yl)-3-[4-(6-morpholin-4-ylmethyl-pyridin-3-yl)-naphthalen-1-yl]-urea;
1-(5-tert-Butyl-2-morpholin-4-yl-phenyl)-3-[4-(6-morpholin-4-ylmethyl-pyridin-3-yl)-naphthalen-1-yl]-urea;
1-(6-tert-Butyl-2-chloro-3-methyl-pyridin-4-yl)-3-[4-(6-morpholin-4-ylmethyl-pyridin-3-yl)-naphthalen-1-yl]-urea;
1-(6-tert-Butyl-2-chloro-3-methyl-pyridin-4-yl)-3-[4-(6-thiomorpholin-4-ylmethyl-pyridin-3-yl)-naphthalen-1-yl]-urea;
1-[2-Methoxy-5-(1-methyl-cyclopropyl)-phenyl]-3-[4-(2-morpholin-4-ylmethyl-pyrimidin-5-yl)-naphthalen-1-yl]-urea;
1-[4-(6-Morpholin-4-ylmethyl-pyridin-3-yl)-naphthalen-1-yl]-3-(3-trifluoromethyl-phenyl)-urea;
1-[4-(6-Morpholin-4-ylmethyl-pyridin-3-yl)-naphthalen-1-yl]-3-(4-trifluoromethoxy-phenyl)-urea;
1-[5-(1,1-Dimethyl-propyl)-2-methoxy-phenyl]-3-[4-(4-thiomorpholin-4-ylmethyl-phenyl)-naphthalen-1-yl]-urea;
1-[5-(1,1-Dimethyl-propyl)-2-methoxy-phenyl]-3-[4-(6-morpholin-4-ylmethyl-pyridin-3-yl)-naphthalen-1-yl]-urea;
1-[5-(1-Cyano-cyclopropyl)-2-methoxy-phenyl]-3-[4-(2-morpholin-4-ylmethyl-pyrimidin-5-yl)-naphthalen-1-yl]-urea;
1-[5-tert-Butyl-2-(1H-pyrazol-4-yl)-phenyl]-3-[4-(6-morpholin-4-ylmethyl-pyridin-3-yl)-naphthalen-1-yl]-urea;
1-[5-tert-Butyl-2-(2-methyl-pyrimidin-5-yl)-phenyl]-3-[4-(5-pyridin-4-ylmethyl-pyridin-2-yl)-naphthalen-1-yl]-urea;
1-[5-tert-Butyl-2-(2-methyl-pyrimidin-5-yl)-phenyl]-3-[4-(6-morpholin-4-ylmethyl-pyridin-3-yl)-naphthalen-1-yl]-urea;
1-[5-tert-Butyl-2-(3-hydroxy-propyl)-phenyl]-3-[4-(6-morpholin-4-ylmethyl-pyridin-3-yl)-naphthalen-1-yl]-urea;
1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea;
1-[5-tert-Butyl-2-(morpholine-4-carbonyl)-phenyl]-3-[4-(6-morpholin-4-ylmethyl-pyridin-3-yl)-naphthalen-1-yl]-urea;
2-[4-tert-Butyl-2-(3-{4-[6-(2,6-dimethyl-morpholin-4-ylmethyl)-pyridin-3-yl]-naphthalen-1-yl}-ureido)-phenoxy]-acetamide;
3-{4-[3-(5-tert-Butyl-2-methoxy-phenyl)-ureido]-naphthalen-1-yl}-benzamide;
4-tert-Butyl-2-{3-[4-(2-chloro-4-morpholin-4-ylmethyl-phenyl)-naphthalen-1-yl]-ureido}-benzamide;

and the pharmaceutically acceptable derivatives thereof.

The following compounds are more preferred compounds of the p38 kinase inhibitors which can be used in the methods described herein:

1-(2-tert-Butyl-5-methyl-pyridin-4-yl)-3-[4-(6-morpholin-4-ylmethyl-pyridin-3-yl)-naphthalen-1-yl]-urea;

1-(3-tert-Butyl-phenyl)-3-[4-(6-morpholin-4-ylmethyl-pyridin-3-yl)-naphthalen-1-yl]-urea;
1-(4-Methyl-biphenyl-3-yl)-3-[4-(6-morpholin-4-ylmethyl-pyridin-3-yl)-naphthalen-1-yl]-urea;
1-(4-tert-Butyl-biphenyl-2-yl)-3-[4-(6-morpholin-4-ylmethyl-pyridin-3-yl)-naphthalen-1-yl]-urea;
1-(5-Isopropyl-2-methyl-phenyl)-3-[4-(6-morpholin-4-ylmethyl-pyridin-3-yl)-naphthalen-1-yl]-urea;
1-(5-sec-Butyl-2-methoxy-phenyl)-3-[4-(6-morpholin-4-ylmethyl-pyridin-3-yl)-naphthalen-1-yl]-urea;
1-(5-tert-Butyl-2-methoxymethyl-phenyl)-3-[4-(6-morpholin-4-ylmethyl-pyridin-3-yl)-naphthalen-1-yl]-urea;
1-(5-tert-Butyl-2-methoxy-phenyl)-3-[4-(6-morpholin-4-ylmethyl-pyridin-3-yl)-naphthalen-1-yl]-urea;
1-(5-tert-Butyl-2-methyl-phenyl)-3-(4-{6-[(3-methoxy-propyl)-methyl-amino]-pyridin-3-yl}-naphthalen-1-yl)-urea;
1-(5-tert-Butyl-2-methyl-phenyl)-3-[4-(6-morpholin-4-ylmethyl-pyridin-3-yl)-naphthalen-1-yl]-urea;
1-(5-tert-Butyl-2-methyl-pyridin-3-yl)-3-[4-(6-morpholin-4-ylmethyl-pyridin-3-yl)-naphthalen-1-yl]-urea;
1-[5-(1,1-Dimethyl-propyl)-2-methoxy-phenyl]-3-[4-(6-morpholin-4-ylmethyl-pyridin-3-yl)-naphthalen-1-yl]-urea;
1-[5-tert-Butyl-2-(1H-pyrazol-4-yl)-phenyl]-3-[4-(6-morpholin-4-ylmethyl-pyridin-3-yl)-naphthalen-1-yl]-urea;
1-[5-tert-Butyl-2-(2-methyl-pyrimidin-5-yl)-phenyl]-3-[4-(6-morpholin-4-ylmethyl-pyridin-3-yl)-naphthalen-1-yl]-urea;
1-[5-tert-Butyl-2-(3-hydroxy-propyl)-phenyl]-3-[4-(6-morpholin-4-ylmethyl-pyridin-3-yl)-naphthalen-1-yl]-urea;
1-[5-tert-Butyl-2-(morpholine-4-carbonyl)-phenyl]-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-acetamide and the pharmaceutically acceptable derivatives thereof.

The following compounds are more preferred compounds of the p38 kinase inhibitors which can be used in the methods described herein:
1-(4-tert-Butyl-phenyl)-3-[4-(6-morpholin-4-ylmethyl-pyridin-3-yl)-naphthalen-1-yl]-urea;
1-(5-tert-Butyl-2-methyl-phenyl)-3-[4-(4-morpholin-4-ylmethyl-piperidin-1-yl)-naphthalen-1-yl]-urea;
1-(6-Chloro-4-trifluoromethyl-pyridin-2-yl)-3-[4-(6-morpholin-4-ylmethyl-pyridin-3-yl)-naphthalen-1-yl]-urea;
1-(4-Difluoromethoxy-phenyl)-3-[4-(6-morpholin-4-ylmethyl-pyridin-3-yl)-naphthalen-1-yl]-urea;
1-(3-Methyl-naphthalen-2-yl)-3-[4-(6-morpholin-4-ylmethyl-pyridin-3-yl)-naphthalen-1-yl]-urea;
1-[2-Methoxy-5-(1-methyl-1-phenyl-ethyl)-phenyl]-3-[4-(6-morpholin-4-ylmethyl-pyridin-3-yl)-naphthalen-1-yl]-urea;
(5-tert-Butyl-2-methyl-phenyl)-carbamic acid 3-(5-{4-[3-(5-tert-butyl-2-methyl-phenyl)-ureido]-naphthalen-1-yl}-pyridin-2-ylamino)-propyl ester;
1-(6-tert-Butyl-benzo[1,3]dioxol-5-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-acetamide;
1,3-Bis-[4-(6-morpholin-4-ylmethyl-pyridin-3-yl)-naphthalen-1-yl]-urea;
1-[5-tert-Butyl-3-(2,2-dimethyl-[1,3]dioxolan-4-ylmethyl)-2-hydroxy-phenyl]-3-[4-(6-morpholin-4-ylmethyl-pyridin-3-yl)-naphthalen-1-yl]-urea;
1-[5-tert-Butyl-2-(2-pyrrolidin-1-yl-ethoxy)-phenyl]-3-[4-(6-morpholin-4-ylmethyl-pyridin-3-yl)-naphthalen-1-yl]-urea;
1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;
1-(2,3-Dimethyl-1H-indol-5-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(2-p-tolyloxy-5-trifluoromethyl-phenyl)-urea;
1-[2-(2-Methoxy-phenoxy)-5-trifluoromethyl-phenyl]-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-naphthalen-1-yl-urea;
1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;
1-{5-tert-Butyl-2-[3-(tetrahydro-pyran-2-yloxy)-prop-1-ynyl]-phenyl}-3-[4-(6-morpholin-4-ylmethyl-pyridin-3-yl)-naphthalen-1-yl]-urea;
1-(5-Hydroxymethyl-2-methyl-phenyl)-3-[4-(6-morpholin-4-ylmethyl-pyridin-3-yl)-naphthalen-1-yl]-urea;
1-(2-Methoxy-dibenzofuran-3-yl)-3-[4-(6-morpholin-4-ylmethyl-pyridin-3-yl)-naphthalen-1-yl]-urea;
1-(2,5-Di-tert-butyl-phenyl)-3-[4-(6-morpholin-4-ylmethyl-pyridin-3-yl)-naphthalen-1-yl]-urea;
1-[3-(4-Bromo-1-methyl-1H-pyrazol-3-yl)-phenyl]-3-[4-(6-morpholin-4-ylmethyl-pyridin-3-yl)-naphthalen-1-yl]-urea;
1-(3-Hydroxy-5,6,7,8-tetrahydro-naphthalen-2-yl)-3-[4-(6-morpholin-4-ylmethyl-pyridin-3-yl)-naphthalen-1-yl]-urea;
1-(1-Acetyl-2,3-dihydro-1H-indol-5-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3-oxazol-5-yl-phenyl)-urea;
1-[4-(6-Morpholin-4-ylmethyl-pyridin-3-yl)-naphthalen-1-yl]-3-(3-[1,3,4]oxadiazol-2-yl-phenyl)-urea;
1-(2-Methoxy-5-trifluoromethyl-phenyl)-3-[4-(6-morpholin-4-ylmethyl-pyridin-3-yl)-naphthalen-1-yl]-urea;
Furan-2-carboxylic acid (4-tert-butyl-2-{3-[4-(6-morpholin-4-ylmethyl-pyridin-3-yl)-naphthalen-1-yl]-ureido}-phenyl)-amide;
1-(2-Methoxy-4-phenylamino-phenyl)-3-[4-(6-morpholin-4-ylmethyl-pyridin-3-yl)-naphthalen-1-yl]-urea;
1-(5-Methoxy-2-methyl-phenyl)-3-[4-(6-morpholin-4-ylmethyl-pyridin-3-yl)-naphthalen-1-yl]-urea;
1-(3-Hydroxy-naphthalen-2-yl)-3-[4-(6-morpholin-4-ylmethyl-pyridin-3-yl)-naphthalen-1-yl]-urea;
N,N-Diethyl-4-methoxy-3-{3-[4-(6-morpholin-4-ylmethyl-pyridin-3-yl)-naphthalen-1-yl]-ureido}-benzenesulfonamide;
1-(2,2-Difluoro-benzo[1,3]dioxol-5-yl)-3-[4-(6-morpholin-4-ylmethyl-pyridin-3-yl)-naphthalen-1-yl]-urea;
1-[5-(1,1-Dimethyl-propyl)-2-phenoxy-phenyl]-3-[4-(6-morpholin-4-ylmethyl-pyridin-3-yl)-naphthalen-1-yl]-urea;
1-[5-(2,2-Dimethyl-propionyl)-2-methyl-phenyl]-3-[4-(6-morpholin-4-ylmethyl-pyridin-3-yl)-naphthalen-1-yl]-urea;
2-Chloro-5-{3-[4-(6-morpholin-4-ylmethyl-pyridin-3-yl)-naphthalen-1-yl]-ureido}-benzoic acid isopropyl ester;
1-(4-Amino-3,5-dibromo-phenyl)-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

2-(5-tert-Butyl-2-methoxy-phenyl)-N-[4-(6-morpholin-4-ylmethyl-pyridin-3-yl)-naphthalen-1-yl]-acetamide;

1-(2-Methoxy-5-phenoxy-phenyl)-3-[4-(6-morpholin-4-ylmethyl-pyridin-3-yl)-naphthalen-1-yl]-urea;

1-(3,3-Dimethyl-2-oxo-2,3-dihydro-1H-indol-7-yl)-3-[4-(6-morpholin-4-ylmethyl-pyridin-3-yl)-naphthalen-1-yl]-urea;

1-(5-tert-Butyl-2-cyclopentyloxy-phenyl)-3-[4-(6-morpholin-4-ylmethyl-pyridin-3-yl)-naphthalen-1-yl]-urea;

1-(5-tert-Butyl-2-methoxy-phenyl)-3-{4-[6-(3-pyridin-3-yl-pyrrolidin-1-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(6-tert-Butyl-3-oxo-3,4-dihydro-2H-benzo[1,4]oxazin-7-yl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-[6-tert-Butyl-4-(2-morpholin-4-yl-ethyl)-3-oxo-3,4-dihydro-2H-benzo[1,4]oxazin-8-yl]-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

N-(5-tert-Butyl-2-methoxy-4-{3-[4-(6-morpholin-4-ylmethyl-pyridin-3-yl)-naphthalen-1-yl]-ureido}-phenyl)-methanesulfonamide;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-(2-Ethanesulfonyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(3-dimethylamino-pyrrolidin-1-ylmethyl)-pyridin-3-yl]-naphthalen-1-yl}-urea;

N-[1-(5-{4-[3-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-{3-[4-(6-morpholin-4-ylmethyl-pyridin-3-yl)-naphthalen-1-yl]-ureido}-phenyl)-isobutyramide;

2-(4-tert-Butyl-2-{3-[4-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(6-tert-Butyl-3-cyano-2-methoxymethoxy-pyridin-4-yl)-3-[4-(6-morpholin-4-ylmethyl-pyridin-3-yl)-naphthalen-1-yl]-urea;

1-(6-tert-Butyl-3-cyano-2-hydroxy-pyridin-4-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(1,3,3-trimethyl-2,3-dihydro-1H-indol-5-yl)-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(4-morpholin-4-yl-methyl-piperidin-1-yl)-naphthalen-1-yl]-urea;

1-[5-tert-Butyl-2-(1-methyl-1H-pyrazol-4-yl)-phenyl]-3-[4-(4-morpholin-4-ylmethyl-piperidin-1-yl)-naphthalen-1-yl]-urea;

1-(5-tert-Butyl-2-methoxy-phenyl)-3-[4-(2-morpholin-4-yl-methyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-3-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

N-(5-{4-[3-(5-tert-Butyl-2-methyl-phenyl)-ureido]-naphthalen-1-yl}-pyrazin-2-yl)-methanesulfonamide;

1-[4-(6-{[Bis-(2-cyano-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;

1-(5-tert-Butyl-2-methoxy-phenyl)-3-{4-[6-(2-methoxymethyl-morpholin-4-ylmethyl)-pyridin-3-yl]-naphthalen-1-yl}-urea;

1-(5-tert-Butyl-2-methoxy-phenyl)-3-(4-{6-[(2-morpholin-4-yl-ethylamino)-methyl]-pyridin-3-yl}-naphthalen-1-yl)-urea;

1-(5-tert-Butyl-2-methoxy-phenyl)-3-{4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-{4-[3-(5-tert-Butyl-2-methoxy-phenyl)-ureido]-naphthalen-1-yl}-pyridin-2-ylmethyl)-piperidine-4-carboxylic acid amide;

1-(5-tert-Butyl-2-methoxy-phenyl)-3-{4-[6-(1-oxo-114-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-{4-[6-(4-Acetyl-piperazin-1-ylmethyl)-pyridin-3-yl]-naphthalen-1-yl}-3-(5-tert-butyl-2-methoxy-phenyl)-urea;

4-(5-{4-[3-(5-tert-Butyl-2-methoxy-phenyl)-ureido]-naphthalen-1-yl}-pyridin-2-ylmethyl)-piperazine-1-carboxylic acid ethyl ester;

1-(5-tert-Butyl-2-methoxy-phenyl)-3-(4-{6-[(2-pyridin-3-yl-ethylamino)-methyl]-pyridin-3-yl}-naphthalen-1-yl)-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-(4-{6-[(2-methylsulfanyl-ethylamino)-methyl]-pyridin-3-yl}-naphthalen-1-yl)-urea;

1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-tert-Butyl-2-methoxy-phenyl)-3-(4-{6-[(2-piperazin-1-yl-ethylamino)-methyl]-pyridin-3-yl}-naphthalen-1-yl)-urea;

1-(5-tert-Butyl-2-methoxy-phenyl)-3-{4-[6-(4-pyrimidin-2-yl-piperazin-1-ylmethyl)-pyridin-3-yl]-naphthalen-1-yl}-urea;

1-(5-tert-Butyl-2-methoxy-phenyl)-3-{4-[6-(4-pyridin-2-yl-piperazin-1-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-{4-[6-(2-thia-5-aza-bicyclo[2.2.1]hept-5-ylmethyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

1-(5-tert-Butyl-2-methoxy-phenyl)-3-{4-[6-(pyridin-3-ylamino)-pyridin-3-yl]-naphthalen-1-yl}-urea;

[4-(6-Morpholin-4-ylmethyl-pyridin-3-yl)-naphthalen-1-yl]-carbamic acid 3-tert-butyl-phenyl ester;

N-(5-tert-Butyl-2-methoxy-3-{3-[4-(6-morpholin-4-ylmethyl-pyridin-3-yl)-naphthalen-1-yl]-ureido}-phenyl)-methanesulfonamide and and the pharmaceutically acceptable derivatives thereof.

The following compounds are more preferred compounds of the p38 kinase inhibitors which can be used in the methods described herein:

1-(3-Methyl-naphthalen-2-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;
1-(2,3-Dimethyl-1H-indol-5-yl)-3-[4-(6-morpholin-4-ylmethyl-pyridin-3-yl)-naphthalen-1-yl]-urea;
1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;
1-(2-Methoxy-5-trifluoromethyl-phenyl)-3-[4-(6-morpholin-4-ylmethyl-pyridin-3-yl)-naphthalen-1-yl]-urea;
1-[5-(2,2-Dimethyl-propionyl)-2-methyl-phenyl]-3-[4-(6-morpholin-4-ylmethyl-pyridin-3-yl)-naphthalen-1-yl]-urea;
1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;
1-[5-tert-Butyl-2-(3-hydroxy-prop-1-ynyl)-phenyl]-3-[4-(6-morpholin-4-ylmethyl-pyridin-3-yl)-naphthalen-1-yl]-urea;
1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;
1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;
1-(5-tert-Butoxy-2-methoxy-phenyl)-3-[4-(6-morpholin-4-ylmethyl-pyridin-3-yl)-naphthalen-1-yl]-urea;
1-[5-(1-Cyano-cyclopropyl)-2-methoxy-phenyl]-3-[4-(6-morpholin-4-ylmethyl-pyridin-3-yl)-naphthalen-1-yl]-urea;
1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;
1-(5-tert-Butyl-2-methoxy-phenyl)-3-[4-(6-[1,3]dioxolan-2-yl-pyridin-3-yl)-naphthalen-1-yl]-urea;
1-(5-tert-Butyl-2-pyrrolidin-1-yl-phenyl)-3-[4-(6-morpholin-4-ylmethyl-pyridin-3-yl)-naphthalen-1-yl]-urea;
1-(5-tert-Butyl-2-dimethylamino-phenyl)-3-[4-(6-morpholin-4-ylmethyl-pyridin-3-yl)-naphthalen-1-yl]-urea;
1-(5-tert-Butyl-2-propoxy-phenyl)-3-[4-(6-morpholin-4-ylmethyl-pyridin-3-yl)-naphthalen-1-yl]-urea;
1-(5-tert-Butyl-2-methoxy-phenyl)-3-[4-(6-hydroxymethyl-pyridin-3-yl)-naphthalen-1-yl]-urea;
1-(5-tert-Butyl-2-methoxy-phenyl)-3-{4-[6-(2,6-dimethyl-morpholin-4-ylmethyl)-pyridin-3-yl]-naphthalen-1-yl}-urea;
1-(5-Cyclohexyl-2-methoxy-phenyl)-3-[4-(6-morpholin-4-ylmethyl-pyridin-3-yl)-naphthalen-1-yl]-urea;
1-(2,4-Dimethoxy-5-trifluoromethyl-phenyl)-3-[4-(6-morpholin-4-ylmethyl-pyridin-3-yl)-naphthalen-1-yl]-urea;
1-(5-tert-Butyl-2-methoxy-3-nitro-phenyl)-3-[4-(6-morpholin-4-ylmethyl-pyridin-3-yl)-naphthalen-1-yl]-urea;
1-(3-Amino-5-tert-butyl-2-methoxy-phenyl)-3-[4-(6-methyl-pyridin-3-yl)-naphthalen-1-yl]-urea;
N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;
1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;
1-(5-tert-Butyl-2-ethoxy-phenyl)-3-[4-(6-morpholin-4-ylmethyl-pyridin-3-yl)-naphthalen-1-yl]-urea;
1-(5-tert-Butyl-2-isopropoxy-phenyl)-3-[4-(6-morpholin-4-ylmethyl-pyridin-3-yl)-naphthalen-1-yl]-urea;
1-(5-tert-Butyl-2-imidazol-1-yl-phenyl)-3-[4-(6-morpholin-4-ylmethyl-pyridin-3-yl)-naphthalen-1-yl]-urea;
1-(5-tert-Butyl-3-ethylamino-2-methoxy-phenyl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;
1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;
1-(2-Methanesulfinyl-5-trifluoromethyl-phenyl)-3-[4-(6-morpholin-4-ylmethyl-pyridin-3-yl)-naphthalen-1-yl]-urea;
1-[4-(6-{[Bis-(2-methoxy-ethyl)-amino]-methyl}-pyridin-3-yl)-naphthalen-1-yl]-3-(5-tert-butyl-2-methoxy-phenyl)-urea;
N-[1-(5-{4-[3-(5-tert-Butyl-2-methoxy-phenyl)-ureido]-naphthalen-1-yl}-pyridin-2-ylmethyl)-pyrrolidin-3-yl]-acetamide;
1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-propionamide;
1-(5-tert-Butyl-2-methyl-benzooxazol-7-yl)-3-[4-(6-morpholin-4-ylmethyl-pyridin-3-yl)-naphthalen-1-yl]-urea;
1-[4-(6-Morpholin-4-ylmethyl-pyridin-3-yl)-naphthalen-1-yl]-3-(3-trifluoromethanesulfonyl-phenyl)-urea;
N-(5-tert-Butyl-2-methoxy-3-{3-[4-(6-morpholin-4-ylmethyl-pyridin-3-yl)-naphthalen-1-yl]-ureido}-phenyl)-isobutyramide;
2-(4-tert-Butyl-2-{3-[4-(6-morpholin-4-ylmethyl-pyridin-3-yl)-naphthalen-1-yl]-ureido}-phenoxy)-acetamide;
1-(5-tert-Butyl-2-oxo-2,3-dihydro-benzooxazol-7-yl)-3-[4-(6-morpholin-4-ylmethyl-pyridin-3-yl)-naphthalen-1-yl]-urea;
1-(5-tert-Butyl-3-cyano-2-methoxy-phenyl)-3-[4-(6-morpholin-4-ylmethyl-pyridin-3-yl)-naphthalen-1-yl]-urea;
1-(5-tert-Butyl-benzooxazol-7-yl)-3-[4-(6-morpholin-4-ylmethyl-pyridin-3-yl)-naphthalen-1-yl]-urea;
N-(5-tert-Butyl-2-methoxy-3-{3-[4-(6-morpholin-4-ylmethyl-pyridin-3-yl)-naphthalen-1-yl]-ureido}-phenyl)-benzenesulfonamide;
Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
1-(5-tert-Butyl-2-methoxy-phenyl)-3-[4-(2-morpholin-4-ylmethyl-pyrimidin-5-yl)-naphthalen-1-yl]-urea;
1-(5-tert-Butyl-2-methylsulfanyl-phenyl)-3-[4-(6-morpholin-4-ylmethyl-pyridin-3-yl)-naphthalen-1-yl]-urea;
1-(5-tert-Butyl-2-methoxy-pyridin-3-yl)-3-[4-(6-morpholin-4-ylmethyl-pyridin-3-yl)-naphthalen-1-yl]-urea;
2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;
N-(5-{4-[3-(5-tert-Butyl-2-methyl-phenyl)-ureido]-naphthalen-1-yl}-pyrazin-2-yl)-methanesulfonamide;
1-[4-(6-{[Bis-(2-cyano-ethyl)-amino]-methyl}-pyridin-3-yl)-naphthalen-1-yl]-3-(5-tert-butyl-2-methoxy-phenyl)-urea;
1-(5-tert-Butyl-2-methoxy-phenyl)-3-{4-[6-(4-methyl-piperazin-1-ylmethyl)-pyridin-3-yl]-naphthalen-1-yl}-urea;
1-(5-tert-Butyl-2-methoxy-phenyl)-3-[4-(6-thiomorpholin-4-ylmethyl-pyridin-3-yl)-naphthalen-1-yl]-urea;
1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahy-dro-thiopyran-4-ylamino)-pyridin-3-yl]-naphthalen-1-yl}-urea;
1-(5-tert-Butyl-2-methoxy-phenyl)-3-{4-[6-(tetrahydro-py-ran-4-ylamino)-pyridin-3-yl]-naphthalen-1-yl}-urea;
1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;
1-(5-tert-Butyl-2-methoxy-phenyl)-3-{4-[6-(2-methoxym-ethyl-morpholin-4-ylmethyl)-pyridin-3-yl]-naphthalen-1-yl}-urea;
1-(5-tert-Butyl-2-methoxy-phenyl)-3-{4-[6-(2-methyl-3-oxo-piperazin-1-ylmethyl)-pyridin-3-yl]-naphthalen-1-yl}-urea;
1-(5-{4-[3-(5-tert-Butyl-2-methoxy-phenyl)-ureido]-naph-thalen-1-yl}-pyridin-2-ylmethyl)-piperidine-3-carboxylic acid amide;
1-(5-tert-Butyl-2-methoxy-phenyl)-3-{4-[6-(1-oxo-1l4-thiomorpholin-4-ylmethyl)-pyridin-3-yl]-naphthalen-1-yl}-urea;
1-(3,3-Dimethyl-2-oxo-2,3-dihydro-1H-indol-5-yl)-3-[4-(6-morpholin-4-ylmethyl-pyridin-3-yl)-naphthalen-1-yl]-urea;
1-(5-tert-Butyl-2-methoxy-phenyl)-3-{4-[6-(3-oxo-piper-azin-1-ylmethyl)-pyridin-3-yl]-naphthalen-1-yl}-urea;
1-(5-tert-Butyl-2-methoxy-phenyl)-3-(4-{6-[(tetrahydro-fu-ran-3-ylamino)-methyl]-pyridin-3-yl}-naphthalen-1-yl)-urea;
1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;
1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;
1-(5-tert-Butyl-2-methoxy-phenyl)-3-{4-[6-(2,6-dimethyl-morpholin-4-ylmethyl)-pyridin-3-yl]-naphthalen-1-yl}-urea;
1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;
1-(5-tert-Butyl-2-methoxy-phenyl)-3-{4-[6-(morpholine-4-carbonyl)-pyridin-3-yl]-naphthalen-1-yl}-urea;
1-(5-tert-Butyl-2-methoxy-phenyl)-3-[4-(5-morpholin-4-yl-methyl-pyrazin-2-yl)-naphthalen-1-yl]-urea;
1-(6-tert-Butyl-3-oxo-3,4-dihydro-2H-benzo[1,4]oxazin-8-yl)-3-[4-(6-morpholin-4-ylmethyl-pyridin-3-yl)-naphtha-len-1-yl]-urea;
1-(3-Amino-5-tert-butyl-2-methoxy-phenyl)-3-[4-(6-mor-pholin-4-ylmethyl-pyridin-3-yl)-naphthalen-1-yl]-urea;
N-(5-{4-[3-(5-tert-Butyl-2-methoxy-phenyl)-ureido]-naph-thalen-1-yl}-pyridin-2-yl)-acetamide;
N-(5-tert-Butyl-2-methoxy-3-{3-[4-(6-morpholin-4-ylm-ethyl-pyridin-3-yl)-naphthalen-1-yl]-ureido}-phenyl)-N-methyl-acetamide;
N-(5-tert-Butyl-2-methoxy-3-{3-[4-(6-morpholin-4-ylm-ethyl-pyridin-3-yl)-naphthalen-1-yl]-ureido}-phenyl)-2,2,2-trifluoro-acetamide;
1-(5-tert-Butyl-2-methoxy-phenyl)-3-{4-[6-(pyridin-3-yloxy)-pyridin-3-yl]-naphthalen-1-yl}-urea;
[4-(6-Morpholin-4-ylmethyl-pyridin-3-yl)-naphthalen-1-yl]-carbamic acid 3-tert-butyl-phenyl ester;
N-(5-tert-Butyl-2-methoxy-3-{3-[4-(6-morpholin-4-ylm-ethyl-pyridin-3-yl)-naphthalen-1-yl]-ureido}-phenyl)-methanesulfonamide and and the pharmaceutically acceptable derivatives thereof.

More preferred, the p38 kinase inhibitors are:

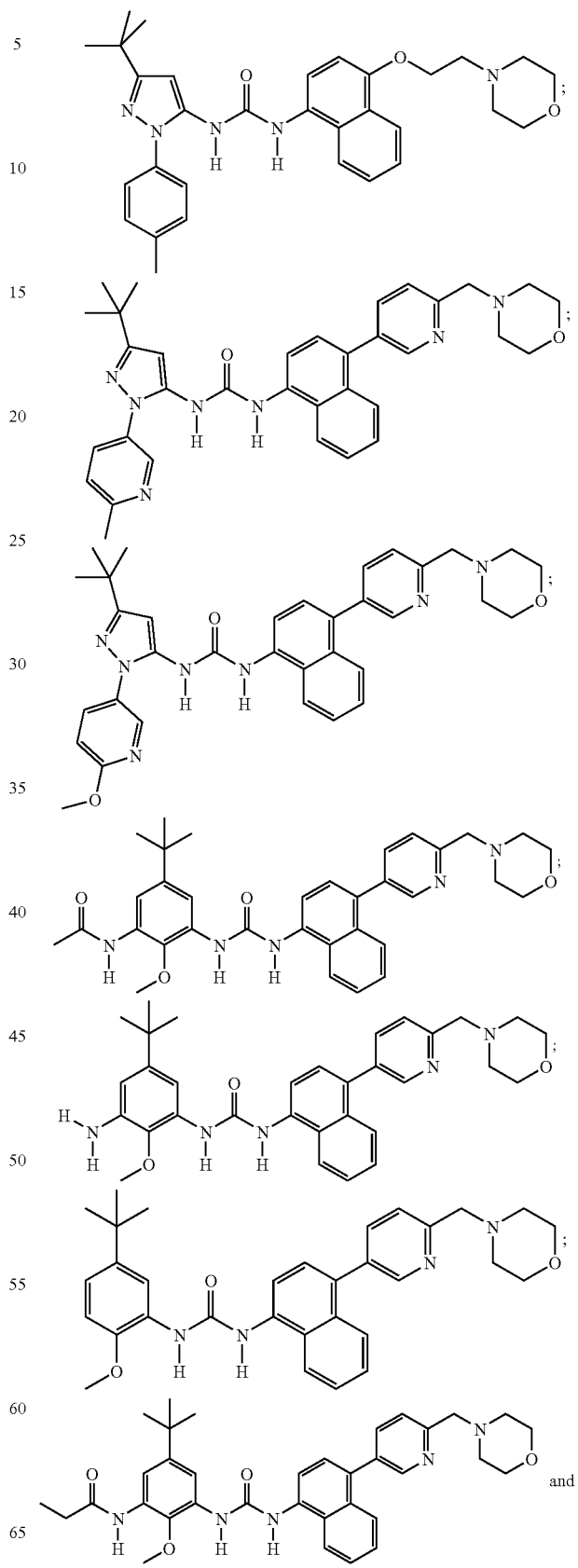

-continued

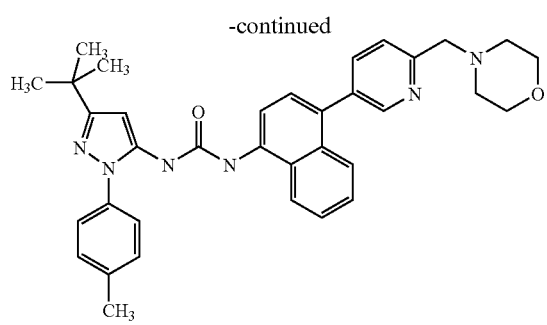

or the pharmaceutically acceptable salts thereof.

Particularily preferred, the p38 kinase inhibitors is:

Formula (III)

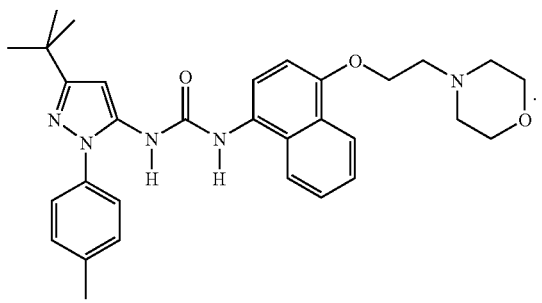

and the pharmaceutically acceptable derivatives thereof.

Any reference to the abovementioned p38 kinase inhibitors include "pharmaceutically acceptable derivative" thereof which refers to any pharmaceutically acceptable salt or ester of a compound of this invention, or any other compound which, upon administration to a patient, is capable of providing (directly or indirectly) a p38 kinase inhibitor of this invention, a pharmacologically active metabolite or pharmacologically active residue thereof. A pharmacologically active metabolite shall be understood to mean any compound capable of being metabolized enzymatically or chemically. This includes, for example, hydroxylated or oxidized derivative p 38 compounds.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1\text{-}C_4 \text{ alkyl})_4^+$ salts.

In addition, the compounds of this invention include prodrugs of p38 compounds. Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a p38 kinase inhibitor compound thereby imparting the desired pharmacological effect.

For prophylactic or therapeutic use, the pharmaceutical p38 kinase inhibitor compounds according to the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

p38 kinase inhibitors according to the invention may be administered separately, or in a combination formulation with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. For combination therapy with the drugs listed hereinbelow, advantageously, such combination therapies utilize lower dosages of the conventional therapeutics, thus avoiding possible toxicity and adverse side effects incurred when those agents are used as monotherapies. p38 kinase inhibitors may therefore be physically combined with the conventional therapeutics or other adjuvants into a single pharmaceutical composition. Regarding pharmaceutical compositions, reference may be made to Cappola et al.: U.S. patent application Ser. No. 09/902,822, PCT/US 01/21860 and U.S. provisional application No. 60/313,527, each incorporated by reference herein in their entirety. The optimum percentage (w/w) of a compound of the invention may vary and is within the purview of those skilled in the art.

As mentioned above, dosage forms of the compositions described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. p38 kinase inhibitor, in some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In another aspect the present invention relates to a pharmaceutical composition suitable for inhalation which contains one or more salts of a p38 kinase inhibitor, optionally in the form of their solvates or hydrates. The active substances may either be combined in a single preparation or contained in two separate formulations. Pharmaceutical compositions which contain the active p38 kinase inhibitor substances in a single preparation are preferred according to the invention.

Anticoagulant and Fibrinolytic Activity of P38 MAP Kinase Inhibitors

It has been found for the first time that p38 MAPK has a role in activation of coagulation, fibrinolysis and the vascular endothelium. The invention therefore provides a method of anticoagulant and fibrinolytic therapy for a disease or condition relating to blood coagulation or fibrinolysis comprising administering to a patient in need thereof a pharmaceutically effective a amount of a p38 MAP kinase inhibitor.

p38 MAP Kinase has been determined to have a role in the activation of the hemostatic mechanism in vivo. A possible explanation for the anticoagulant effect of p38 MAP kinase inhibitors is inhibition of tissue factor expression. Tissue factor is essential for activation of the coagulation system in this model of low grade endotoxemia [3,6], and p38 MAPK inhibition markedly diminished LPS-induced tissue factor expression by monocytic cells in vitro [9]. Moreover, p38 MAPK activation also mediates tissue factor expression by endothelial cells stimulated with thrombin or vascular endothelial growth factor, and by vascular smooth muscle cells stimulated with thrombin [10-12]. Furthermore, and not mutually exclusive, the reduced IL-6 concentrations in subjects treated with a preferred p38 MAP kinase inhibitor of the formula (III) may have contributed to the attenuated coagulant response, considering that IL-6 is an important mediator of coagulation activation by LPS in vivo [16].

Intravenous injection of LPS is associated with activation of the coagulation system, as reflected by a rise in the plasma concentrations of the prothrombin fragment F1+2. The effective dosage range for formula (III) is described in U.S. provisional application No. 60/339,249. High end dosing of formula (III) inhibited LPS-induced coagulation activation, both delaying and diminishing the increase in plasma F1+2 concentrations. Formula (III) had an even stronger inhibitory effect on activation of the fibrinolytic system p38 MAP kinase inhibitors also have an effect on endothelial cell activation, reflected by the plasma concentrations of sE-selectin and vWF [18-20]. Administration of LPS elicited profound increases in the plasma levels of sE-selectin and vWF, which were attenuated by high dose formula (III). p38 MAPK may play a direct role in signaling inflammatory effects into the interior of the vascular endothelium [10,11,21], including the expression of E-selectin on stimulated endothelial cells [22,23].

Methods of Therapeutic Use p38 compounds have been discovered for the first time to be useful in anticoagulant and finbrinolytic or thrombolytic therapy. Anticoagulants are used in treating acute venous thrombosis and pulmonary embolism. Thrombosis can also occur if the form of cerebral arterial embolism from cardiac sources such as ventricular mural thrombi or atrial thrombi or from an atherosclerotic, partially stenosed carotid or vertebral artery, or peripheral or mesenteric arterial thrombosis.

These agents may also be useful in preventing or treating thrombosis during pregancy, hemorrhagic skin necrosis, preventing or treating acute or chronic disseminated intravascular coagulation (DIC), prevention of clot formation occuring from surgery, long bed rest or long periods of immobilization such as that which occurs during air travel.

An example of a condition where an inhibitor of coagulation would be useful prohylactically is in the prevention or treatment of deep vein thrombosis (DVT). Current therapy involves anticoagulation with heparin. Venous thrombosis or thromophlebitis is caused by the presence of thrombus within a superficial or deep vein and the accompanying inflammatory response in the vessel wall The factors that predispose to venous thrombosis include stasis, vascular damage, and hypercoagulability and may occur in patients having orthopedic surgical procedures, particularly those involving the hip or knee, or patients who undergo abdominal or thoracic operations. The prevalence of venous thrombosis is particularly high in patients with cancer of the pancreas, lungs, genitourinary tract, stomach, and breast. Risk of thrombosis is increased following trauma, such as fractures of the spine, pelvis, femur, and tibia. Immobilization, regardless of the underlying disease, is a major predisposing cause of venous thrombosis.

An example of a disease where an agent that inhibits the fibrinolytic pathway would be useful is fulminant meningococcemia. Fulminant meningococcemia is perhaps the most rapidly lethal form of septic shock. Fibrinolytic therapy may also be an available treatment for patients with massive pulmonary embolism and systemic hypotension and to restore the patency of acutely occluded peripheral and coronary arteries. Timely fibrinolytic therapy may reduce both myocardial damage and mortality following acute coronary occlusion. Fibrinolytic therapy may also be effective in acute thrombotic strokes, acute coronary occlusion, acute peripheral arterial occlusion, massive pulmonary embolism with severe hypoxemia and hypotension, axillary vein thrombosis, massive iliofemoral vein thrombosis, occluded arterial or venous cannulae, cardiomyopathy, and venoocclusive disease of the liver.

Also with the scope of the invention is the combination therapy of a p38 inhibitor and one or more other anticoagulant or fibrinolytic agents. These include recombinant tissue plasminogen activator (rtPA), streptokinase (SK), urokinase (UK), proUK, heparin, enoxoparin, dalteparin, coumarin anticoagulants, aspirin, dipyrimidamole, aggrennox, ticlopidine, clopidogrel (Plavix), abciximab, RheoPro, integrilin, aggrestat and the like. Particular dosages, formulations and methods of administration either alone or combined is within the skill in the art.

The Examples which follow serve to illustrate the present invention in more detail without restricting the scope of the invention to the following embodiments by way of example.

Inhibition of P38 MAP Kinase

To determine binding affinities for compounds to p38 MAP kinase, a fluorescence binding assay is used as described [Pargellis, C., Tong, L., Churchill, L., Cirillo, P. F., Gilmore, T., Graham, A. G., Grob, P. M., Hickey, E. R., Moss, N., Pav, S. & Regan, J. Inhibition of p38 MAP kinase by utilizing a novel allosteric binding site. *Nature Structural Biology* 9, 268-272 (2002)]. Binding studies are conducted in aqueous solutions prepared using binding buffer: 20 mM Bis-TRIS Propane (pH 7.0), 2 mM EDTA, 0.01% $NaN_3$, and 0.15% n-octylglucoside. Kinetic data for the association of SK&F 86002 to p38 MAP kinase is collected on a Kintech fluorescence detector system equipped with a stopped flow controller. The data is fit simultaneously to an appropriate equation describing kinetic binding for a simple 1-step binding mechanism [Morelock, M. M., Pargellis, C. A., Graham, E. T., Lamarre, D. & Jung, G. Time-resolved ligand exchange reactions: kinetic models for competitive inhibitors with recombinant human renin. *J. Med. Chem.* 38, 1751-1761 (1995)]. The exchange curve assays are run as two half reactions using an SLM Aminco Bowman Series 2 Model SQ-340 fluorescence detector. Preliminary equilibrium are set up with two half reactions differing in the order of addition of the two p38 MAP kinase inhibitors. In the first half reaction, p38 MAP kinase and SK&F 86002 are preincubated for 3 minutes. In the second half reaction p38 MAP kinase is preincubated with BIRB 796 for 60 minutes. A net dissociation of the fluorescent probe, SK&F 86002, is observed for the first half reaction and a net association is observed for the second half reaction. The raw data from both half reactions are fitted simultaneously to an equation describing simple competitive inhibition[Morelock, M. M., Pargellis, C. A., Graham, E. T., Lamarre, D. & Jung, G. Time-resolved ligand exchange reactions: kinetic models for competitive inhibitors with recombinant human renin. *J. Med. Chem.* 38, 1751-1761 (1995)]. BIRB 796 (chemical name: 1-(5-tert-butyl-2-p-tolyl-2H-pyrazol-3-yl)-3-[4-(2-morpholin-4-yl-ethoxy)-naphthalen-1-yl]-urea) was synthesized as described [Cirillo, P., Gilmore, T. A., Hickey, E., Regan, J. & Zhang, L. H. Aromatic heterocyclic compounds as antiinflammatory agents. (WO0043384) Dec. 9, 1999].

Preferred compounds will have an $IC_{50}$<1 uM in this assay, confirming inhibition of p38 MAP Kinase.

EXAMPLE I

Synthesis of Formula (III)

Formula (III), p38 inhibitor:

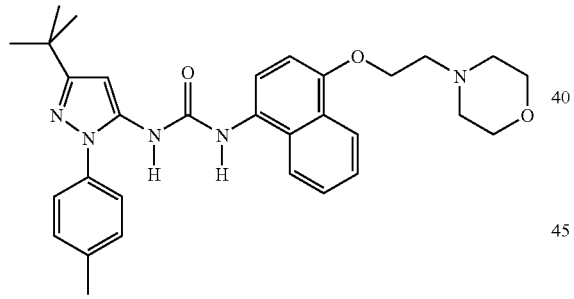

1-[3-tert-butyl-1-p-tolyl-1H-pyrazol-5-yl]-3-[4-(2-morpholin-4-yl-ethoxy)naphthalen-1-yl]-urea All p38 MAP kinase inhibitors described herein may be prepared by the methods found in the citations provided herein and by methods known in the art. Formula (III) may be obtained as described in U.S. Pat. No. 6,319,921 or U.S. application Ser. No. 09/611,109.

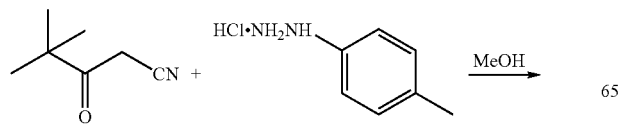

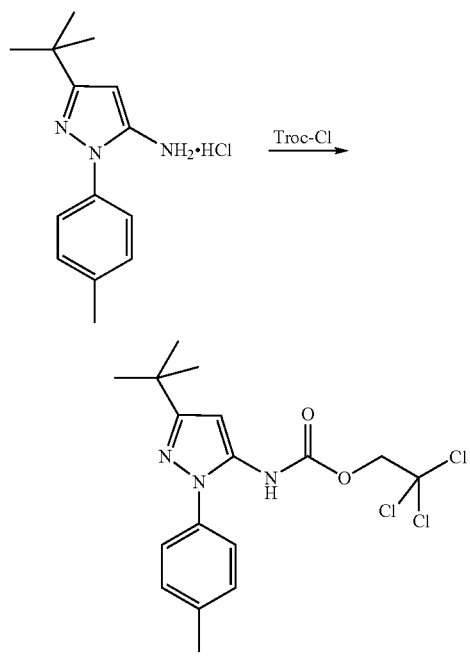

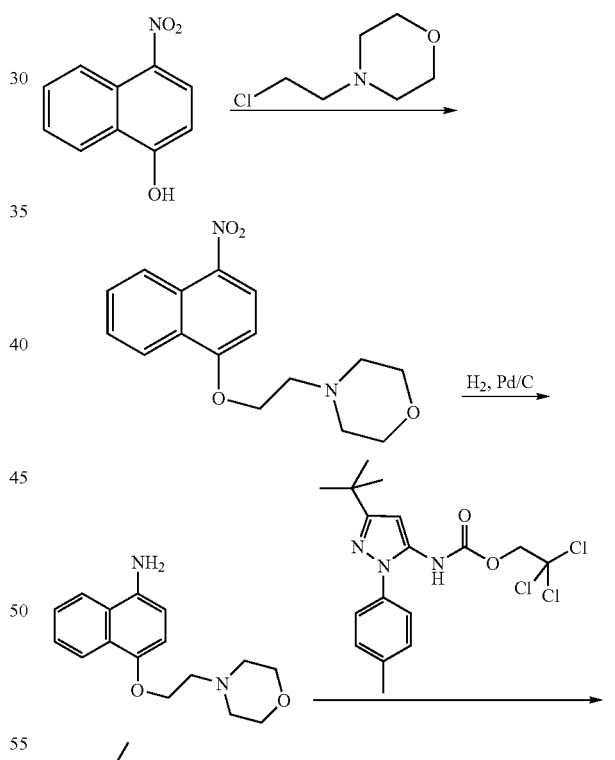

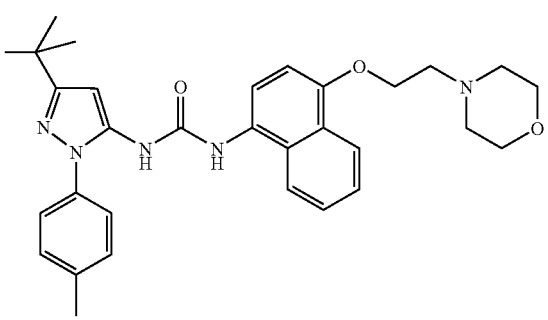

5-Amino-3-t-butyl-1-p-tolylpyrazole hydrochloride: A solution of pivaloylacetonitrile (750 g, 6.0 mol) and p-tolylhydrazine hydrochloride (660 g, 4.2 mol) in methanol (2.8 L) was refluxed for 3 h. Heptane was added, and methanol was removed by distillation. The product was crystallized from the solution, collected by filtration and dried in vacuum oven to constant weight. Yield: 1.05 kg, 94%. $^1$H NMR (CDCl$_3$) 7.50 (d, 2H), 7.30 (d, 2H), 5.60 (s, 1H), 2.45 (s, 3H), 1.40 (s, 9H). MS (CI) m/z 229 (M$^+$+H).

5-(2,2,2-Trichloroethoxycarbonyl)amino-3-t-butyl-1-p-tolylpyrazole: A mixture of 5-amino-3-t-butyl-1-p-tolylpyrazole hydrochloride (300 g, 1.13 mol), water (0.9 L), EtOAc (2.1 L) and NaOH (117 g, 2.84 mol) was stirred between 5-15° C. for 30 min. To this mixture, 2,2,2-trichloroethyl chloroformate (342 g, 1.58 mol) was added over 1 h between 5-15° C. The mixture was stirred at room temperature for 2 h, and then the aqueous layer was separated from the EtOAc layer. The EtOAc layer was washed with brine (2×0.9 L) and dried over MgSO$_4$ (60 g). The EtOAc layer was collected by filtration. To this solution, heptane was added. A part of the solution was removed by distillation. The product was crystallized from the solution, collected by filtration and dried in vacuum oven to constant weight. Yield: 409 g, 90%. $^1$H NMR (CDCl$_3$) 7.40 (d, 2H), 7.30 (d, 2H), 6.40 (s, 1H), 4.80 (s, 2H), 2.40 (s, 3H), 1.40 (s, 9H). MS (EI) m/z 404 (M$^+$).

4-Nitro-1-(2-morpholinethoxy)naphthalene: A mixture of 4-nitro-1-hydroxynaphthalene (194 g, 1.0 mol), 4-(2-chloroethyl)morpholine hydrochloride (264 g, 1.4 mol), NaOH (58 g, 1.4 mol), K$_2$CO$_3$ (339 g, 2.4 mol) and 1-methyl-2-pyrrolidinone (1.0 L) was heated to 90-100° C. and held for 1-2 h. The mixture was cooled to 40° C. and water was slowly added. The mixture was cooled to 5° C. and held for 4 h. The product was collected by filtration, washed with water, cyclohexane and dried in vacuum to constant weight. Yield: 227 g, 75%. $^1$H NMR (CDCl$_3$) 8.76 (d, 1H), 8.38 (m, 2H), 7.74 (dd, 1H), 7.58 (dd, 1H), 6.79 (d, 1H), 4.38 (dd, 2H), 3.74 (d, 4H), 2.98 (dd, 2H), 2.65 (d, 4H). MS (EI) m/z 303 (M+1).

4-Amino-1-(2-morpholinethoxy)naphthalene hydrochloride: A mixture of 4-nitro-1-(2-morpholinethoxy)naphthalene (40 g, 0.13 mol), MeOH (280 mL) and Pd/C (50% water, 1.2 g) was hydrogenated under 30 psi for 24 h. The catalyst was filtered through a layer of diatomaceous earth under nitrogen. To this filtrate 20 mL of HCl (37%) and cyclohexane (200 mL) were added. The solvent was removed under reduced pressure and the product collected by filtration. The product was dried in vacuum to constant weight. Yield: 33 g, 82%. $^1$H NMR (DMSO) 8.38 (d, 1H), 8.00 (d, 1H), 7.72 (dd, 1H), 7.64 (m, 2H), 7.05 (d, 1H), 4.62 (s, 2H), 4.00 (b, 4H), 3.88 (s, 2H), 3.40 (b, 4H). MS (EI) m/z 273 (M$^+$).

1-[3-tert-butyl-1-p-tolyl-1H-pyrazol-5-yl]-3-[4-(2-morpholin-4-yl-ethoxy)naphthalen-1-yl]-urea: A solution of 5-(2,2,2-trichloroethoxycarbonyl)amino-3-t-butyl-1-p-tolylpyrazole (10.6 g, 26 mmol), 4-amino-1-(2-morpholinethoxy)naphthalene (free base from HCl salt above, 7.16 g, 26 mmol), diisopropylethylamine (3.2 g, 25 mmol) and DMSO (75 mL) was heated to 55-60° C. and held for 1.5 h. To this solution, ethyl acetate (100 mL) was added. The organic layer was washed with brine (4×50 mL), and dried over MgSO$_4$. The solvent was removed under reduced pressure, and residue was crystallized from acetonitrile (50 mL) at 0° C. The product was collected by filtration, recrystallized from isopropanol and dried in vacuum to constant weight, m.p.: 151-152° C. Yield: 11.4 g, 87%. $^1$H NMR (DMSO) 8.75 (s, 1H), 8.51 (s, 1H), 8.21 (d, 1H), 7.85 (d, 1H), 7.65 (d, 1H), 7.55 (m, 2H), 7.49 (dd, 1H), 7.35 (dd, 1H), 6.95 (d, 1H), 6.38 (s, 1H), 4.26 (dd, 2H), 3.60 (dd, 4H), 2.81 (dd, 2H), 2.55 (dd, 4H), 2.38 (s, 3H), 1.29 (s, 9H). MS (CI) m/z 528 (M$^+$+1).

EXAMPLE II

LPS Study

This study was performed as a randomized, double-blind, placebo-controlled experiment and was performed simultaneously with a study examining the effect of formula (III) on LPS-induced cytokine release and neutrophil activation [14]. Briefly, LPS (from *E. coli*, lot G; United States Pharmacopeial Convention, Rockville, Md.; 4 ng/kg body weight) was administered as a bolus intravenous injection to 24 healthy male volunteers (mean age 22 years, range 19-29). Three hours prior to infusion of LPS, the p38 MAPK inhibitor (III) (600 mg n=8, 50 mg n=8) or placebo (n=8) was administered orally. Blood samples were obtained before administration of (III) or placebo (t=−3 h), directly before LPS administration (t=0 h), and at several time points up to 24 hours thereafter.

Assays

Blood was collected in siliconized vacutainer tubes (Becton Dickinson, Plymouth, England) containing 0.105 M sodium citrate in a 1:9 (v/v) anticoagulant:blood ratio. ELISA's were performed according to the instructions of the manufacturers: prothrombin fragment F1+2 (Dade Behring, Marburg GmbH, Germany), tissue-type plasminogen activator (tPA)(Asserachrom tPA, Diagnostic Stago, Asnieres-sur-Seine, France), plasminogen activator inhibitor type 1 (PAI-1) (Monozyme, Charlottelund, Denmark), Von Willebrand Factor (vWF) (Dakopatts, Ävlsjö, Sweden), and soluble E-selectin (sE-selectin)(Diaclone, Besancon Cedex, France); plasmin-2-antiplasmin complexes (PAPc) were determined by a radio immunoassay as described elsewhere [15].

Sepsis—Animal Models

Numerous animal models have been developed in which to simulate the clinical manifestation of septic shock in an attempt to gain further understanding of the disease state and to evaluate possible therapeutic agents. Smaller animal models such as mouse, rats and rabbits afford the investigator the advantages of a screening tool whereby results may be generated faster since larger numbers of animals can be used at one time, however, the disadvantages are that these species have reduced capacity for extensive biochemical analysis (smaller blood volume), show a higher tolerance for bacterial endotoxin (a highly antigenic portion of gram negative bacteria) and are more difficult to instrument when monitoring cardiovascular parameters. Thus, larger animal models are preferred when studying the cardiovascular response to sepsis. Specifically, primate models are described whereby continuous infusion live *E. coli* or endotoxin is used to simulate the human disease. It has been reported that intravenous administration of *E coli* or endotoxin can result in systemic hypotension, decreased cardiac output, decreased vascular resistance, pulmonary hypertension, diminished lung compliance, leukopenia and thrombocytopenia. In addition, cardiovascular response, blood flow, leukocyte function and blood coagulation have been studied in primates.

Animal Models—Venous Thrombosis

Numerous models have also been developed to study thrombosis in animals. Rabbit or rat model of venous or arterial thrombosis are know in the literature. Two typical models are:

Rabbit deep vein thrombosis model: Briefly, a non-occlusive fibrin-rich thrombus is formed on a thrombogenic surface (cotton threads attached to copper wire) introduced into the abdominal vena cava via the femoral vein of an anesthetized rabbit.

Rabbit/rat/dog arteriovenous shunt model: Briefly, the left femoral artery and vein is isolated, cannulated with polyethylene tubing and connected with a polyethylene shunt containing a 6-cm long cotton thread. The cotton thread is removed 15 min after blood begins to circulate through the shunt, and the thrombus-coated thread is weighed.

All references and patent publications cited in this application are incorporated by reference herein in their entirety.

REFERENCES

1. Levi M, Ten Cate H. Disseminated intravascular coagulation. N Engl J. Med. 1999; 341:586-592.
2. Van der Poll T, van Deventer S J H. Endotoxemia in healthy subjects as a human model of inflammation. In: Cohen J, Marshall J, ed. The Immune Response in the Critically Ill. Berlin:Springer-Verlag; 1999:335-357.
3. de Jonge E, Dekkers P E, Creasey A A, Hack C E, Paulson S K, Karim A, Kesecioglu J, Levi M, van Deventer S J, van Der Poll T. Tissue factor pathway inhibitor dose-dependently inhibits coagulation activation without influencing the fibrinolytic and cytokine response during human endotoxemia. Blood. 2000;95:1124-1129.
4. Creasey A A, Chang A C, Feigen L, Wun T C, Taylor F B, Jr., Hinshaw L B. Tissue factor pathway inhibitor reduces mortality from *Escherichia coli* septic shock. J Clin Invest. 1993; 91:2850-2856.
5. Carr C, Bild G S, Chang A C, Peer G T, Palmier M O, Frazier R B, Gustafson M E, Wun T C, Creasey A A, Hinshaw L B, et al. Recombinant *E. coli*-derived tissue factor pathway inhibitor reduces coagulopathic and lethal effects in the baboon gram-negative model of septic shock. Circ Shock. 1994; 44:126-137.
6. Levi M, ten Cate H, Bauer K A, van der Poll T, Edgington T S, Buller H R, van Deventer S J, Hack C E, ten Cate J W, Rosenberg R D. Inhibition of endotoxin-induced activation of coagulation and fibrinolysis by pentoxifylline or by a monoclonal anti-tissue factor antibody in chimpanzees. J Clin Invest. 1994; 93:114-120.
7. Herlaar E, Brown Z. p38 MAPK signalling cascades in inflammatory disease. Mol Med Today. 1999; 5:439-447.
8. Ono K, Han J. The p38 signal transduction pathway: activation and function. Cell Signal. 2000; 12:1-13.
9. Chu A J, Wang Z G, Walton M A, Seto A. Involvement of MAPK activation in bacterial endotoxin-inducible tissue factor upregulation in human monocytic THP-1 cells. J Surg Res. 2001; 101:85-90.
10. Blum S, Issbruker K, Willuweit A, Hehlgans S, Lucema M, Mechtcheriakova D, Walsh K, von der Ahe D, Hofer E, Clauss M. An inhibitory role of the phosphatidylinositol 3-kinase-signaling pathway in vascular endothelial growth factor-induced tissue factor expression. J Biol. Chem. 2001; 276:33428-33434.
11. Eto M, Kozai T, Cosentino F, Joch H, Luscher T F. Statin prevents tissue factor expression in human endothelial cells:role of Rho/Rho-kinase and Akt pathways. Circulation. 2002; 105:1756-1759.
12. Herkert O, Diebold I, Brandes R P, Hess J, Busse R, Gorlach A. NADPH oxidase mediates tissue factor-dependent surface procoagulant activity by thrombin in human vascular smooth muscle cells. Circulation. 2002; 105:2030-2036.
13. Pargellis C, Tong L, Churchill L, Cirillo P F, Gilmore T, Graham A G, Grob P M, Hickey E R, Moss N, Pav S, Regan J. Inhibition of p38 MAP kinase by utilizing a novel allosteric binding site. Nat Struct Biol. 2002; 9:268-272.
14. Branger J, van Den Blink B, Weijer S, Madwed J, Bos C L, Gupta A, Yong C L, Polmar S H, Olszyna D P, Hack C E, van Deventer S J, Peppelenbosch M P, van der Poll T. Anti-inflammatory effects of a p38 mitogen-activated protein kinase inhibitor during human endotoxemia. J. Immunol. 2002; 168:4070-4077.
15. Levi M, de Boer J P, Roem D, ten Cate J W, Hack C E. Plasminogen activation in vivo upon intravenous infusion of DDAVP. Quantitative assessment of plasmin-alpha 2-antiplasmin complex with a novel monoclonal antibody based radioimmunoassay. Thromb Haemost. 1992; 67:111-116.
16. van der Poll T, Levi M, Hack C E, ten Cate H, van Deventer S J, Eerenberg A J, de Groot E R, Jansen J, Gallati H, Buller H R, et al. Elimination of interleukin 6 attenuates coagulation activation in experimental endotoxemia in chimpanzees. J Exp Med. 1994; 179:1253-1259.
17. Uchiyama T, Kurabayashi M, Ohyama Y, Utsugi T, Akuzawa N, Sato M, Tomono S, Kawazu S, Nagai R. Hypoxia induces transcription of the plasminogen activator inhibitor-1 gene through genistein-sensitive tyrosine kinase pathways in vascular endothelial cells. Arterioscler Thromb Vasc Biol. 2000; 20:1155-1161.
18. van der Poll T, Coyle S M, Levi M, Jansen P M, Dentener M, Barbosa K, Buurman W A, Hack C E, ten Cate J W, Agosti J M, Lowry S F. Effect of a recombinant dimeric tumor necrosis factor receptor on inflammatory responses to intravenous endotoxin in normal humans. Blood. 1997; 89:3727-3734.
19. DeLa Cadena R A, Majluf-Cruz A, Stadnicki A, Tropea M, Reda D, Agosti J M, Colman R W, Suffredini A F. Recombinant tumor necrosis factor receptor p75 fusion protein (TNFR:Fc) alters endotoxin-induced activation of the kinin, fibrinolytic, and coagulation systems in normal humans. Thromb Haemost. 1998; 80:114-118.
20. Verbon A, Dekkers P E, ten Hove T, Hack C E, Pribble J P, Turner T, Souza S, Axtelle T, Hoek F J, van Deventer S J, van der Poll T. IC14, an anti-CD14 antibody, inhibits endotoxin-mediated symptoms and inflammatory responses in humans. J. Immunol. 2001; 166:3599-3605.
21. Marin V, Farnarier C, Gres S, Kaplanski S, Su M S, Dinarello C A, Kaplanski G. The p38 mitogen-activated protein kinase pathway plays a critical role in thrombin-induced endothelial chemokine production and leukocyte recruitment. Blood. 2001; 98:667-673.
22. Read M A, Whitley M Z, Gupta S, Pierce J W, Best J, Davis R J, Collins T. Tumor necrosis factor alpha-induced E-selectin expression is activated by the nuclear factor-kappaB and c-JUN N-terminal kinase/p38 mitogen-activated protein kinase pathways. J Biol. Chem. 1997; 272: 2753-2761.
23. Jersmann H P, Hii C S, Ferrante J V, Ferrante A. Bacterial lipopolysaccharide and tumor necrosis factor alpha synergistically increase expression of human endothelial adhesion molecules through activation of NF-kappaB and p38 mitogen-activated protein kinase signaling pathways. Infect Immun. 2001; 69:1273-1279.
24. Fijen J W, Zijlstra J G, De Boer P, Spanjersberg R, Cohen Tervaert J W, Van Der Werf T S, Ligtenberg J J, Tulleken J E. Suppression of the clinical and cytokine response to endotoxin by RWJ-67657, a p38 mitogen-activated protein-kinase inhibitor, in healthy human volunteers. Clin Exp Immunol. 2001; 124:16-20.

What is claimed is:

1. A method treating a disease or condition relating to blood coagulation or fibrinolysis comprising administering to a patient in need thereof a pharmaceutically effective a amount of a p38 MAP kinase inhibitor chosen from the group:

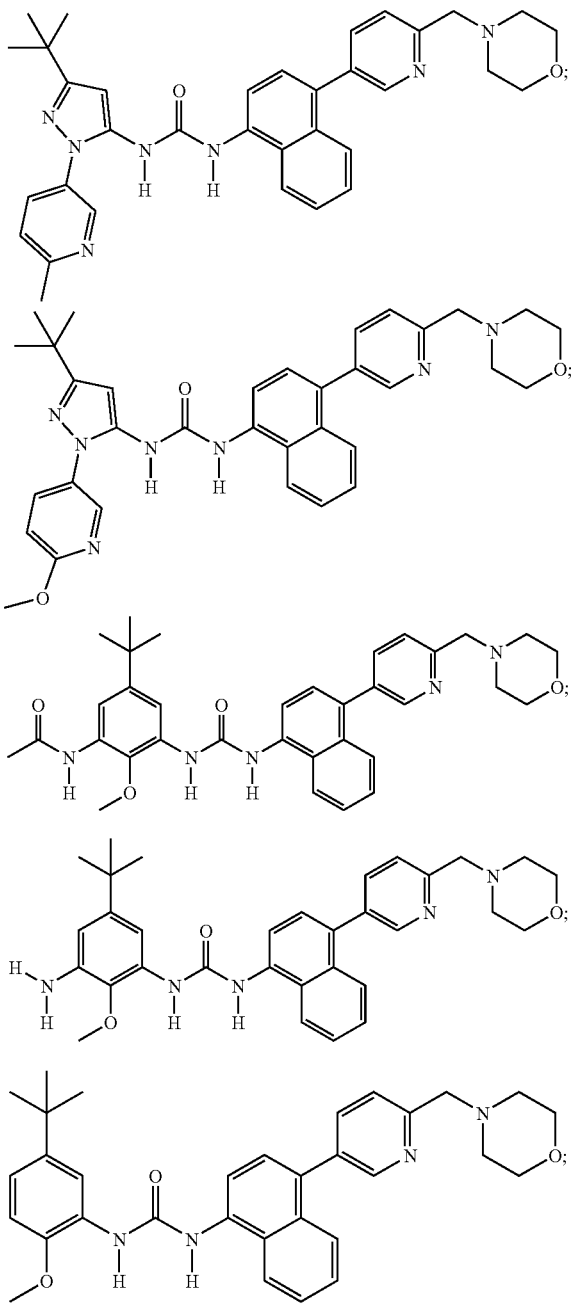

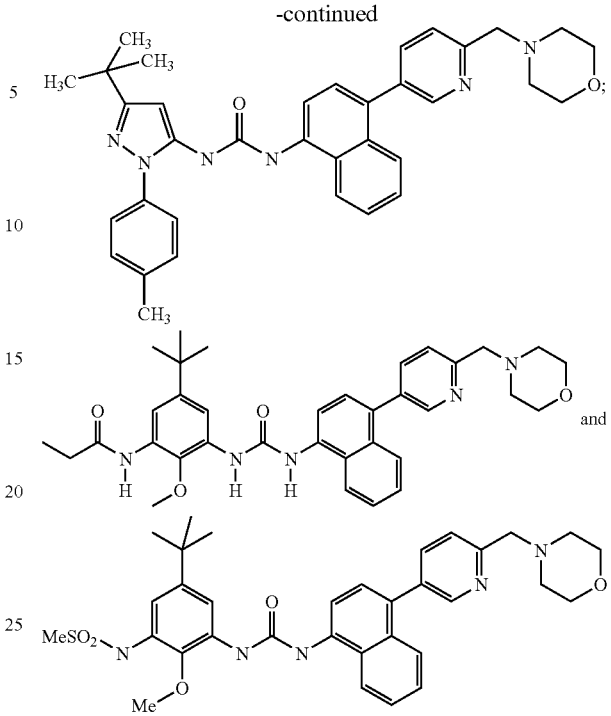

and the pharmaceutically acceptable salts thereof.

2. The method according to claim 1 wherein the disease or condition is caused by a clot, thrombosis or embolism.

3. The method according to claim 1 wherein the disease or condition is chosen from:

acute venous thrombosis, pulmonary embolism, thrombosis during pregancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia and thrombocytopenia.

4. The method according to one of claims 1-3 wherein the p38 MAP kinase inhibitor is provided in combination with one or more other anticoagulant or fibrinolytic agents.

5. The method according to claim 4 wherein the other anticoagulant or fibrinolytic agents are chosen from recombinant tissue plasminogen activator (rtPA), streptokinase (SK), urokinase (UK), proUK, heparin, enoxoparin, dalteparin, coumarin anticoagulants, aspirin, dipyrimidamole, aggrennox, ticlopidine, clopidogrel (Plavix), abciximab, RheoPro, integrilin, and aggrestat.

* * * * *